(12) United States Patent
Fujita et al.

(10) Patent No.: US 10,208,210 B2
(45) Date of Patent: *Feb. 19, 2019

(54) HYDROPHILIC OIL REPELLENT AND PRODUCTION METHOD OF SAME, SURFACE COATING MATERIAL, COATING FILM, RESIN COMPOSITION, OIL-WATER SEPARATION FILTER MATERIAL, AND POROUS BODY

(71) Applicants: MITSUBISHI MATERIALS CORPORATION, Tokyo (JP); Mitsubishi Materials Electronic Chemicals Co., Ltd., Akita-shi (JP)

(72) Inventors: Masato Fujita, Akita (JP); Masakazu Uotani, Akita (JP); Takeshi Kamiya, Akita (JP); Tsunetoshi Honda, Akita (JP); Daisuke Takano, Saitama (JP)

(73) Assignees: MITSUBISHI MATERIALS CORPORATION, Tokyo (JP); Mitsubishi Materials Electronic Chemicals Co., Ltd., Akita-shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/329,408

(22) PCT Filed: Jul. 29, 2015

(86) PCT No.: PCT/JP2015/071489
§ 371 (c)(1),
(2) Date: Jan. 26, 2017

(87) PCT Pub. No.: WO2016/017686
PCT Pub. Date: Feb. 4, 2016

(65) Prior Publication Data
US 2017/0210912 A1   Jul. 27, 2017

(30) Foreign Application Priority Data

Jul. 30, 2014 (JP) ................................ 2014-155553
Jul. 30, 2014 (JP) ................................ 2014-155554

(51) Int. Cl.
| | |
|---|---|
| *C09D 5/16* | (2006.01) |
| *B01D 17/02* | (2006.01) |
| *C09D 7/00* | (2018.01) |
| *C07C 229/12* | (2006.01) |
| *C07C 227/16* | (2006.01) |
| *C07C 233/05* | (2006.01) |
| *C07C 231/02* | (2006.01) |
| *C07C 311/05* | (2006.01) |

(Continued)

(52) U.S. Cl.
CPC .......... *C09D 5/1625* (2013.01); *B01D 17/02* (2013.01); *C02F 1/40* (2013.01); *C07C 227/06* (2013.01); *C07C 227/08* (2013.01); *C07C 227/16* (2013.01); *C07C 227/18* (2013.01); *C07C 229/06* (2013.01); *C07C 229/12* (2013.01); *C07C 231/02* (2013.01); *C07C 231/12* (2013.01); *C07C 233/05* (2013.01); *C07C 233/08* (2013.01); *C07C 303/02* (2013.01); *C07C 303/22* (2013.01); *C07C 303/38* (2013.01); *C07C 303/40* (2013.01); *C07C 309/04* (2013.01); *C07C 309/13* (2013.01); *C07C 309/29* (2013.01); *C07C 311/03* (2013.01); *C07C 311/05* (2013.01); *C07D 207/10* (2013.01); *C07D 211/38* (2013.01); *C07D 241/04* (2013.01); *C07D 265/30* (2013.01); *C08K 5/17* (2013.01); *C08L 101/00* (2013.01); *C09D 5/16* (2013.01); *C09D 7/20* (2018.01); *C09D 7/40* (2018.01); *C09D 201/00* (2013.01); *C09K 3/00* (2013.01); *Y02W 10/37* (2015.05)

(58) Field of Classification Search
CPC ......... B01D 17/02; C02F 1/40; C07C 227/16; C07C 227/12; C07C 231/02; C07C 233/05; C07C 303/02; C07C 303/38; C07C 309/13; C07C 311/05; C07D 207/10; C07D 211/38; C07D 241/04; C07D 265/30; C09D 5/1625; C09D 7/001
See application file for complete search history.

(56) References Cited

U.S. PATENT DOCUMENTS

| | | |
|---|---|---|
| 2,266,350 A | 12/1941 | Womack |
| 3,471,484 A | 10/1969 | Guenthner |
| (Continued) | | |

FOREIGN PATENT DOCUMENTS

| | | |
|---|---|---|
| AE | 1512348 A | 6/1978 |
| CN | 1805774 A | 7/2006 |
| (Continued) | | |

OTHER PUBLICATIONS

English translation of Japanese Patent No. 4406700 B2 (Nov. 2009).*

(Continued)

*Primary Examiner* — John Kim
(74) *Attorney, Agent, or Firm* — Locke Lord LLP; James E. Armstrong, IV; Nicholas J. DiCeglie, Jr.

(57) ABSTRACT

The hydrophilic oil repellent includes one or more types of nitrogen-containing fluorine-based compounds. The nitrogen-containing fluorine-based compound includes any one hydrophilicity imparting group selected from the group consisting of anion type hydrophilicity imparting groups, cation type hydrophilicity imparting groups, and amphoteric type hydrophilicity imparting groups in the molecule.

13 Claims, 1 Drawing Sheet

(51) Int. Cl.

| | |
|---|---|
| *C07C 303/38* | (2006.01) |
| *C07C 309/13* | (2006.01) |
| *C07C 303/02* | (2006.01) |
| *C07D 211/38* | (2006.01) |
| *C07D 265/30* | (2006.01) |
| *C07D 207/10* | (2006.01) |
| *C07D 241/04* | (2006.01) |
| *C02F 1/40* | (2006.01) |
| *C09D 7/40* | (2018.01) |
| *C07C 303/22* | (2006.01) |
| *C07C 303/40* | (2006.01) |
| *C07C 309/04* | (2006.01) |
| *C07C 309/29* | (2006.01) |
| *C07C 311/03* | (2006.01) |
| *C07C 227/06* | (2006.01) |
| *C07C 227/08* | (2006.01) |
| *C07C 227/18* | (2006.01) |
| *C07C 229/06* | (2006.01) |
| *C07C 231/12* | (2006.01) |
| *C07C 233/08* | (2006.01) |
| *C08K 5/17* | (2006.01) |
| *C09D 201/00* | (2006.01) |
| *C09K 3/00* | (2006.01) |
| *C08L 101/00* | (2006.01) |
| *C09D 7/20* | (2018.01) |

(56) References Cited

U.S. PATENT DOCUMENTS

| | | | |
|---|---|---|---|
| 4,859,754 | A | 8/1989 | Maekawa et al. |
| 5,443,724 | A | 8/1995 | Williamson et al. |
| 6,207,777 | B1 | 3/2001 | Shimada et al. |
| 2009/0317621 | A1 | 12/2009 | Youngblood et al. |

FOREIGN PATENT DOCUMENTS

| | | |
|---|---|---|
| GB | 1512348 A | 6/1978 |
| GB | 2354458 A | 3/2001 |
| JP | 45-002299 B | 1/1970 |
| JP | 45-006006 B1 | 2/1970 |
| JP | 46-031802 Y | 11/1971 |
| JP | 51-012462 A | 1/1976 |
| JP | 51-012463 A | 1/1976 |
| JP | 51-059133 U | 5/1976 |
| JP | 52-021130 U | 2/1977 |
| JP | 52-052182 A | 4/1977 |
| JP | 53-109266 A | 9/1978 |
| JP | 53-111569 A | 9/1978 |
| JP | 54-061362 A | 5/1979 |
| JP | 60-139306 A | 7/1985 |
| JP | 61-257211 A | 11/1986 |
| JP | 62-035738 Y | 9/1987 |
| JP | 63-037187 U | 3/1988 |
| JP | 03-060791 A | 3/1991 |
| JP | 03-144006 A | 6/1991 |
| JP | 05-058970 A | 3/1993 |
| JP | 05-137903 A | 6/1993 |
| JP | 05-177766 A | 7/1993 |
| JP | 05-272027 A | 10/1993 |
| JP | 05-329476 A | 12/1993 |
| JP | 05-331455 A | 12/1993 |
| JP | 06-134300 A | 5/1994 |
| JP | 07-004535 U | 1/1995 |
| JP | 07-024212 A | 1/1995 |
| JP | 07-048464 A | 2/1995 |
| JP | H07-204505 A | 8/1995 |
| JP | 07-265605 A | 10/1995 |
| JP | 07-284606 A | 10/1995 |
| JP | 07-289801 A | 11/1995 |
| JP | 08-243558 A | 9/1996 |
| JP | 09-094401 A | 4/1997 |
| JP | 09-227160 A | 9/1997 |
| JP | 10-006973 A | 1/1998 |
| JP | 10-007742 A | 1/1998 |
| JP | 10-103816 A | 4/1998 |
| JP | 10-204860 A | 8/1998 |
| JP | 11-021866 A | 1/1999 |
| JP | 11-114304 A | 4/1999 |
| JP | 11-156104 A | 6/1999 |
| JP | 11-244671 A | 9/1999 |
| JP | 11-323812 A | 11/1999 |
| JP | 2000-024656 A | 1/2000 |
| JP | 2000-096082 A | 4/2000 |
| JP | 2000-126505 A | 5/2000 |
| JP | 2000-189954 A | 7/2000 |
| JP | 2000-288303 A | 10/2000 |
| JP | 2000-342359 A | 12/2000 |
| JP | 2001-000960 A | 1/2001 |
| JP | 2001-004125 A | 1/2001 |
| JP | 2001-164450 A | 6/2001 |
| JP | 2001-220374 A | 8/2001 |
| JP | 2002-105433 A | 4/2002 |
| JP | 2002-266329 A | 9/2002 |
| JP | 2003-166173 A | 6/2003 |
| JP | 2003-227117 A | 8/2003 |
| JP | 2003-267900 A | 9/2003 |
| JP | 2004-098047 A | 4/2004 |
| JP | 2004-298711 A | 10/2004 |
| JP | 2005-144436 A | 6/2005 |
| JP | 2005-330354 A | 12/2005 |
| JP | 2006-110452 A | 4/2006 |
| JP | 2006-130743 A | 5/2006 |
| JP | 2006-198483 A | 8/2006 |
| JP | 2006-200269 A | 8/2006 |
| JP | 2006-292326 A | 10/2006 |
| JP | 2007-216184 A | 8/2007 |
| JP | 2007-326821 A | 12/2007 |
| JP | 2007-326836 A | 12/2007 |
| JP | 2008-031511 A | 2/2008 |
| JP | 2008-062127 A | 3/2008 |
| JP | 2009-061376 A | 3/2009 |
| JP | 2009-127015 A | 6/2009 |
| JP | 2009-133173 A | 6/2009 |
| JP | 4406700 B2 | 2/2010 |
| JP | 2010-159563 A | 7/2010 |
| JP | 2010-201321 A | 9/2010 |
| JP | 2011-011172 A | 1/2011 |
| JP | 2014-036931 A | 2/2014 |
| JP | 2014-148504 A | 8/2014 |
| JP | 2014-148670 A | 8/2014 |
| KR | 10-2015-0001082 A | 1/2015 |
| WO | 97/036951 A1 | 10/1997 |

OTHER PUBLICATIONS

International Search Report dated Oct. 20, 2015, issued for PCT/JP2015/071489 and English translation thereof.
International Search Report dated Oct. 20, 2015, issued for PCT/JP2015/071635 and English translation thereof.
International Search Report dated Oct. 20, 2015, issued for PCT/JP2015/071680 and English translation thereof.
International Search Report dated Oct. 27, 2015, issued for PCT/JP2015/071684 and English translation thereof.
International Search Report dated Oct. 20, 2015, issued for PCT/JP2015/071544 and English translation thereof.
International Search Report dated Oct. 27, 2015, issued for PCT/JP2015/071661 and English translation thereof.
Search Report dated Jan. 4, 2018, issued for the European Patent Application No. 15827683.2.
Search Report dated Jan. 8, 2018, issued for the European Patent Application No. 15827639.4.
Search Report dated Jan. 15, 2018, issued for the European Patent Application No. 15827185.8.
Office Action dated May 15, 2018, issued for the Chinese patent application No. 201580041432.X and a partial English translation of the Search Report.
Office Action dated Jul. 24, 2018, issued for the Japanese patent application No. 2015-013505 and English translation thereof.

(56) References Cited

OTHER PUBLICATIONS

Office Action dated Jul. 24, 2018, issued for the Japanese patent application No. 2015-013696 and English translation thereof.
Office Action dated Aug. 21, 2018, issued for the Japanese patent application No. 2014-238242 and English translation thereof.
Office Action dated Aug. 21, 2018, issued for the Japanese patent application No. 2014-256646 and English translation thereof.
Office Action dated Sep. 25, 2018, issued for the Japanese patent application No. 2015-007194 and English translation thereof.
Office Action dated Sep. 25, 2018, issued for the Japanese patent application No. 2015-009440 and English translation thereof.
Office Action dated Nov. 20, 2018, issued for the Japanese patent application No. 2015-013695 and English translation thereof.
Office Action dated Sep. 11, 2018, issued for the Japanese patent application No. 2015-009441 and English translation thereof.
Office Action dated Sep. 11, 2018, issued for the Japanese patent application No. 2015-013699 and English translation thereof.

* cited by examiner

HYDROPHILIC OIL REPELLENT AND PRODUCTION METHOD OF SAME, SURFACE COATING MATERIAL, COATING FILM, RESIN COMPOSITION, OIL-WATER SEPARATION FILTER MATERIAL, AND POROUS BODY

CROSS REFERENCE TO RELATED APPLICATIONS

This application is related to three co-pending applications: "OIL-WATER SEPARATION APPARATUS AND DRAINAGE SYSTEM" filed even date herewith in the names of Kosei SATO; Masato FUJITA; Masakazu UOTANI; Hiroshi KOSHIYAMA; Takeshi KAMIYA; Tsunetoshi HONDA; Hiroyuki IMAI and Daisuke TAKANO as a national phase entry of PCT/JP2015/071544; and "SURFACE COATING MATERIAL, COATING FILM, AND HYDROPHILIC OIL REPELLENT MEMBER" filed even date herewith in the names of Masakazu UOTANI; Hiroshi KOSHIYAMA; Takeshi KAMIYA; Tsunetoshi HONDA; Kosei SATO; Masato FUJITA and Daisuke TAKANO as a national phase entry of PCT/JP2015/071661; which applications are assigned to the assignee of the present application and all three incorporated by reference herein.

TECHNICAL FIELD

The present invention relates to a hydrophilic oil repellent and a production method of the same, a surface coating material, a coating film, a resin composition, an oil-water separation filter material, and a porous body.

Priority is claimed on Japanese Patent Application No. 2014-155553 and Japanese Patent Application No. 2014-155554, filed on Jul. 30, 2014, the contents of which are incorporated herein by reference.

BACKGROUND ART

In general, as an antifouling technique, it is desirable to impart oil repellency to make stains difficult to adhere and hydrophilicity to make the adhered stains be easily removed by washing with water to the substrate. As a technique to impart hydrophilicity to the substrate surface, a method in which a photocatalyst film is formed by immobilizing a photocatalyst such as titanium oxide on the substrate surface and the adhered stains are washed out by superhydrophilization by the action of the photocatalyst is known (Patent Document 1).

However, in a case where a photocatalyst film is used, although a function of easily removing stains can be obtained, there is a problem that the characteristic of preventing adhesion of stains is not sufficient. In particular, in an environment in which light necessary for exhibiting a photocatalytic function is not sufficiently obtained, sufficient antifouling properties are not obtained in some cases.

On the other hand, as a technique to impart oil repellency to the substrate surface, a method in which a fluorine-based compound is mainly used as a surface processing agent is known. As the fluorine-based compound, fluororesins such as polytetrafluoroethylene (PTFE) and compounds having a perfluoroalkyl group in the molecule are known. In a case where these fluorine-based compounds are used, although the water repellency is high, there is a problem that it is difficult to wipe off oil stains adhered to the surface or to remove by washing with water, like general hydrophobic coating films. In particular, in the case of being used in an environment where water is applied, inversely, there is a problem that oil stains easily adhere thereto.

A fluororesin hydrophilized by subjecting the surface to a plasma surface treatment, a flame treatment, an ozone treatment, or the like has been proposed (Patent Document 2), but the above-described special treatments are necessary, and the obtained hydrophilicity is also not sufficient. In addition, if hydrophilicity is imparted, there is a problem that the function of oil repellency is not obtained. Furthermore, there is a problem that a fluororesin is difficult to apply to a substrate surface and processed.

From the above, to impart a sufficient antifouling function to an object to be treated such as a substrate, a hydrophilic oil repellent which exhibits excellent hydrophilicity and excellent oil repellency at the same time has been demanded. In addition to the antifouling function, an excellent hydrophilic oil repellent is useful in a wide range of applications requiring quick drying properties of water accompanying improvement of wettability, an antifogging property, and oil-water separability. Among these, the hydrophilic oil repellent is particularly useful in oil-water separability applications.

However, among compounds in the related art, there is no compound which exhibits excellent hydrophilicity and excellent oil repellency at the same time, and it is difficult to impart a sufficient antifouling function and an oil-water separating function thereto.

CITATION LIST

Patent Literature

[Patent Document 1] Japanese Unexamined Patent Application, First Publication No. H09-227160

[Patent Document 2] Japanese Unexamined Patent Application, First Publication No. H05-177766

SUMMARY OF INVENTION

Technical Problem

The present invention has solved the above-described problems, and provides a novel hydrophilic oil repellent having excellent hydrophilicity and excellent oil repellency and a production method thereof. In addition, the present invention provides a surface coating material, a coating film, a resin composition, an oil-water separation filter material, and a porous body, including the hydrophilic oil repellent.

Solution to Problem

In a case where a fluorine-based compound is used as a surface processing agent, the treated surface typically shows water and oil repellency, and as the number of carbon atoms of the fluorine structure increases, the water repellency generally increases. However, as a result of thorough studies, the present inventors found that a compound obtained by adding a hydrophilicity imparting group to a specific nitrogen-containing perfluoro compound has unusual characteristics which could not be realized with the fluorine-based compounds in the related art, that is, hydrophilicity and oil repellency, and in particular, even a compound in which the number of carbon atoms of the fluorine structure is large exhibits excellent hydrophilicity and excellent oil repellency at the same time, and completed the present invention.

The present invention relates to a hydrophilic oil repellent in which the above problems have been solved by the configuration shown below, a production method of the same, a surface coating material, a coating film, a resin composition, an oil-water separation filter material, and a porous body, including the hydrophilic oil repellent.

[1] A hydrophilic oil repellent including one or more nitrogen-containing fluorine-based compounds represented by the following formulas (1) to (4).

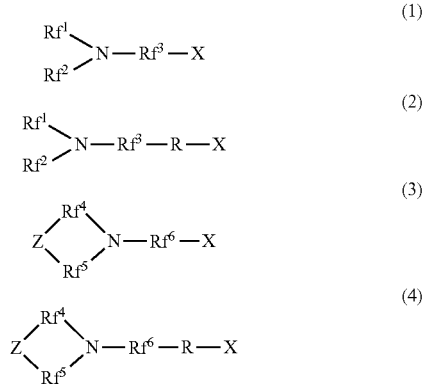

In the above formulas (1) and (2), $Rf^1$ and $Rf^2$ each represent a linear or branched perfluoroalkyl group having 1 to 6 carbon atoms, which are the same as or different from each other. In addition, $Rf^3$ represents a linear or branched perfluoroalkylene group having 1 to 6 carbon atoms.

In the above formulas (3) and (4), $Rf^4$, $Rf^5$, and $Rf^4$ each represent a linear or branched perfluoroalkylene group having 1 to 6 carbon atoms, which are the same as or different from each other. In addition, Z includes any one of an oxygen atom, a nitrogen atom, a $CF_2$ group, and a CF group.

In addition, in the above formulas (2) and (4), R represents a linking group which is a divalent organic group.

In addition, in the above formulas (1) to (4), X represents any one hydrophilicity imparting group selected from the group consisting of anion type hydrophilicity imparting groups, cation type hydrophilicity imparting groups, and amphoteric type hydrophilicity imparting groups.

[2] The hydrophilic oil repellent according to [1], in which, in the above formulas (1) to (4), X is an anion type hydrophilicity imparting group having "$—CO_2M^1$", "$—SO_3M^1$", "$—OSO_3M^1$", "$—OP(OH)O_2M^1$", "$—OPO_3M^1{}_2$", "$=O_2PO_2M^1$", or "$—PO(OH)_y(OM^1)_{2-y}$" ($M^1$ represents an alkali metal, an alkali earth metal, Mg, Al, or $R^1R^2R^3R^4N^+$; $R^1$ to $R^4$ are each independently a hydrogen atom or a linear or branched alkyl group having 1 to 20 carbon atoms, and y represents an integer of 0 to 2) at a terminal.

[3] The hydrophilic oil repellent according to [1], in which, in the above formulas (1) to (4), X is a cation type hydrophilicity imparting group having "$—N^+R^5R^6R^7.Cl^-$", "$—N^+R^5R^6R^7.Br^-$", "$—N^+R^5R^6R^7.I^-$", "$—N^+R^5R^6R^7.CH_3SO_3{}^-$", "$—N^+R^5R^6R^7.R^7SO_4{}^-$", "$—N^+R^5R^6R^7.NO_3{}^-$", "$(—N^+R^5R^6R^7)_2CO_3{}^{2-}$", or "$(—N^+R^5R^6R^7)_2SO_4{}^{2-}$" ($R^5$ to $R^7$ are each independently a hydrogen atom or a linear or branched alkyl group having 1 to 20 carbon atoms) at a terminal.

[4] The hydrophilic oil repellent according to [1], in which, in the above formulas (1) to (4), X is an amphoteric hydrophilicity imparting group having any one terminal of a carboxybetaine type, a sulfobetaine type, an amine oxide type, and a phosphobetaine type.

[5] A production method of the hydrophilic oil repellent according to [1], in which a carboxylic acid halide having a nitrogen-containing perfluoroalkyl group or a sulfonic acid halide having a nitrogen-containing perfluoroalkyl group represented by the following formula (5) or (6) is used as a raw material.

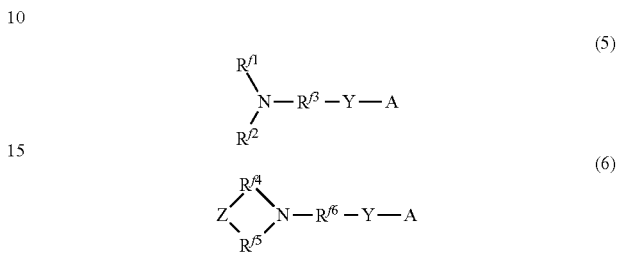

In the above formula (5), $Rf^1$ and $Rf^2$ each represent a linear or branched perfluoroalkyl group having 1 to 6 carbon atoms, which are the same as or different from each other. In addition, $Rf^3$ represents a linear or branched perfluoroalkylene group having 1 to 6 carbon atoms.

In the above formula (6), $Rf^4$, $Rf^5$, and $Rf^6$ each represent a linear or branched perfluoroalkylene group having 1 to 6 carbon atoms, which are the same as or different from each other. In addition, Z includes any one of an oxygen atom, a nitrogen atom, a $CF_2$ group, and a CF group.

In addition, in the above formulas (5) and (6), Y represents CO or $SO_2$.

Furthermore, in the above formulas (5) and (6), A represents any one halogen atom selected from the group consisting of fluorine, chlorine, bromine, and iodine.

[6] A surface coating material including the hydrophilic oil repellent according to [1] and a solvent, in which the mass composition ratio between the hydrophilic oil repellent and the solvent is within a range of 0.2 to 50:99.8 to 50.

[7] The surface coating material according to [6], in which the solvent is water, an alcohol, or a mixture of water and an alcohol.

[8] The surface coating material according to [6] or [7], in which further including a binder, in which the mass composition ratio between the hydrophilic oil repellent and the binder is within a range of 0.2 to 99.9:99.8 to 0.1.

[9] The surface coating material according to any one of [6] to [8], in which the binder includes any one of a resin, a water soluble resin, and water glass.

[10] A coating film including the hydrophilic oil repellent according to [1].

[11] The coating film according to [10] further including a binder, in which the mass composition ratio between the hydrophilic oil repellent and the binder is within a range of 0.2 to 99.9:99.8 to 0.1.

[12] A resin composition including the hydrophilic oil repellent according to [1] and a resin, in which the mass composition ratio between the hydrophilic oil repellent and the resin is within a range of 0.2 to 99.9:99.8 to 0.1.

[13] A porous body including the hydrophilic oil repellent according to [1].

[14] A porous body, in which the hydrophilic oil repellent according to [1] is bonded with a resin or a vitreous material.

[15] An oil-water separation filter material including any one or more of the coating film according to [10] or [11], the resin composition according to [12], and the porous body according to [13] or [14].

Advantageous Effects of Invention

Since the hydrophilic oil repellent of the present invention includes an oil repellency imparting group formed of a nitrogen-containing perfluoroalkyl group and any one of an anion type hydrophilicity imparting group, a cation type hydrophilicity imparting group, and an amphoteric type hydrophilicity imparting group in the molecule, the hydrophilic oil repellent has excellent hydrophilicity and excellent oil repellency (hydrophilicity and oil repellency). Furthermore, by using this hydrophilic oil repellent, it is possible to easily form a surface coating material, a coating film, a resin composition, an oil-water separation filter material, and a porous body, having excellent hydrophilicity and oil repellency.

In the production method of the hydrophilic oil repellent of the present invention, a carboxylic acid halide having a nitrogen-containing perfluoroalkyl group or a sulfonic acid halide having a nitrogen-containing perfluoroalkyl group is used as a raw material, and thus, it is possible to easily synthesize various derivatives.

DESCRIPTION OF EMBODIMENTS

Figure 1:
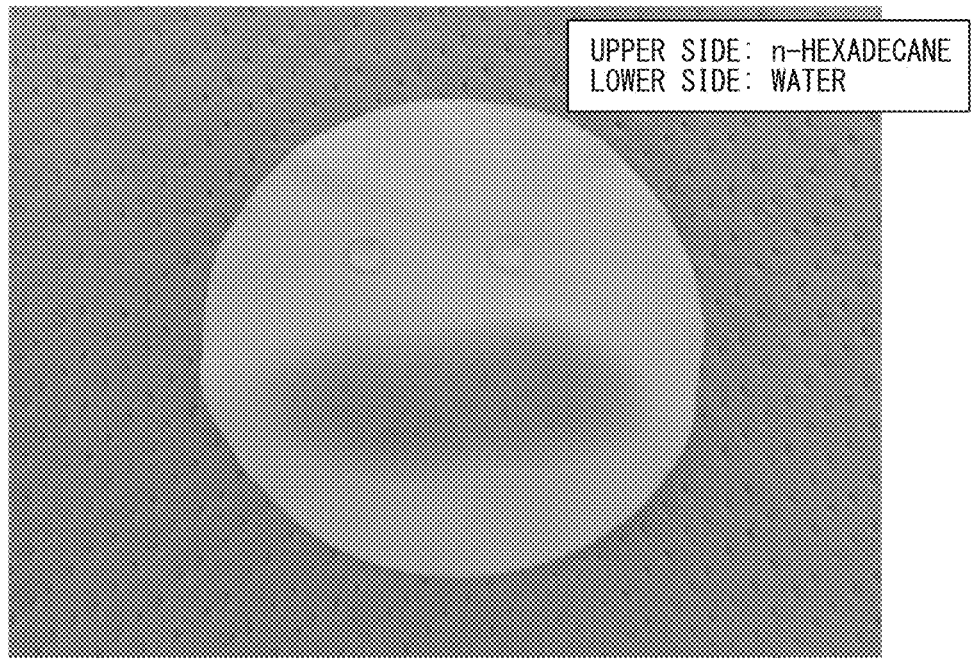
FIG. 1 is a photograph showing the results of a PTFE filter penetration test according to an example.

Hereinafter, a hydrophilic oil repellent which is one embodiment to which the present invention is applied will be described in detail together with a production method thereof a surface coating material, a coating film, a resin composition, a oil-water separation filter material, and a porous body, including the hydrophilic oil repellent.

<Hydrophilic Oil Repellent>

First, the configuration of the hydrophilic oil repellent which is one embodiment to which the present invention is applied will be described.

The hydrophilic oil repellent of the present embodiment is a nitrogen-containing fluorine-based compound represented by each of the following formulas (1) to (4), or a mixture including two or more nitrogen-containing fluorine-based compounds selected from the group consisting of nitrogen-containing fluorine-based compounds represented by the following formulas (1) to (4).

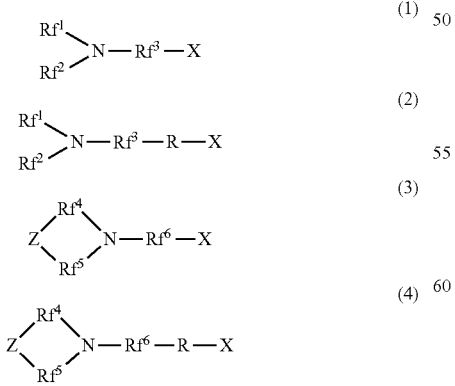

Here, in the above formulas (1) and (2), $Rf^1$ and $Rf^2$ each represent a linear or branched perfluoroalkyl group having 1 to 6 carbon atoms, which are the same as or different from each other. In addition, $Rf^3$ represents a linear or branched perfluoroalkylene group having 1 to 6 carbon atoms.

$Rf^1$ and $Rf^2$ each preferably represent a linear or branched perfluoroalkyl group having 1 to 4 carbon atoms, which are the same as or different from each other. In addition, $Rf^3$ preferably represents a linear or branched perfluoroalkylene group having 1 to 4 carbon atoms.

In addition, in the above formulas (3) and (4), $Rf^4$, $Rf^5$, and $Rf^4$ each represent a linear or branched perfluoroalkylene group having 1 to 6 carbon atoms, which are the same as or different from each other. In addition, Z includes any one of an oxygen atom, a nitrogen atom, a $CF_2$ group, and a CF group. In addition, in a case where Z includes a nitrogen atom or a CF group, a perfluoroalkyl group branched from Z may be bonded to Z.

$Rf^4$, $Rf^5$, and $Rf^6$ each preferably represent a linear or branched perfluoroalkylene group having 1 to 4 carbon atoms, which are the same as or different from each other.

In addition, in the above formulas (2) and (4), R represents a linking group which is a divalent organic group. Here, R may be a linear or branched organic group. In addition, R may or may not include one or more types of functional groups selected from an ether bond, an ester bond, an amide bond, and a urethane bond in the molecular chain.

In addition, in the above formulas (1) to (4), X is any one hydrophilicity imparting group selected from the group consisting of anion type hydrophilicity imparting groups, cation type hydrophilicity imparting groups, and amphoteric type hydrophilicity imparting groups.

Hereinafter, the nitrogen-containing fluorine-based compound will be described in detail.

(Linear Nitrogen-Containing Fluorine-Based Compound)

In the linear (or branched) nitrogen-containing fluorine-based compound represented by the above formula (1) or (2), a nitrogen-containing perfluoroalkyl group formed of $Rf^1$ and Re and a nitrogen-containing perfluoroalkylene group formed of $Rf^3$ configure an oil repellency imparting group.

In addition, in the nitrogen-containing fluorine-based compound represented by the above formula (1) or (2), the total number of carbon atoms to which fluorine is bonded, in $Rf^1$ to $Rf^3$ which are the oil repellency imparting groups is preferably within a range of 4 to 18. If the number of carbon atoms to which fluorine is bonded is less than 4, since an oil repellent effect is not sufficient, this is not preferable.

Specific examples of the structure of the oil repellency imparting group in the above formula (1) or (2) include structures of the following formulas (7) to (24).

[Chem. 11]

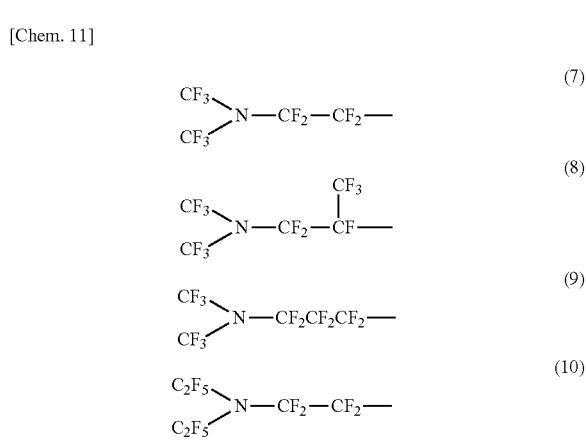

-continued

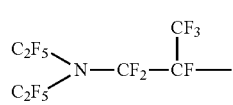 (11)

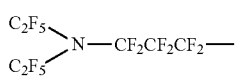 (12)

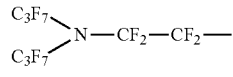 (13)

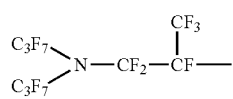 (14)

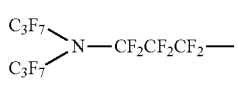 (15)

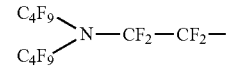 (16)

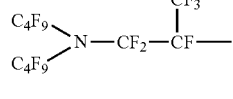 (17)

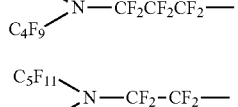 (18)

 (19)

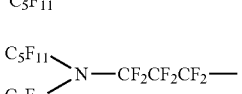 (20)

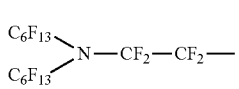 (21)

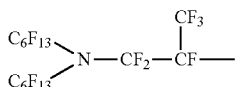 (22)

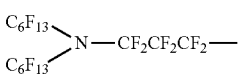 (23)

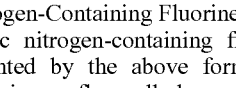 (24)

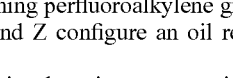

(Cyclic Nitrogen-Containing Fluorine-Based Compound)

In the cyclic nitrogen-containing fluorine-based compound represented by the above formula (3) or (4), a nitrogen-containing perfluoroalkylene group formed of $Rf^4$, $Rf^5$, and $Rf^6$, and Z configure an oil repellency imparting group.

In addition, in the nitrogen-containing fluorine-based compound represented by the above formula (3) or (4), the total number of carbon atoms to which fluorine is bonded, in $Rf^4$ to $Rf^6$ and Z which are the oil repellency imparting groups is preferably within a range of 4 to 18, and more preferably within a range of 5 to 12. If the number of carbon atoms to which fluorine is bonded is less than 4, since an oil repellent effect is not sufficient, this is not preferable.

Specific examples of the structure of the oil repellency imparting group in the above formula (3) or (4) include structures of the following formulas (25) to (49).

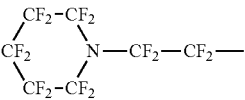 (25)

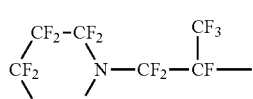 (26)

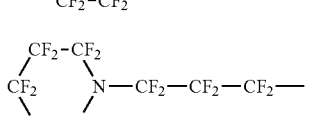 (27)

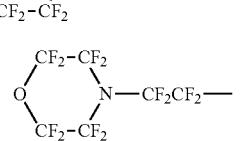 (28)

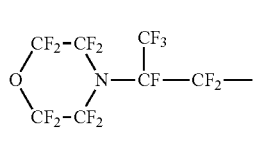 (29)

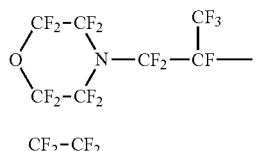 (30)

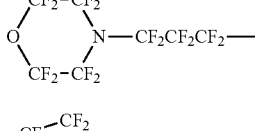 (31)

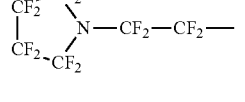 (32)

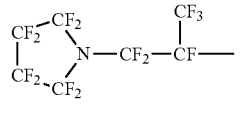 (33)

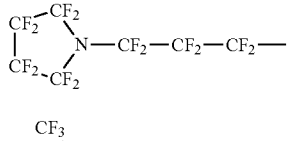 (34)

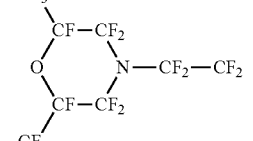 (35)

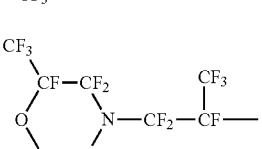 (36)

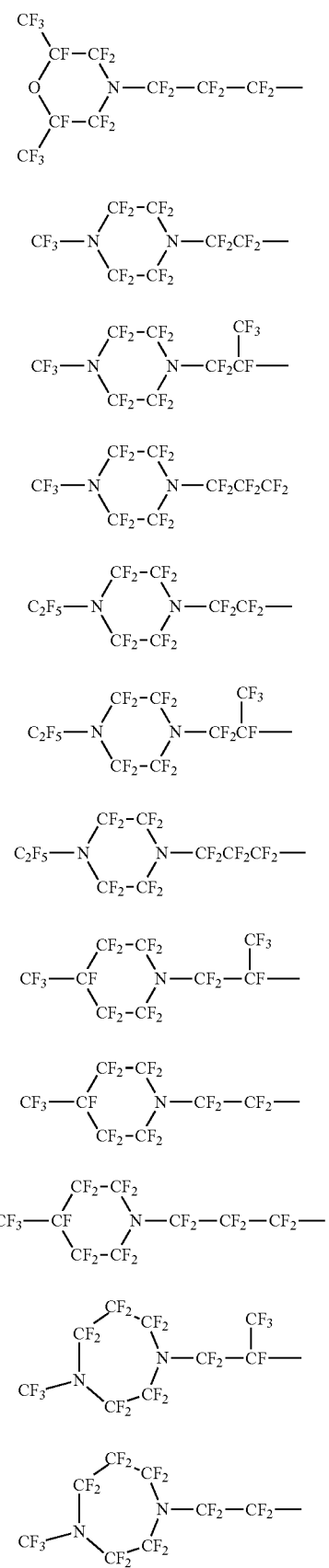

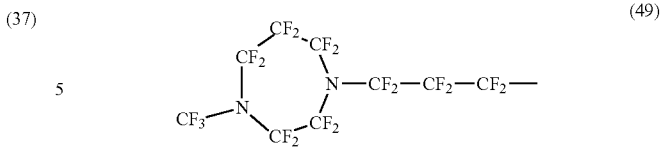

Here, in the above formulas (2) and (4), R is a linking group connecting an oil repellency imparting group and a hydrophilicity imparting group in the molecular chain. The structure of the linking group R is not particularly limited as long as it is a divalent organic group. Specific examples of the linking group R include an oxygen atom [—O—], a carbonyl group [—C(=O)—], an imino group [—NH—], a sulfonyl group [—S(=O)$_2$—], an —OP(=O)(O$^-$)O— group, a hydrocarbon group having 1 to 20 carbon atoms, and combinations thereof. In addition, the linking group R may include one or more selected from polyoxyalkylene groups and epoxy groups. The hydrocarbon group may be a saturated hydrocarbon group or an unsaturated hydrocarbon group. In addition, the hydrocarbon group may be a chain-like hydrocarbon group or a cyclic hydrocarbon group. The chainlike hydrocarbon group may be linear or branched. Examples of the hydrocarbon group include an alkylene group, an alkenylene group, and an arylene group. The imino group and the hydrocarbon group may have a substituent.

In addition, the linking group R may or may not include one or more types of bonds selected from an ether bond, an ester bond, an amide bond, and a urethane bond in the molecular chain. The amide bond includes a carboxylic acid amide bond and a sulfonamide bond. The ester bond includes a carboxylic acid ester bond, a sulfonic acid ester bond, and a phosphoric acid ester bond.

The linking group R is preferably suitably selected and introduced, according to the characteristics desired to be imparted to the nitrogen-containing fluorine-based compound. Specific examples thereof include a case where it is desired to adjust the solubility in a solvent, a case where it is desired to improve durability by improving adhesion to a substrate, and a case where it is desired to improve compatibility with a resin component or the like. As the method, there are a method of adjusting the presence or absence and the type of polar group affecting intermolecular interaction, a method of adjusting the chain length of a hydrocarbon group having a linear or branched structure, and a method of introducing a structure similar to a part of the chemical structure included in the substrate or the resin component.

In addition, in the above formulas (1) to (4), X is any one hydrophilicity imparting group selected from the group consisting of anion type hydrophilicity imparting groups, cation type hydrophilicity imparting groups, and amphoteric type hydrophilicity imparting groups.

Hereinafter, the structure of the hydrophilic oil repellent of the present embodiment will be described by dividing the hydrophilicity imparting groups X into cases.

(Anion Type)

In a case where the hydrophilicity imparting group X is an anion type, X is an anion type hydrophilicity imparting group having "—CO$_2$M$^1$", "—SO$_3$M$^1$", "—OSO$_3$M$^1$", "—OP(OH)O$_2$M$^1$", "—OPO$_3$M$^1_2$", "=O$_2$PO$_2$M$^1$", or "—PO(OH)$_y$(OM$^1$)$_{2-y}$," (M$^1$ represents an alkali metal, an alkali earth metal, Mg, Al, or R$^1$R$^2$R$^3$R$^4$N$^+$; R$^1$ to R$^4$ are each independently a hydrogen atom or a linear or branched alkyl group having 1 to 20 carbon atoms, and preferably having 1 to 10 carbon atoms, and y represents an integer of 0 to 2) at the terminal. The above-described structure example of the terminal shows a case where $M^1$ is monovalent. In addition, in a case where $M^1$ is divalent, two identical anions may be bonded to $M^1$, or two different types of anions may be bound to $M^1$.

Examples of the alkali metal include lithium (Li), sodium (Na), potassium (K), and cesium (Cs). In addition, examples of the alkali earth metal include calcium (Ca), strontium (Sr), and barium (Ba).

In addition, the quaternary ammonium salt ($R^1R^2R^3R^4N^+$) is not particularly limited as long as $R^1$ to $R^4$ are each independently a hydrogen atom or a linear or branched alkyl group having 1 to 20 carbon atoms, and preferably having 1 to 10 carbon atoms. Here, if the number of carbon atoms of the alkyl group is 20 or less, since the hydrophilicity and oil repellency is not impaired, this is preferable. More specific examples of the compound in which all of $R^1$, $R^2$, $R^3$, and $R^4$ are the same include $(CH_3)_4N^+$, $(C_2H_5)_4N^+$, $(C_3H_7)_4N^+$, $(C_4H_9)_4N^+$, $(C_5H_{11})_4N^+$, $(C_6H_{13})_4N^+$, $(C_7H_{15})_4N^+$, $(C_8H_{17})_4N^+$, $(C_9H_{19})_4N^+$, and $(C_{10}H_{21})_4N^+$. In addition, as a case where all of $R^1$, $R^2$, and $R^3$ are methyl groups, a compound in which $R^4$ is $(C_2H_5)$, $(C_6H_{13})$, $(C_8H_{17})$, $(C_9H_{19})$, $(C_{10}H_{21})$, $(C_{12}H_{25})$, $(C_{14}H_{29})$, $(C_{16}H_{33})$, or $(C_{18}H_{37})$ is an exemplary example. Furthermore, as a case where both $R^1$ and $R^2$ are methyl groups, a compound in which both $R^3$ and $R^4$ are $(C_8H_{17})$, $(C_{10}H_{21})$, $(C_{12}H_{25})$, $(C_{14}H_{29})$, $(C_{16}H_{33})$, or $(C_{18}H_{37})$ is an exemplary example. In addition, as a case where $R^1$ is a methyl group, a compound in which all of $R^2$, $R^3$ and $R^4$ are $(C_4H_9)$ or $(C_8H_{17})$ is an exemplary example.

In applications used in contact with water, it is desired to have durability against water and persistence of a hydrophilic oil repellent effect. From the above viewpoint, in the hydrophilic oil repellent of the present embodiment, a nitrogen-containing fluorine-base compound is desired to be a sparingly soluble compound having low solubility in water. That is, in a case where the hydrophilicity imparting group X is an anion type, in the hydrophilic oil repellent of the present embodiment, $M^1$ which is a counter ion is preferably an alkali earth metal, Mg, or Al, and, in particular, Ca, Ba, and Mg are preferable since they have excellent hydrophilicity and oil repellency and low solubility in water.

Here, in a case where the hydrophilicity imparting group X is an anion type, specific examples (here, the structure of $M^1$ which is a counter ion is excluded) of the structure of the hydrophilic oil repellent represented by the formula (1) or (2) (that is, a linear nitrogen-containing fluorine-based compound) include structures of the following formulas (50) to (117).

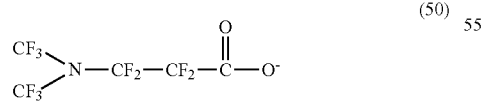
(50)

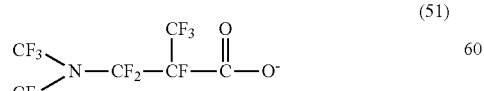
(51)

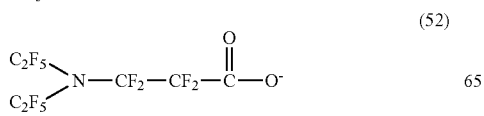
(52)

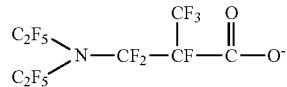
(53)

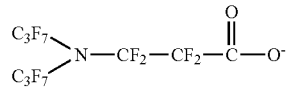
(54)

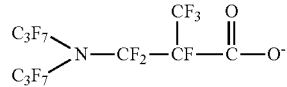
(55)

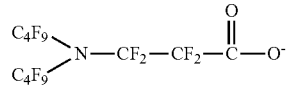
(56)

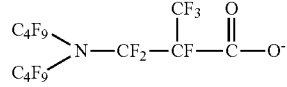
(57)

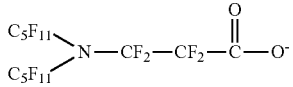
(58)

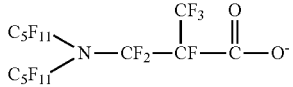
(59)

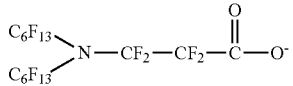
(60)

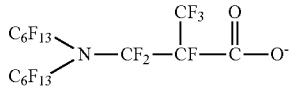
(61)

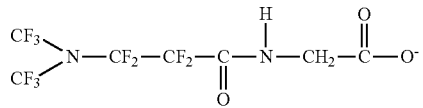
(62)

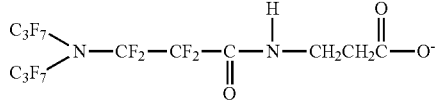
(63)

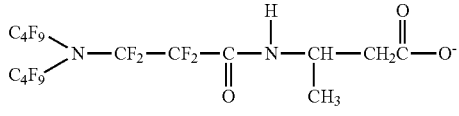
(64)

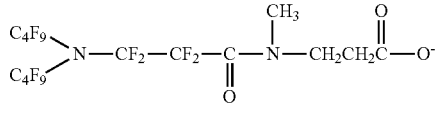
(65)

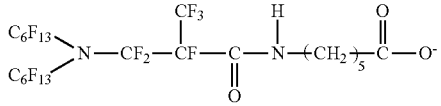
(66)

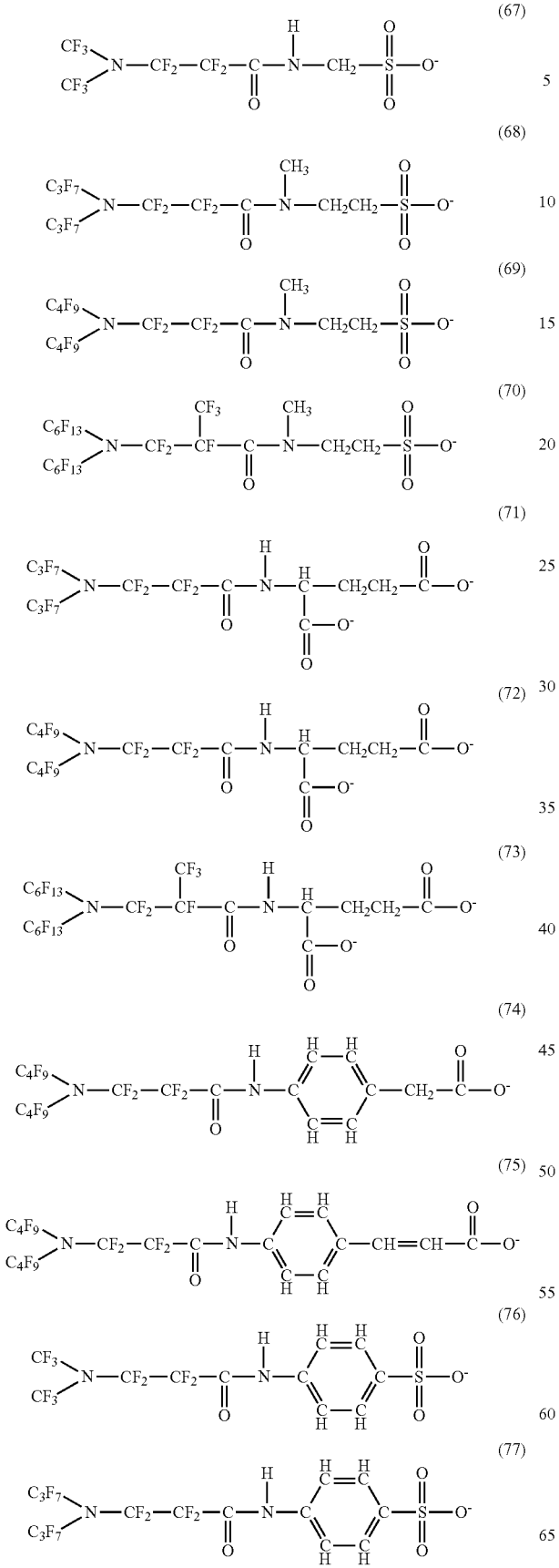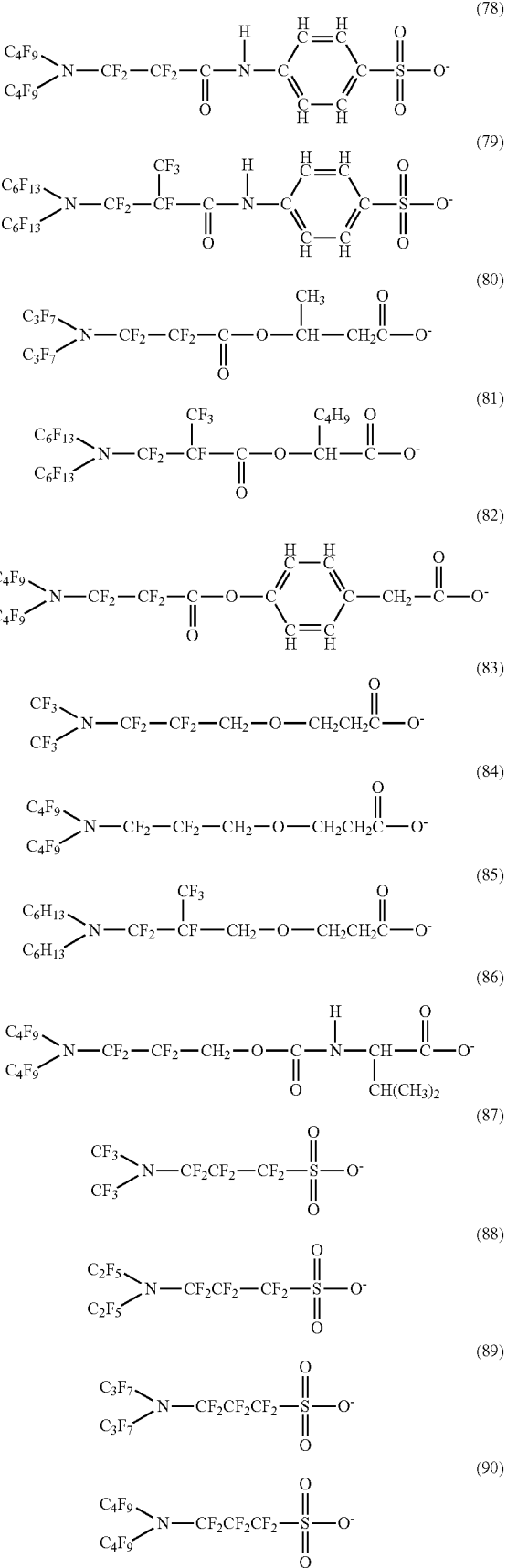

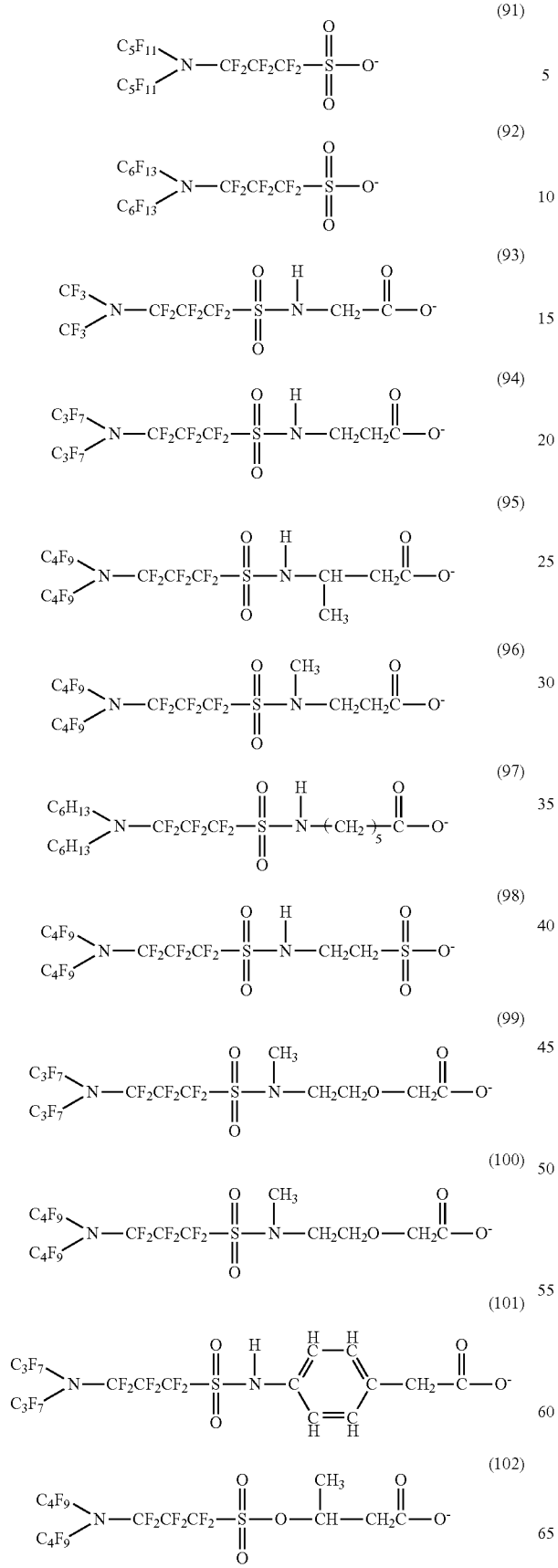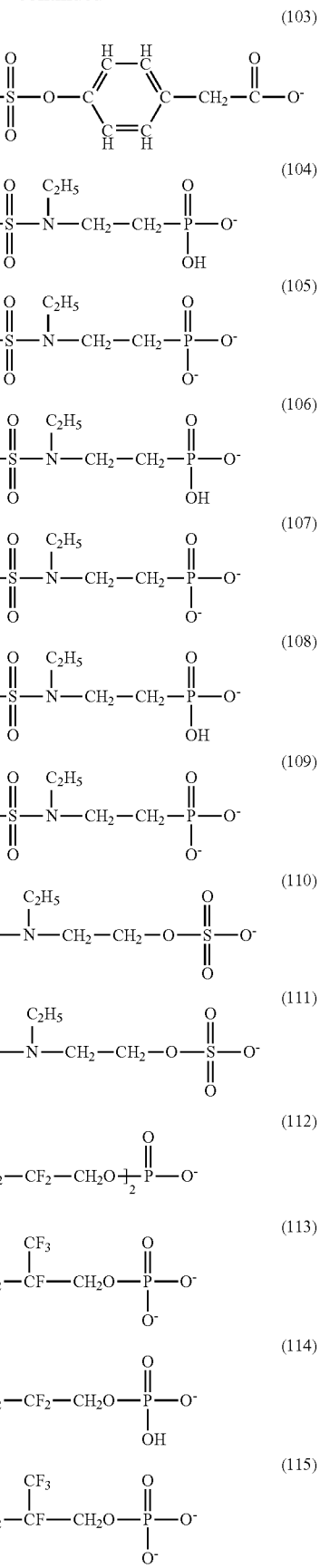

-continued
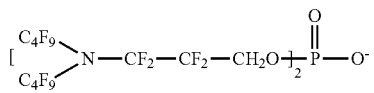 (116)
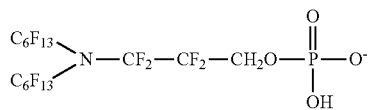 (117)
In contrast, specific examples (here, the structure of $M^1$ which is a counter ion is excluded) of the structure of the hydrophilic oil repellent represented by the formula (3) or (4) (that is, a cyclic nitrogen-containing fluorine-based compound) include structures of the following formulas (118) to (189).
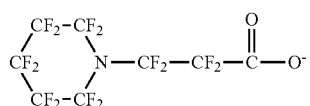 (118)
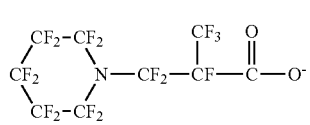 (119)
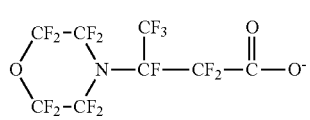 (120)
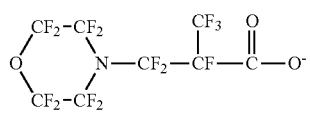 (121)
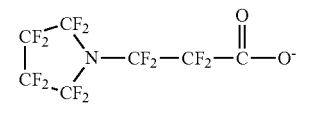 (122)
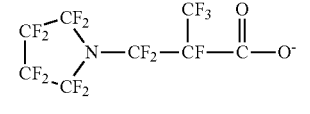 (123)
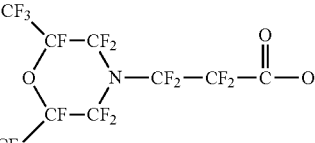 (124)
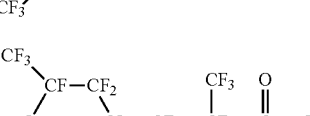 (125)
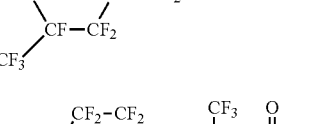 (126)
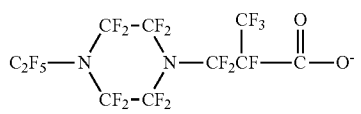 (127)
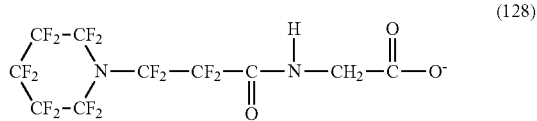 (128)
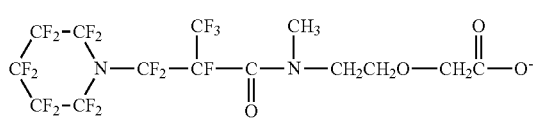 (129)
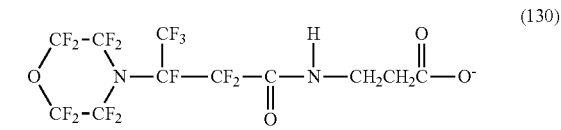 (130)
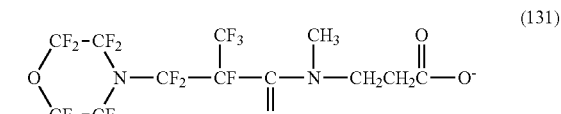 (131)
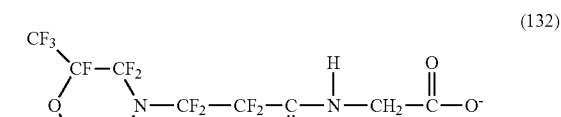 (132)
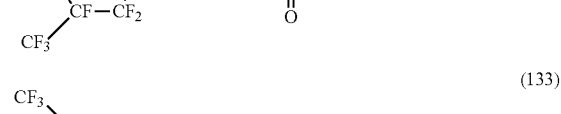 (133)
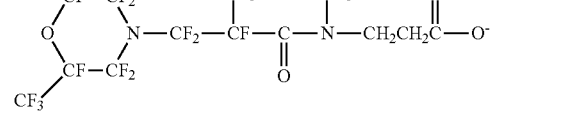 (134)
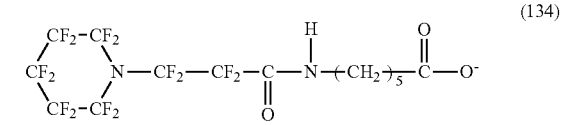 (135)
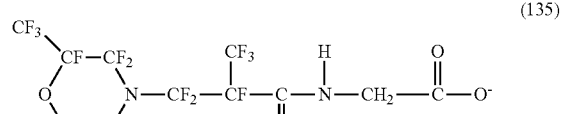 (136)
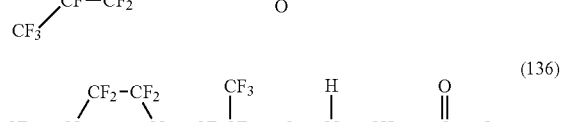 (137)

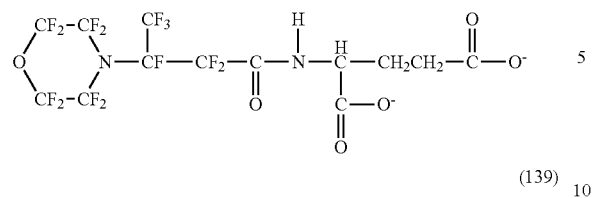
(138)
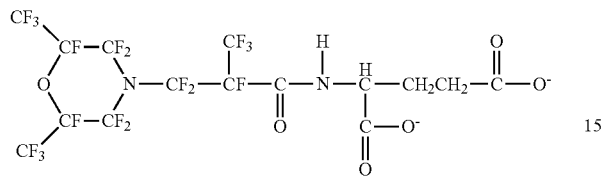
(139)
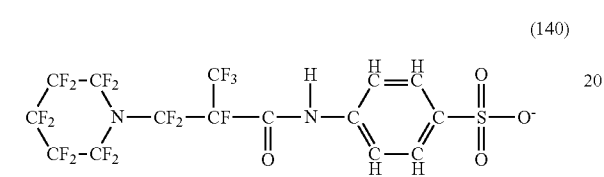
(140)
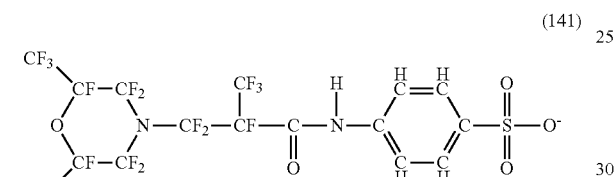
(141)
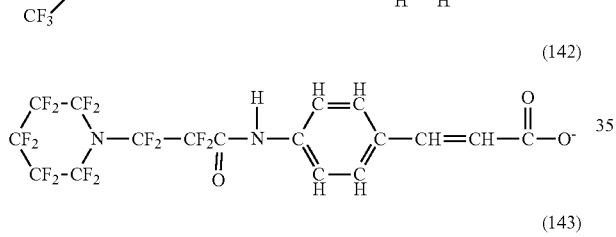
(142)
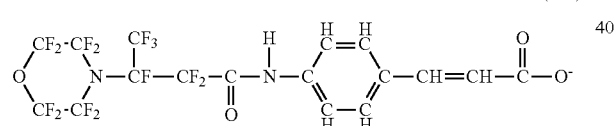
(143)
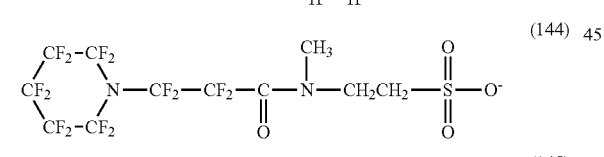
(144)
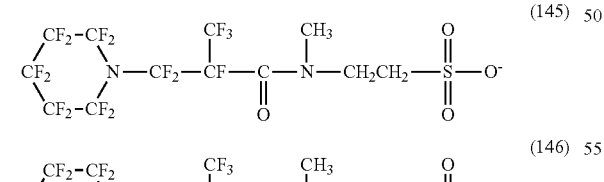
(145)
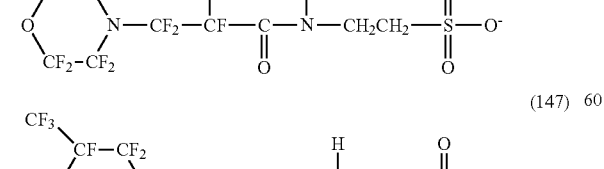
(146)
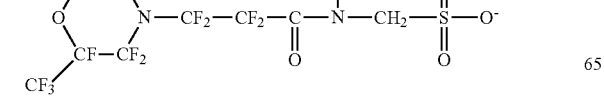
(147)
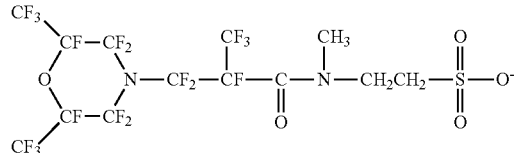
(148)
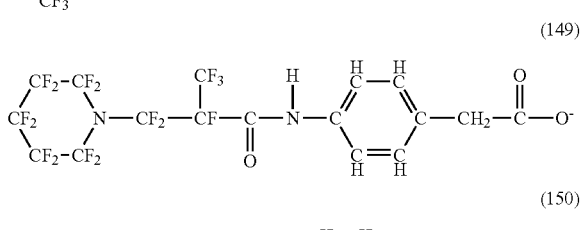
(149)
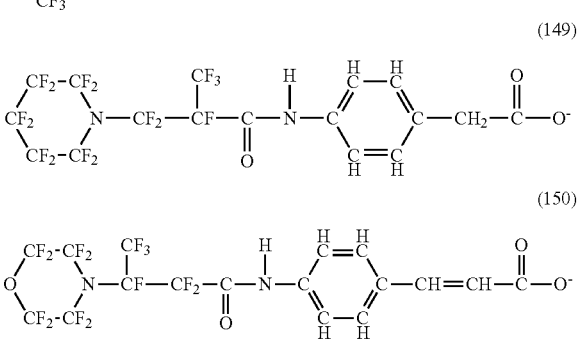
(150)
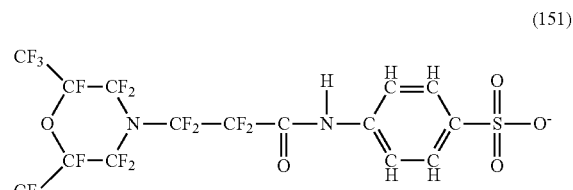
(151)
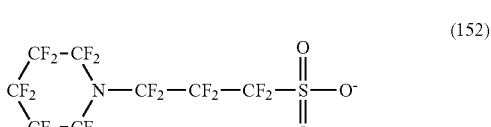
(152)
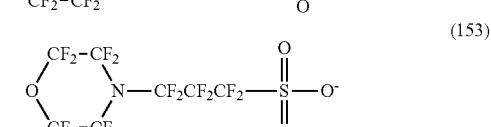
(153)
(154)
(155)
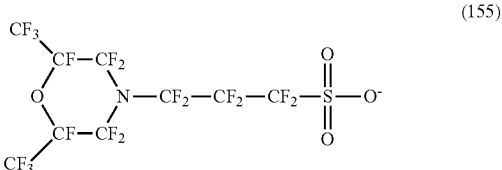
(156)
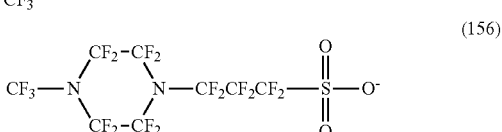
(157)
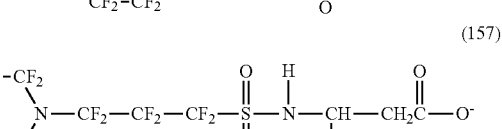
(158)
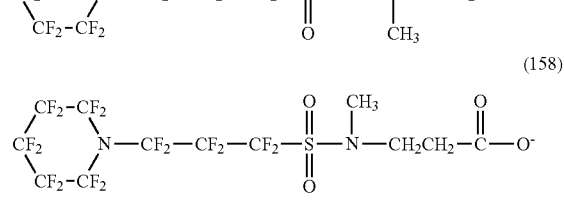

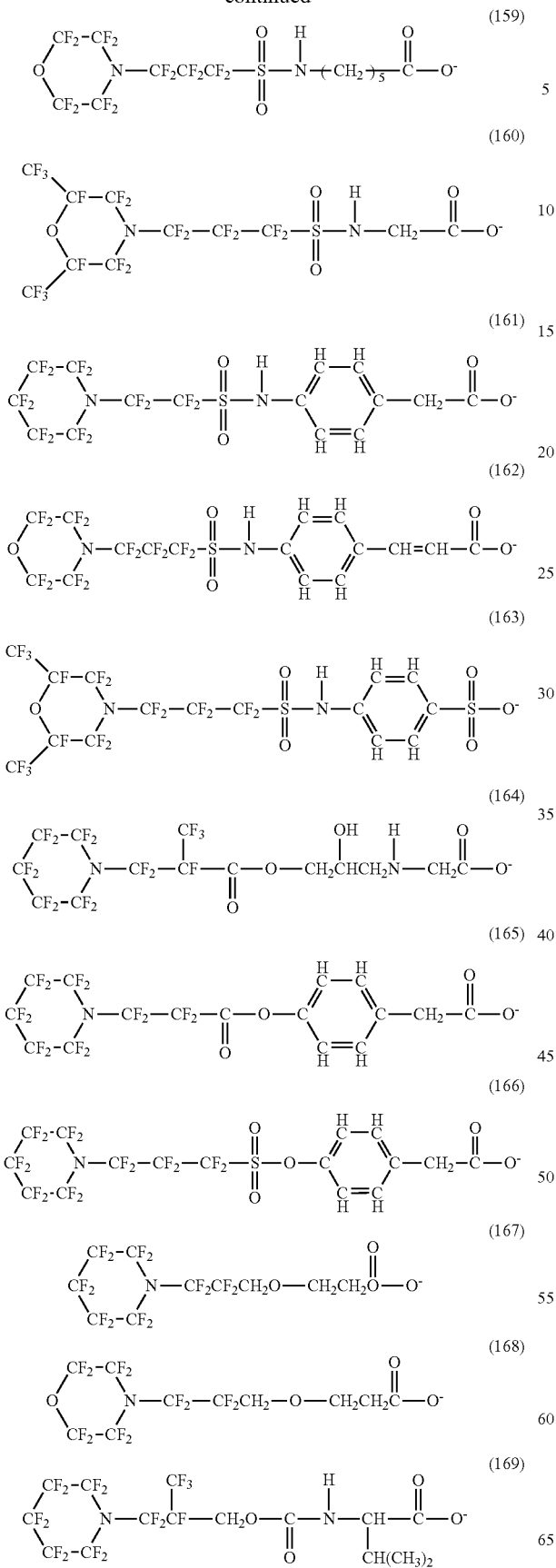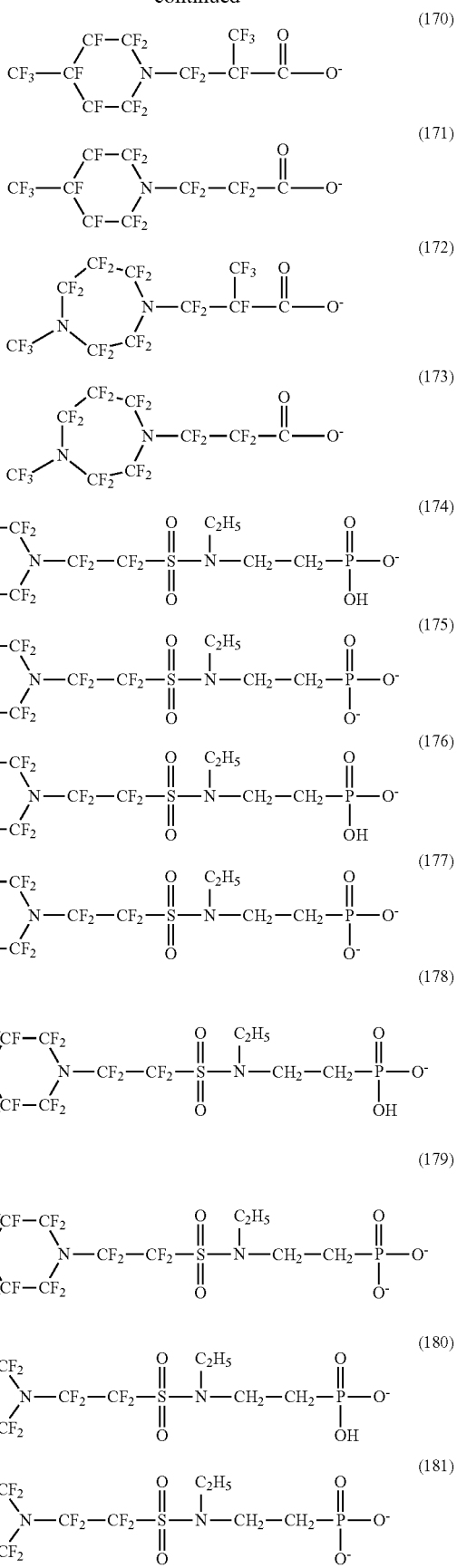

-continued

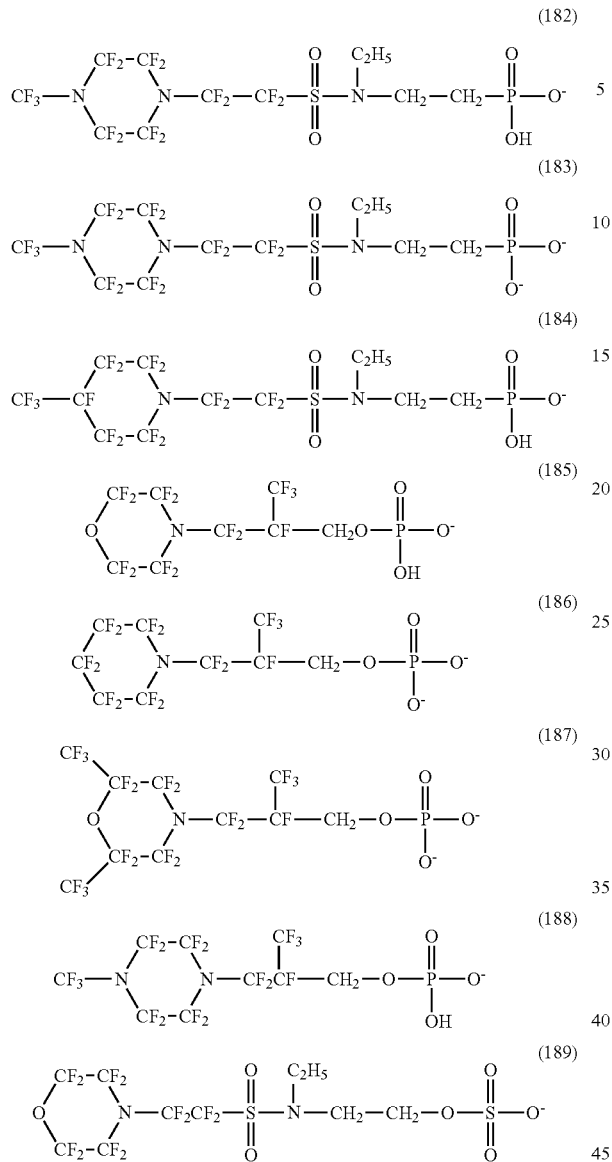

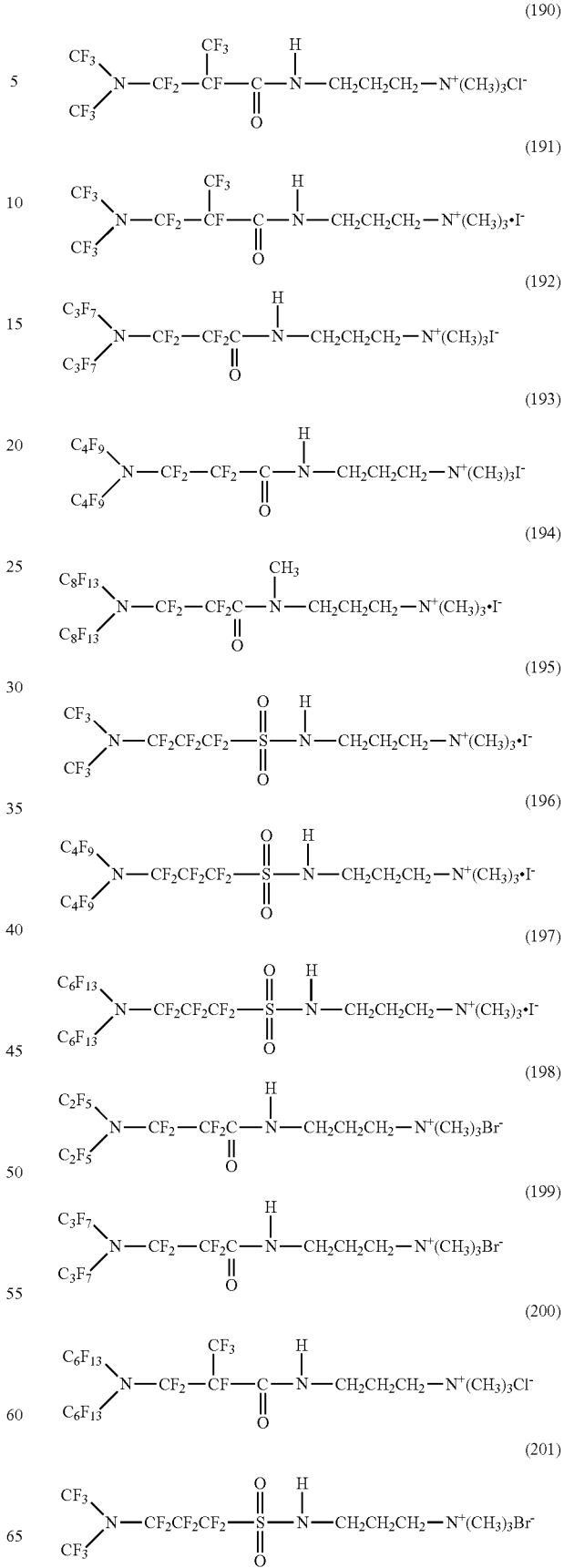

(Cation Type)

In a case where the hydrophilicity imparting group X is a cation type, X has "—N$^+$R$^5$R$^6$R$^7$.Cl$^-$", "—N$^+$R$^5$R$^6$R$^7$.Br$^-$", "—N$^+$R$^5$R$^6$R$^7$.I$^-$", "—N$^+$R$^5$R$^6$R$^7$.CH$_3$SO$_3^-$", "—N$^+$R$^5$R$^6$R$^7$.R$^7$SO$_4^-$", "—N$^+$R$^5$R$^6$R$^7$.NO$_3^-$", "(—N$^+$R$^5$R$^6$R$^7$)$_2$CO$_3^{2-}$", or "(—N$^+$R$^5$R$^6$R$^7$)$_2$SO$_4^{2-}$" (R$^5$ to R$^7$ are each independently a hydrogen atom or a linear or branched alkyl group having 1 to 20 carbon atoms, and preferably having 1 to 10 carbon atoms) at the terminal. Here, if the number of carbon atoms is 20 or less, since the hydrophilicity and oil repellency are not impaired, this is preferable.

Here, in a case where the hydrophilicity imparting group X is a cation type, specific examples of the structure of the hydrophilic oil repellent represented by the formula (1) or (2) (that is, a linear nitrogen-containing fluorine-based compound) include structures of the following formulas (190) to (223).

(202)
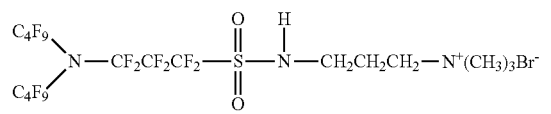
(203)
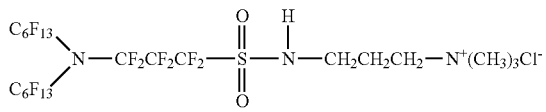
(204)
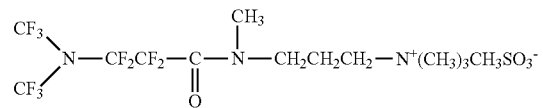
(205)
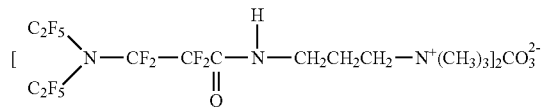
(206)
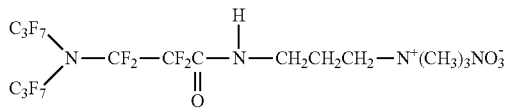
(207)
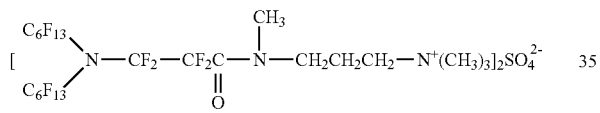
(208)
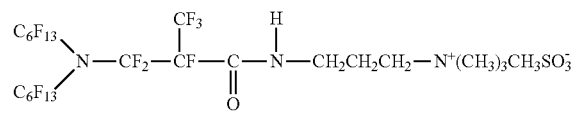
(209)
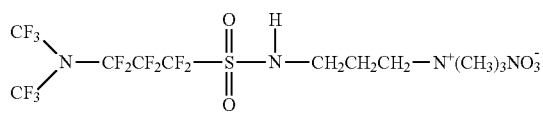
(210)
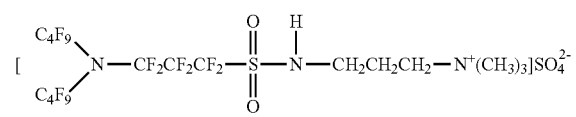
(211)
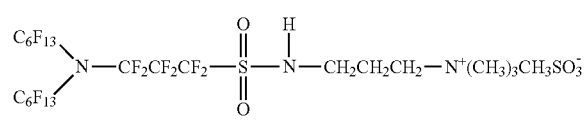
(212)
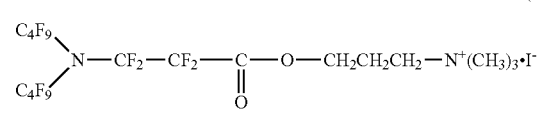
(213)
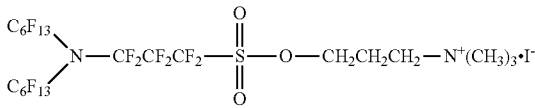
(214)
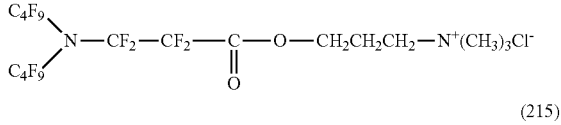
(215)
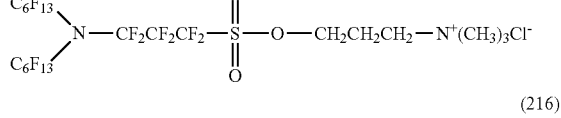
(216)
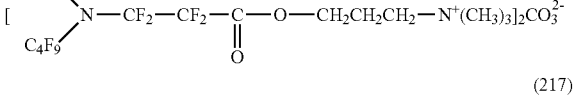
(217)
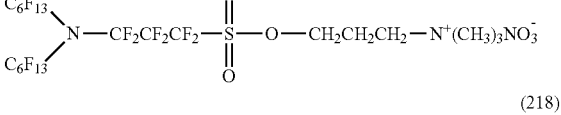
(218)
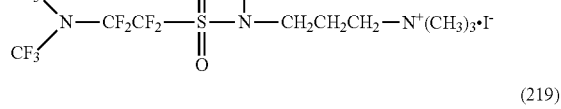
(219)
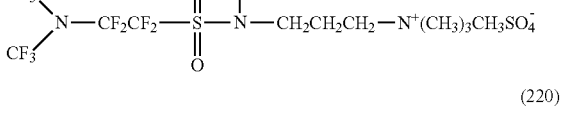
(220)
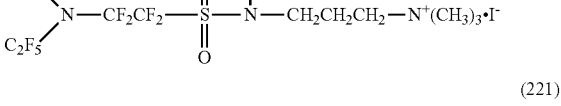
(221)
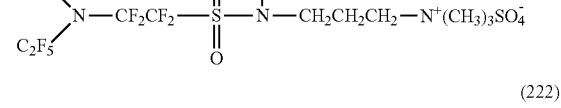
(222)
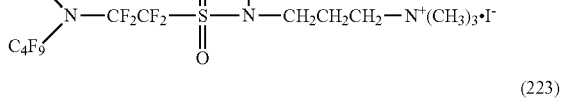
(223)
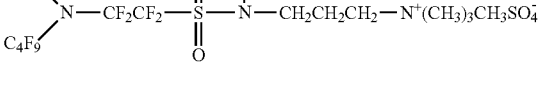
In contrast, specific examples of the structure of the hydrophilic oil repellent represented by the formula (3) or (4) (that is, a cyclic nitrogen-containing fluorine-based compound) include structures of the following formulas (224) to (258).
(224)
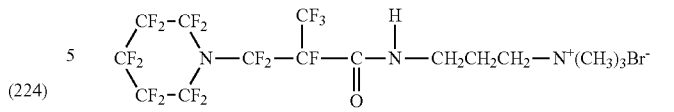
(225)
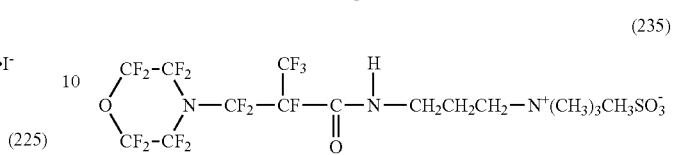
(226)
(227)
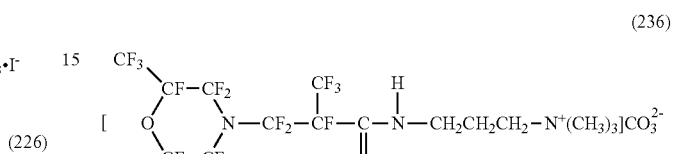
(228)
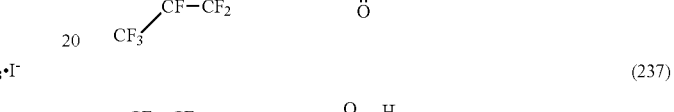
(229)
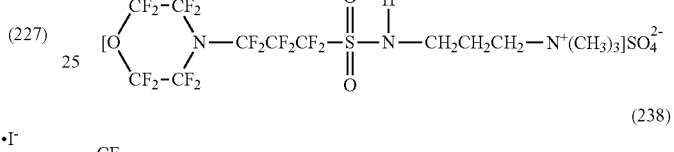
(230)
(231)
(232)
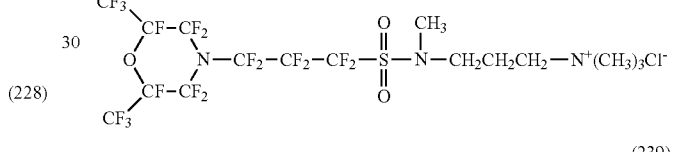
(233)
-continued
(234)
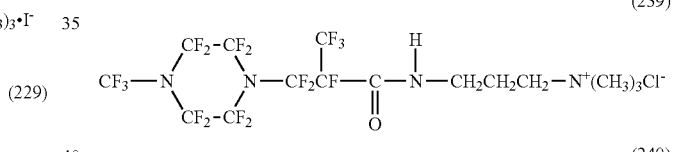
(235)
(236)
(237)
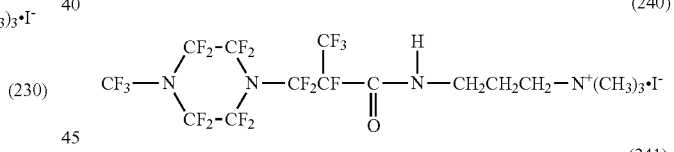
(238)
(239)
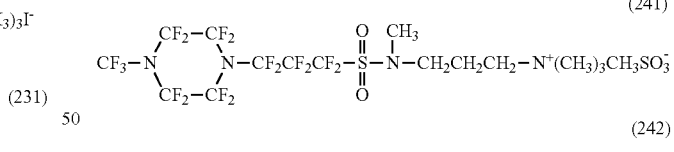
(240)
(241)
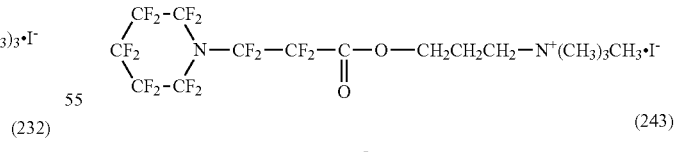
(242)
(243)
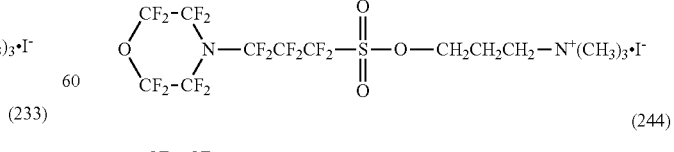
(244)
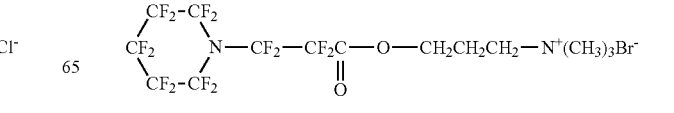

(245) 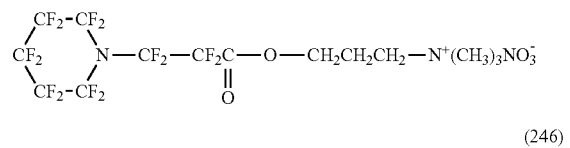

(246) 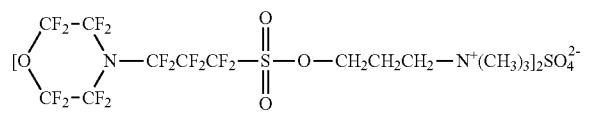

(247) 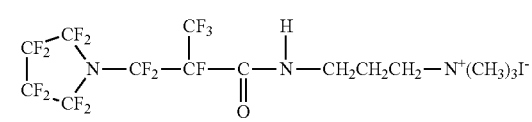

(248)

(249)

(250)

(251)

(252)

(253)

(254)

(255) 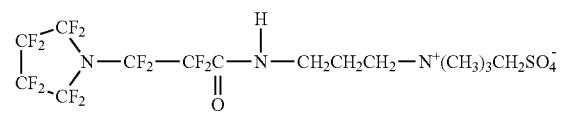

(256) 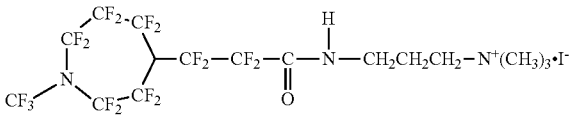

(257) 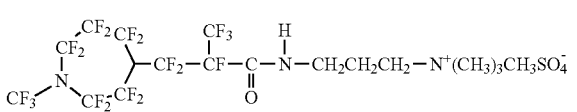

(258) 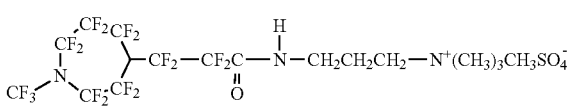

(Amphoteric Type)

In a case where the hydrophilicity imparting group X is an amphoteric type, X has a carboxy betaine type "$-N^+R^8R^9(CH_2)_nCO_2^-$", a sulfobetaine type "$-N^+R^8R^9(CH_2)_nSO_3^-$", an amine oxide type "$-N^+R^8R^9O^-$", or Phosphobetaine type "$-OPO_3^-(CH_2)_nN^+R^8R^9R^{10}$" (n is an integer of 1 to 5, $R^8$ and $R^9$ are hydrogen atoms or alkyl groups having 1 to 10 carbon atoms, and $R^{10}$ is a hydrogen atom or an alkyl group having 1 to 10 carbon atoms or an alkylene group having 1 to 10 carbon atoms) at the terminal. Here, if the number of carbon atoms is 10 or less, since the hydrophilicity and oil repellency is not impaired, this is preferable.

Here, in a case where the hydrophilicity imparting group X is an amphoteric type, specific examples of the structure of the hydrophilic oil repellent represented by the formula (1) or (2) (that is, a linear nitrogen-containing fluorine-based compound) include structures of the following formulas (259) to (309).

(259) 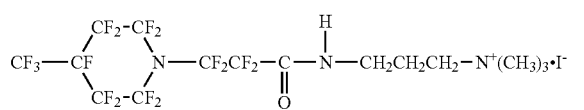

(260)

(261)

(262)

(263) 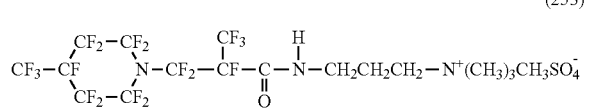

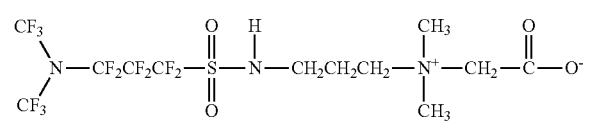
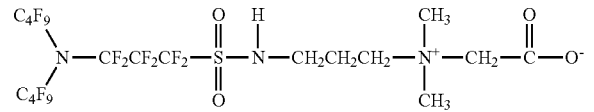
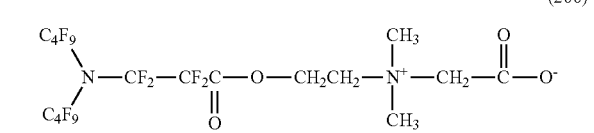
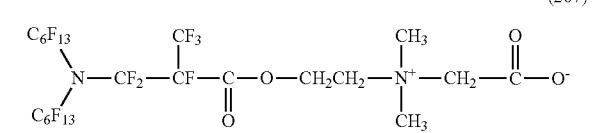
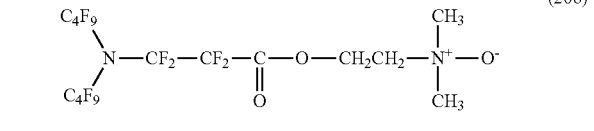
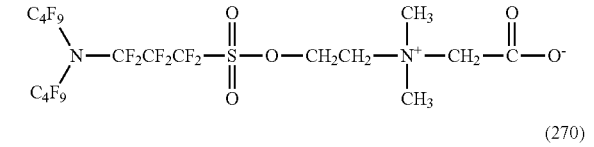
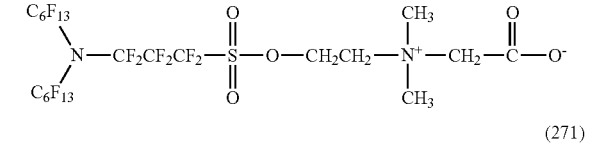
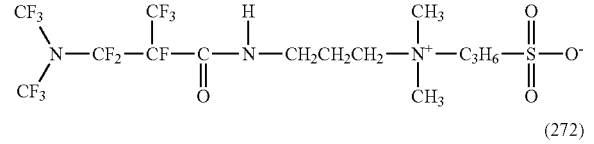
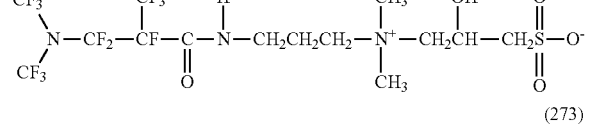
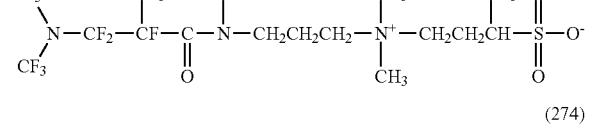
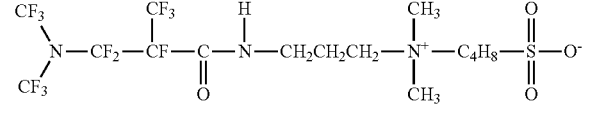

(286) 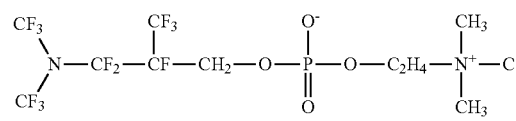
(287) 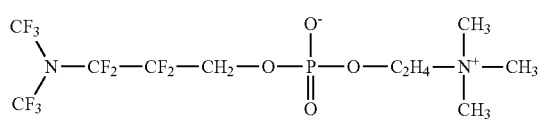
(288) 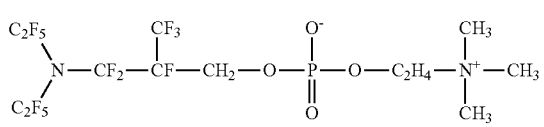
(289) 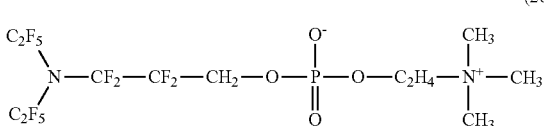
(290) 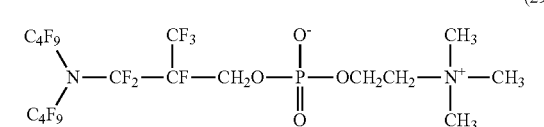
(291) 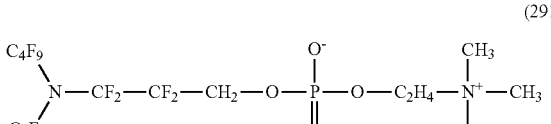
(292) 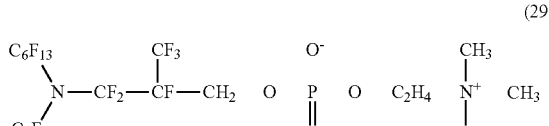
(293) 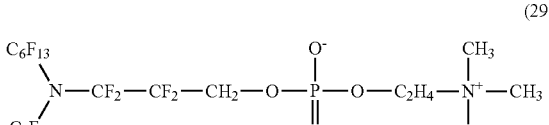
(294) 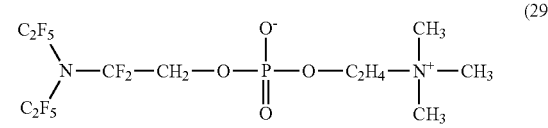
(295) 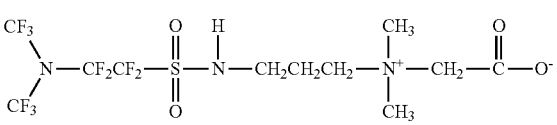
(296) 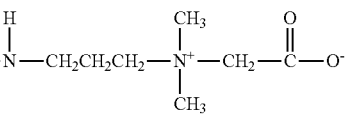
(297) 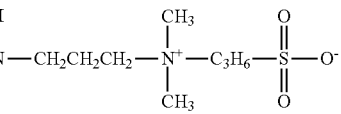
(298) 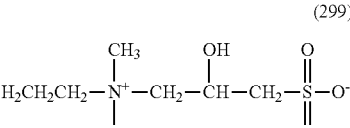
(299) 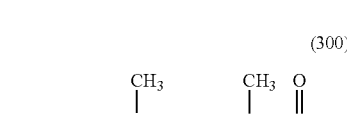
(300) 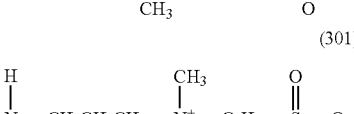
(301) 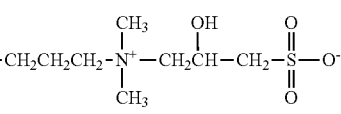
(302) 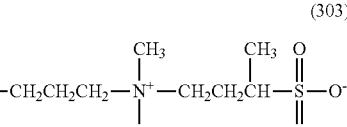
(303) 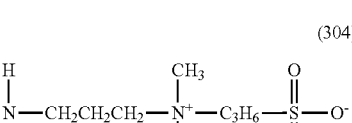
(304) 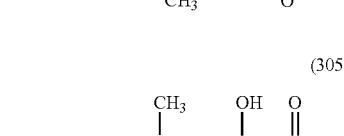
(305) 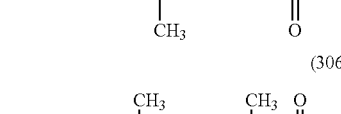
(306) 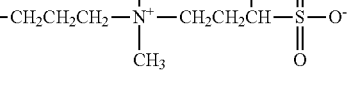

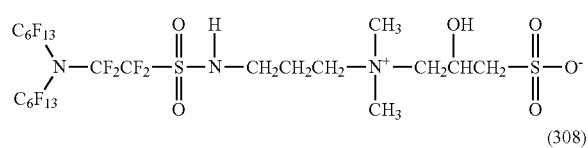
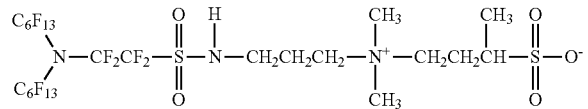
In contrast, specific examples of the structure of the hydrophilic oil repellent represented by the formula (3) or (4) (that is, a cyclic nitrogen-containing fluorine-based compound) include structures of the following formulas (310) to (375).
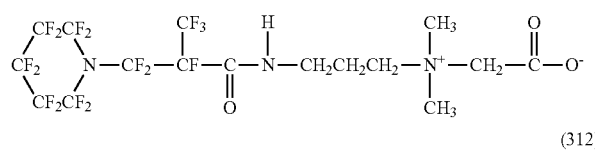
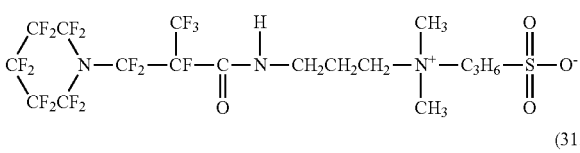
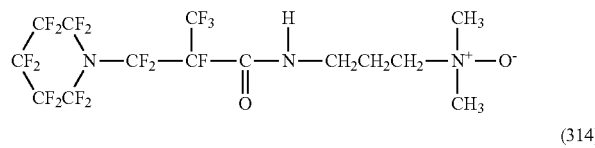
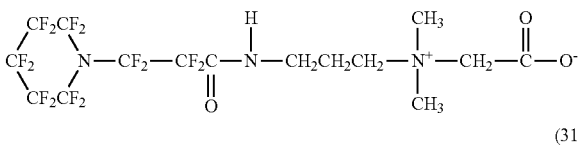
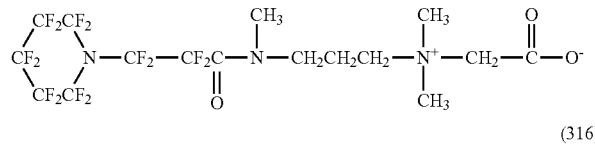
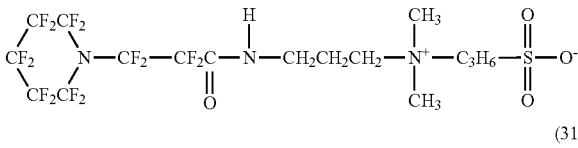
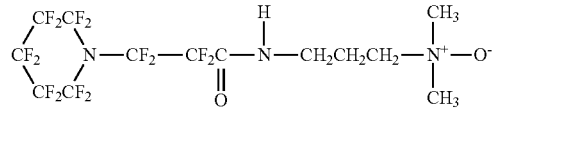
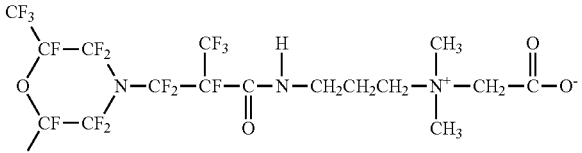
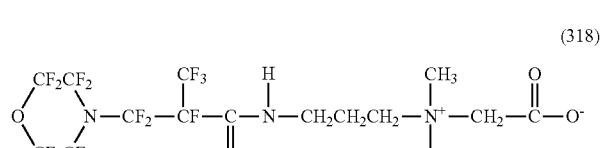
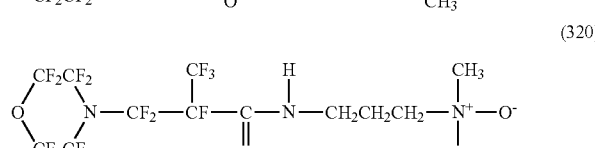
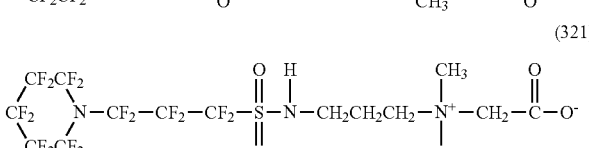
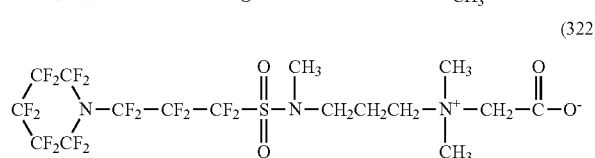
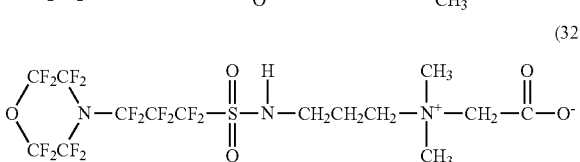
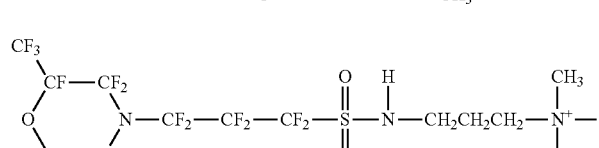

-continued
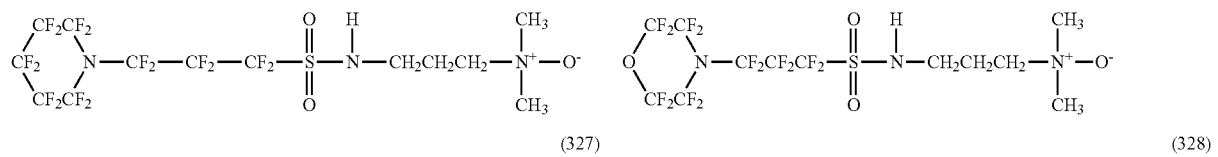
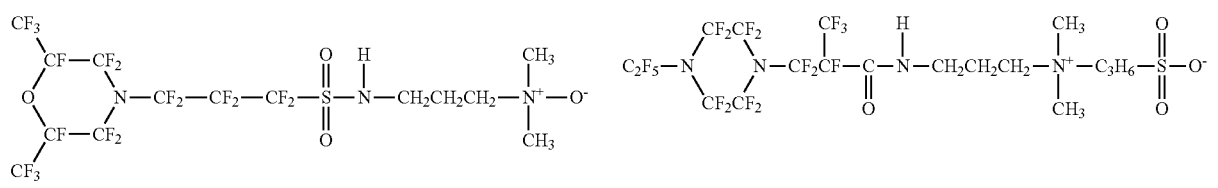
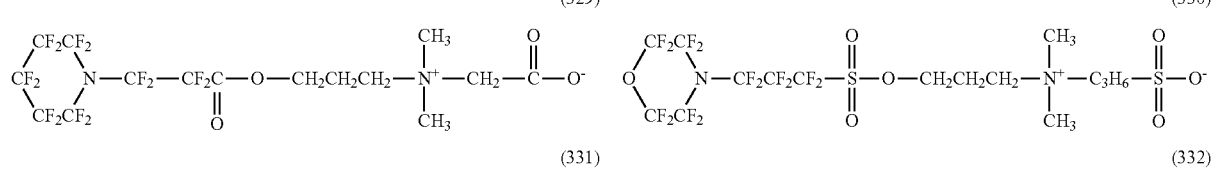
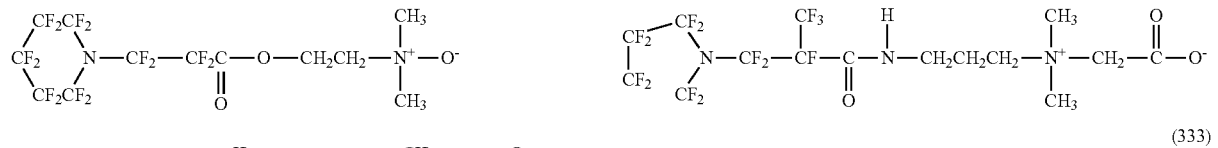
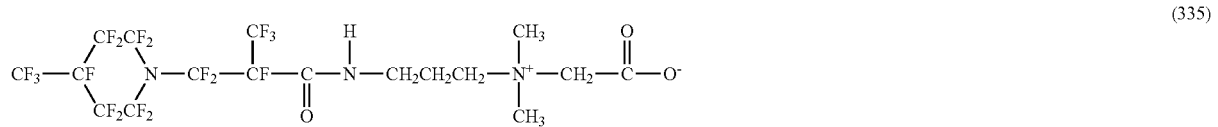
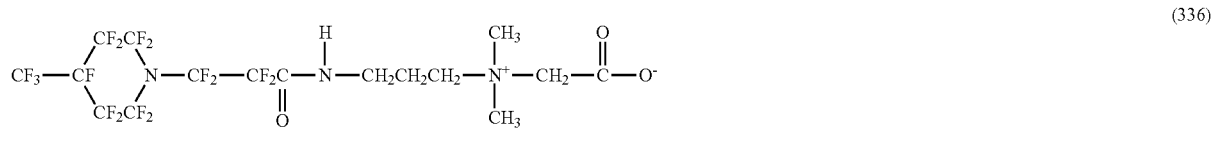
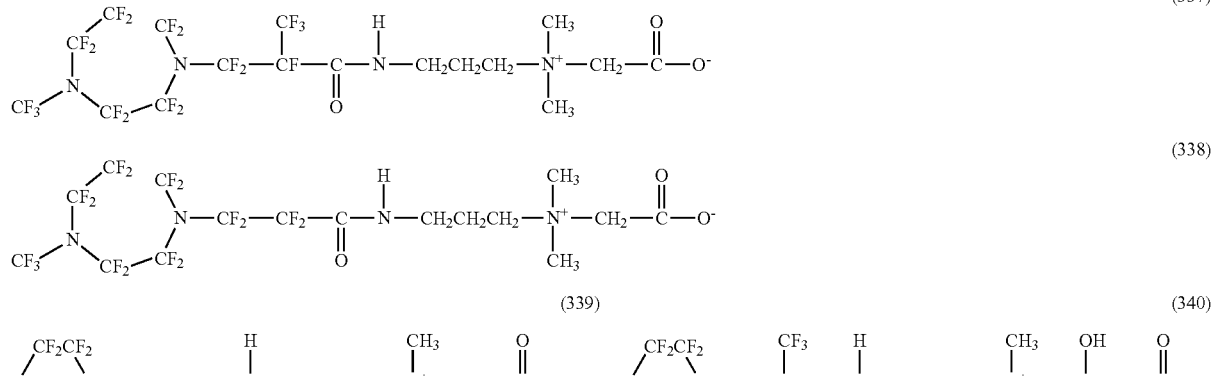

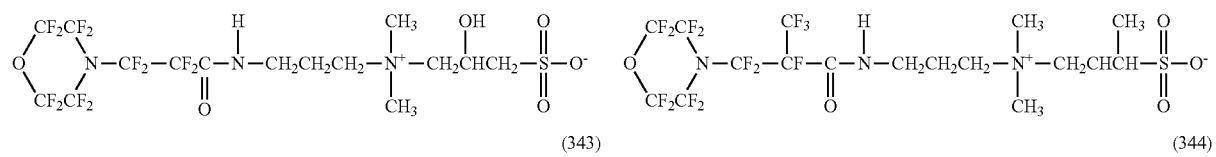
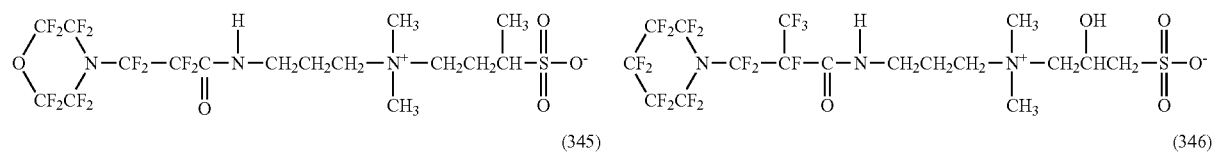
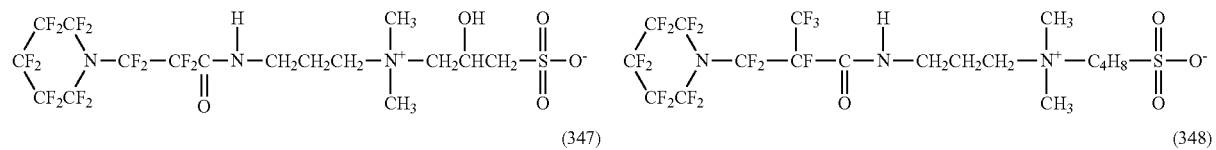
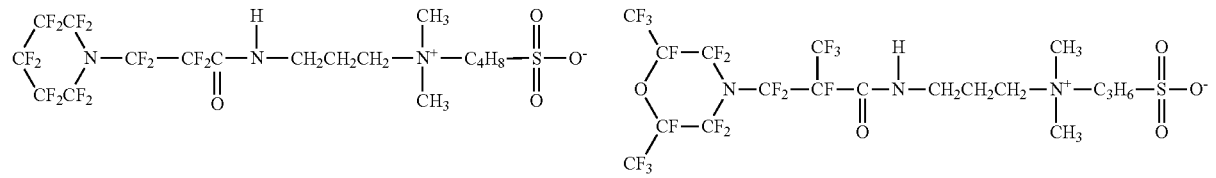
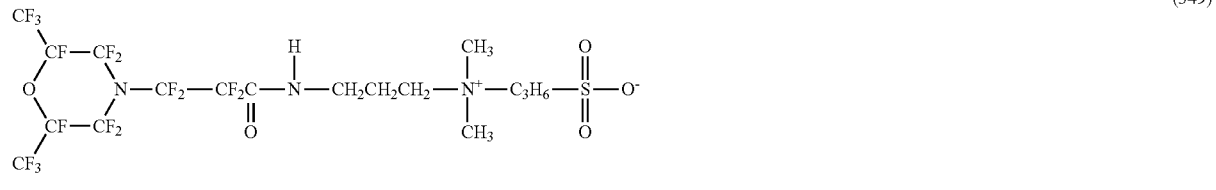
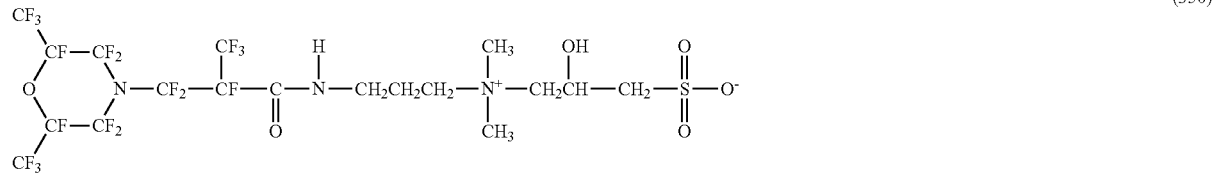
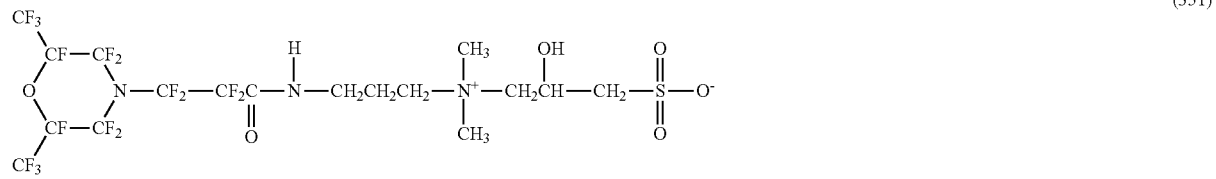
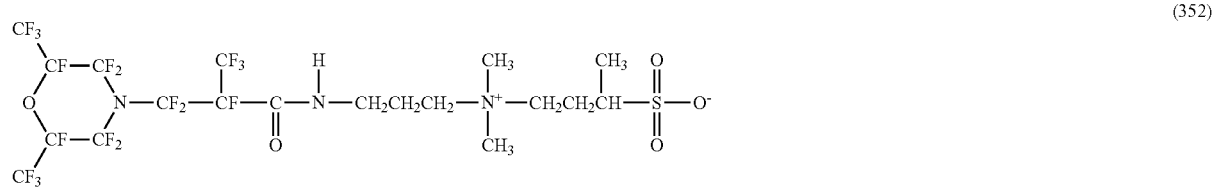
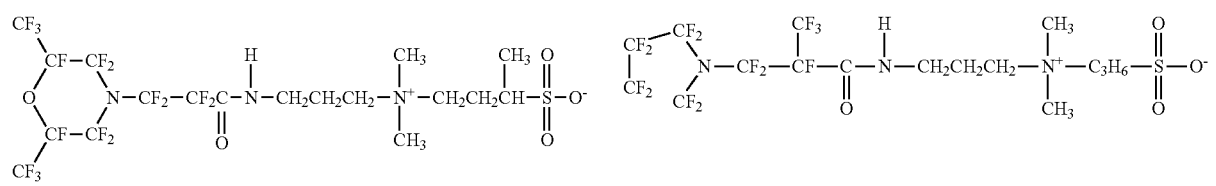

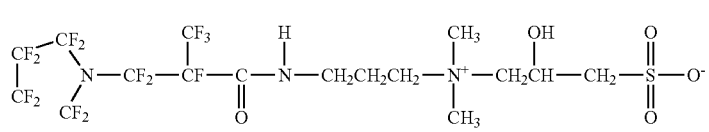
(355)
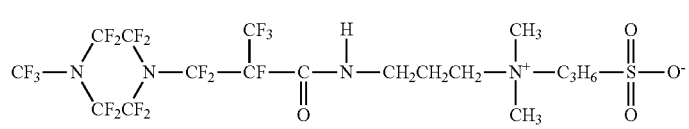
(356)
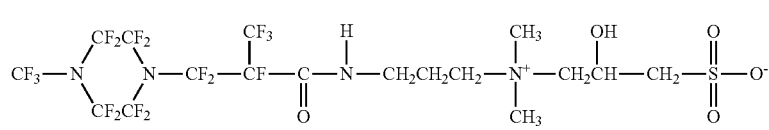
(357)
(358) 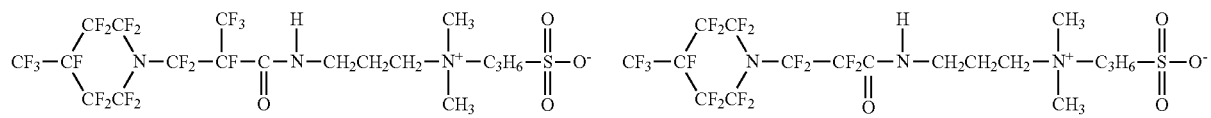 (359)
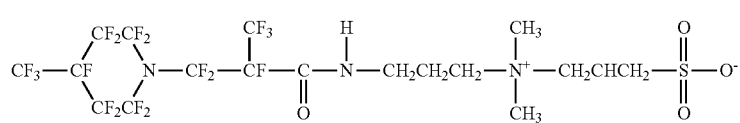
(360)
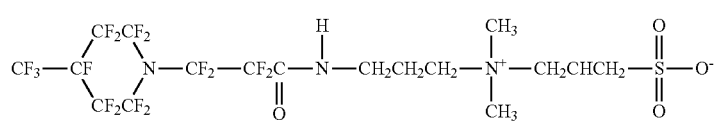
(361)
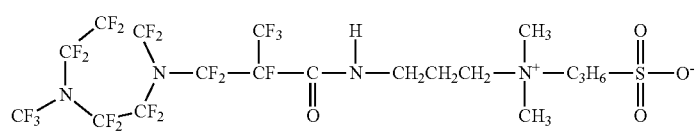
(362)
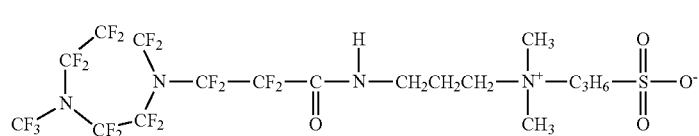
(363)
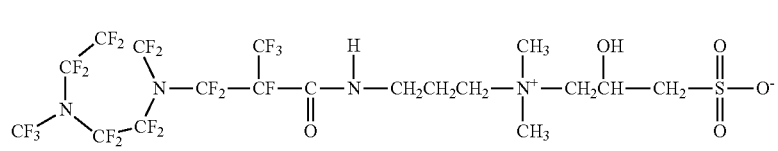
(364)
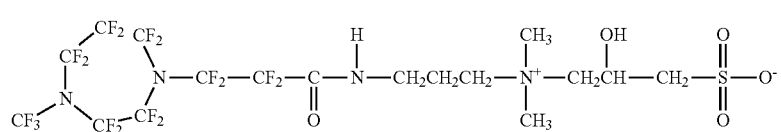
(365)
(366) 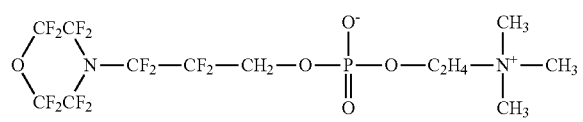 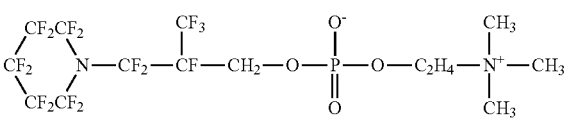 (367)

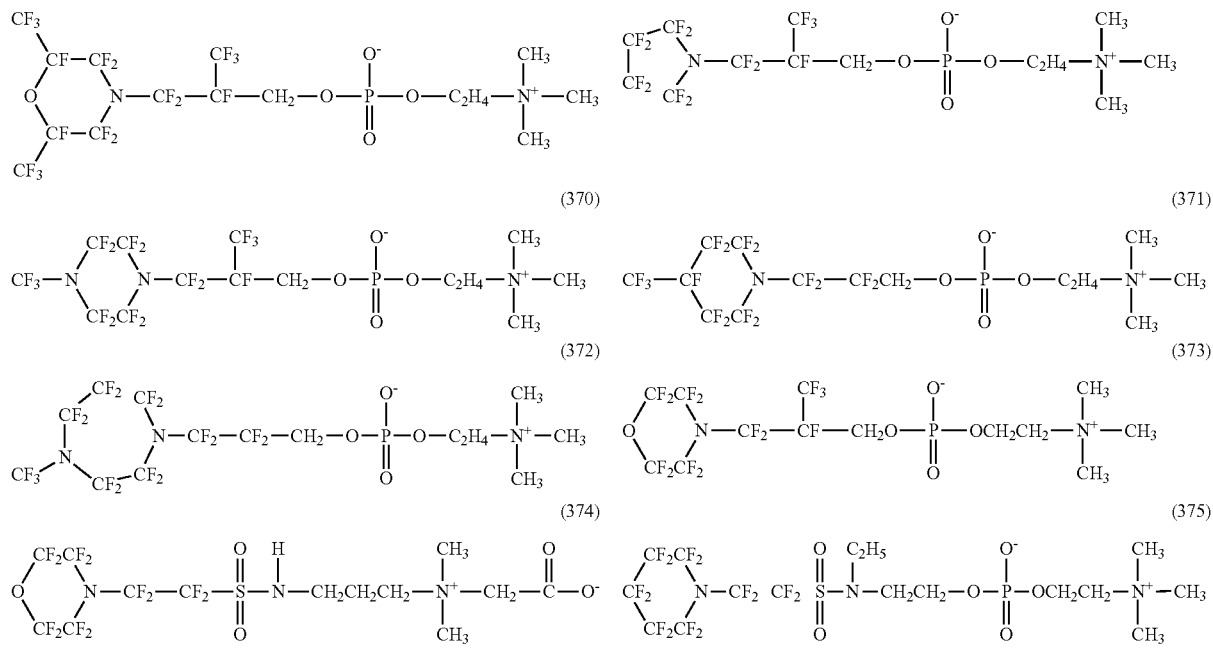

The specific examples of the structure of the hydrophilic oil repellent of the present embodiment described above are simply examples, and the technical scope of the present invention is not limited to the above specific examples. That is, the hydrophilic oil repellent of the present embodiment may have at least one or more oil repellency imparting groups formed of a nitrogen-containing perfluoroalkyl group and at least one or more hydrophilicity imparting groups of any types of an anion type, a cation type, and an amphoteric type, in the molecule.

In addition, the hydrophilic oil repellent of the present embodiment described above sufficiently exhibits hydrophilicity and oil repellency by itself, but, since in the practical environment, acid, alkali, oil, and the like are included, there are many differences, and thus, in the case of considering practical durability, it is desirable to increase the durability against the practical environment by suitably combining hydrophilic oil repellents.

To the hydrophilic oil repellent of the present invention, various modifications can be added in a range not departing from the scope of the present invention. For example, in the specific examples of the structure of the hydrophilic oil repellent of the present embodiment described above, as an oil repellency imparting group formed of a nitrogen-containing perfluoroalkyl group, a case where $Rf^1$ and $Rf^2$ shown in the formulas (1) and (2) are symmetric has been described, but the present invention is not limited thereto, and $R^{f1}$ and $R^{f2}$ may be asymmetric.

In addition, the hydrophilic oil repellent of the present embodiment may have two or more same or different oil repellency imparting groups in the molecule. Furthermore, in the case of having two or more oil repellency imparting groups in the molecule, the oil repellency imparting groups may be provided at both terminals of the molecule or may be provided in the molecular chain.

In addition, the hydrophilic oil repellent of the present embodiment may have two or more same or different hydrophilicity imparting groups in the molecule.

In addition, the hydrophilic oil repellent of the present embodiment may have two or more same or different bonds in the linking group. Furthermore, in a case where the linking group is a polymer type, the repeat number and the bonding order of unit are not particularly limited.

Next, the evaluation method of hydrophilicity and oil repellency of the nitrogen-containing fluorine-based compound represented by each of the formulas (1) to (4) will be described. Here, evaluation of the hydrophilicity and oil repellency, specifically, can be performed by a contact angle measurement or a filter penetration test.

In the contact angle measurement (droplet method), first, the nitrogen-containing fluorine-based compound represented by each of the above formulas (1) to (4) is dissolved in methanol to obtain a methanol solution. Next, after a soda glass plate has been immersed in a 1 N potassium hydroxide aqueous solution at room temperature for 2 hours in advance, the soda glass plate is washed with pure water and washed with acetone, and dried. The soda glass plate is immersed (dip coated) in the methanol solution, then, the methanol is removed by drying at room temperature, whereby a coating film is formed on the glass plate. Next, water and n-hexadecane are dropped onto the coating film, and the contact angle between the coating film and the droplet is measured at room temperature (22±1° C.), respectively. As a result of the contact angle measurement, in a case where the contact angle of water to the coating film is 20° or less and the contact angle of n-hexadecane is 40° or greater, it is assumed that the nitrogen-containing fluorine-based compound has hydrophilicity and oil repellency (that is, the nitrogen-containing fluorine-based compound is a hydrophilic oil repellent).

On the other hand, in the filter penetration test, first, the nitrogen-containing fluorine-based compound represented by each of the above formulas (1) to (4) is dissolved in a solvent such as water or an alcohol to obtain a solution, then, a commercially available PTFE membrane filter (ADVAN- TEC T 100 A 047 A: pore size of 1 μm, porosity of 79%, thickness of 75 μm) was dip in the solution, and water and n-hexadecane are respectively dropped onto the filter obtained by drying at room temperature. After dropping, in a case where water does not penetrate the filter within 5 minutes and n-hexadecane does not penetrate the filter even after 30 minutes, by visual determination, it is assumed that the nitrogen-containing fluorine-based compound has hydrophilicity and oil repellency (that is, the nitrogen-containing fluorine-based compound is a hydrophilic oil repellent). For the untreated PTFE membrane filter, water does not penetrate the filter even after 30 minutes and n-hexadecane permeates the filter within 5 minutes (that is, hydrophobic and lipophilic).

In the contact angle measurement and the filter penetration test, the dropping method of water and n-hexadecane is performed using the following conditions.
(Contact Angle Measurement)
Dropping volume: 2 μL/drop (water)
Dropping volume: 2 μL/drop (n-hexadecan)
Measurement temperature: room temperature (22±1° C.)
(Filter Penetration Test)
Dropping volume: 40 to 45 μL/drop (water)
Dropping volume: 20 to 25 μL/drop (n-hexadecane)
Dropping height: 5 cm from the surface of a PTFE membrane filter
Dropping jig: polyspuit
Measurement temperature: room temperature (22±1° C.)
<Production Method of Hydrophilic Oil Repellent>

Next, the production method of a hydrophilic oil repellent of the present embodiment will be described.

In the production method of a hydrophilic oil repellent of the present embodiment, the nitrogen-containing fluorine-based compound represented by each of the above formulas (1) to (4) is produced using a carboxylic acid halide or a sulfonic acid halide having a nitrogen-containing perfluoroalkyl group represented by the following formula (5) or (6) as a raw material. Specifically, the nitrogen-containing fluorine-based compound represented by the formula (1) or (2) is produced using a carboxylic acid halide or a sulfonic acid halide having a nitrogen-containing perfluoroalkyl group represented by the following formula (5) as a raw material. In addition, the nitrogen-containing fluorine-based compound represented by the formula (3) or (4) is produced using a carboxylic acid halide or a sulfonic acid halide having a nitrogen-containing perfluoroalkyl group represented by the following formula (6) as a raw material.

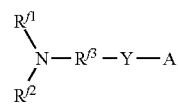

(5)

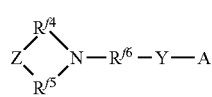

(6)

Here, in the above formula (5), $Rf^1$ and $Rf^2$ each represent a linear or branched perfluoroalkyl group having 1 to 6 carbon atoms, which are the same as or different from each other. In addition, $Rf^3$ represents a linear or branched perfluoroalkylene group having 1 to 6 carbon atoms.

$Rf^1$ and $Rf^2$ each preferably represent a linear or branched perfluoroalkyl group having 1 to 4 carbon atoms, which are the same as or different from each other. In addition, $Rf^3$ preferably represents a linear or branched perfluoroalkylene group having 1 to 4 carbon atoms.

In addition, in the above formula (6), $Rf^4$, $Rf^5$, and $Rf^6$ each represent a linear or branched perfluoroalkylene group having 1 to 6 carbon atoms, which are the same as or different from each other.

$Rf^4$, $Rf^5$, and $Rf^6$ each preferably represent a linear or branched perfluoroalkylene group having 1 to 4 carbon atoms, which are the same as or different from each other.

In addition, Z includes any one of an oxygen atom, a nitrogen atom, a $CF_2$ group, and a CF group. In addition, in a case where Z includes a nitrogen atom or a CF group, a perfluoroalkyl group branched from Z may be bonded to Z.

In addition, in the above formulas (5) and (6), Y is CO or $SO_2$.

Furthermore, in the above formulas (5) and (6), A is any one halogen atom selected from the group consisting of fluorine, chlorine, bromine, and iodine.

The production method of a hydrophilic oil repellent of the present embodiment is a production method different depending on the type of X shown in the above formulas (1) to (4). The cases will be explained separately below.

(Case of Anion Type)

First, a case of producing a nitrogen-containing fluorine-based compound shown in the above formula (1) or (3) will be described.

Among the raw materials shown in the above formula (5) or (6), in a case where Y is CO (in the case of being carboxylic acid-based), the raw material is added dropwise to the aqueously solubilized $M(OH)_m$ (M is Li, Na, K, Ca, Mg, Al, or the like, m is 1 in the case of a monovalent cation such as Li, Na, or K, m is 2 in the case of a divalent cation such as Ca or Mg, and m is 3 in case of a trivalent cation such as Al) and in a case where Y is $SO_2$ (in the case of being sulfonic acid-based), the raw material is added dropwise to the aqueously solubilized $M(OH)_m$ (M is Li, Na, K, $R^1R^2R^3R^4N^+$, Ca, Mg, Al, or the like, m is 1 in case of a monovalent cation such as Li, Na, or K, m is 2 in the case of a divalent cation such as Ca or Mg, m is 3 in case of a trivalent cation such as Al, and $R^1$ to $R^4$ are hydrogen atoms or each independently a linear or branched alkyl group having 1 to 20 carbon atoms) to perform a neutralization reaction, and the resulting product is solidified by drying. The objective substance is extracted from the obtained solid by performing dry solidification using a solvent in which the objective substance is soluble and M(A), $M(A)_2$, or $M(A)_3$ which is a by-product is insoluble, then, by further performing dry solidification on this extraction solvent, the objective substance can be obtained. If necessary, this salt can be converted to carboxylic acid or sulfonic acid using an acid such as sulfuric acid, and by making a desired salt using $M(OH)_m$ again after distillation, the salt can be purified.

Next, a case of producing a nitrogen-containing fluorine-based compound shown in the above formula (2) or (4) will be described.

Specifically, for example, in the case of introducing a linking group R having an amide bond between an oil repellency imparting group (nitrogen-containing perfluoroalkyl group) and an anion type hydrophilicity imparting group, first, by reacting a nitrogen-containing perfluoroalkylcarbonyl fluoride or a sulfonyl fluoride with an aminoalkylcarboxylic acid or aminophenylsulfonic acid and then reacting with alkali hydroxide, an alkali metal salt of a carboxylic acid or sulfonic acid having an amide bond is obtained.

In addition, for example, in the case of introducing a linking group R having an ester bond between an oil repellency imparting group (nitrogen-containing perfluoroalkyl group) and an anion type hydrophilicity imparting group, first, by reacting a nitrogen-containing perfluoroalkylcarbonyl fluoride or a sulfonyl fluoride with a hydroxyphenyl organic acid and then reacting with alkali hydroxide, an alkali metal salt of a carboxylic acid or sulfonic acid having an ester bond is obtained.

In addition, for example, in the case of introducing a linking group R having an ether bond between an oil repellency imparting group (nitrogen-containing perfluoroalkyl group) and an anion type hydrophilicity imparting group, first, nitrogen-containing perfluoroalkylcarbonyl fluoride is reduced with lithium aluminum hydride ($LiAlH_4$) or sodium borohydride ($NaBH_4$) to produce an alcohol having a nitrogen-containing perfluoroalkyl group. Next, the alcohol is converted to potassium alcoholate with t-butoxypotassium or the like, and then by reacting with a metal salt of a halogenated organic acid, an alkali metal salt of a carboxylic acid having an ether bond is obtained.

(Case of Cation Type)

Specifically, for example, among the raw materials shown in the above formula (5) or (6), nitrogen-containing perfluoroalkylcarbonyl fluoride or sulfonyl fluoride is amide-bonded with N,N-dialkylaminoalkyleneamine to give a terminal tertiary amine, and by performing quaternization with an alkylating agent such as methyl iodide ($CH_3I$), methyl bromide ($CH_3Br$), or dimethyl sulfate (($CH_3$)$_2SO_4$), a nitrogen-containing fluorine-based compound having a cation type hydrophilicity imparting group is obtained.

In addition, for example, among the raw materials shown in the above formula (5) or (6), nitrogen-containing perfluoroalkylcarbonyl fluoride or sulfonyl fluoride is ether-bonded with N,N-dialkylaminoalkylene alcohol to give a terminal tertiary amine, and by performing quaternization with an alkylating agent such as methyl iodide ($CH_3I$), methyl bromide ($CH_3Br$), or dimethyl sulfate (($CH_3$)$_2SO_4$), a nitrogen-containing fluorine-based compound having a cation type hydrophilicity imparting group is obtained.

(Case of Amphoteric Type)

Specifically, for example, in the case of a carboxybetaine type, first, among the raw materials shown in the above formula (5) or (6), nitrogen-containing perfluoroalkylcarbonyl fluoride or sulfonyl fluoride is amide-bonded with N,N-dialkylaminoalkyleneamine or ether-bonded with N,N-dialkylaminoalkylene alcohol to give a terminal tertiary amine, and by reacting with sodium monochloroacetate, a nitrogen-containing fluorine-based compound having an amphoteric type hydrophilicity imparting group is obtained.

In addition, for example, in the case of a sulfobetaine type, after making a terminal tertiary amine as described above, by reacting this with a cyclic sulfonic acid ester compound represented by 1,3-propane sultone or the like, a nitrogen-containing fluorine-based compound having an amphoteric type hydrophilicity imparting group is obtained.

In addition, for example, in the case of an amine oxide type, after making a terminal tertiary amine as described above, by reacting this with hydrogen peroxide, a nitrogen-containing fluorine-based compound having an amphoteric type hydrophilicity imparting group is obtained.

In addition, for example, in the case of a phosphobetaine type, by reacting an alcohol form obtained by reducing nitrogen-containing perfluorocarbonyl fluoride or one obtained by introducing a hydroxyl group at the terminal by sulfonamidating nitrogen-containing perfluoroalkylsulfonyl fluoride with an amino alcohol, with, for example, phosphorus oxychloride in the presence of a base such as trimethylamine, a dichlorophosphoric acid ester having a nitrogen-containing perfluoroalkyl group is obtained. Next, by reacting the obtained dichlorophosphoric acid ester having a nitrogen-containing perfluoroalkyl group with bromoethanol and then reacting trimethylamine in the presence of a silver carbonate catalyst, a quaternary ammonium salt is obtained, and finally, by performing hydrolysis, a nitrogen-containing fluorine-based compound having an amphoteric type hydrophilicity imparting group is obtained.

<Surface Coating Material>

By containing the above-described hydrophilic oil repellent of the present embodiment in a solvent, it is possible to form a surface coating material of the hydrophilic oil repellent. Here, examples of the solvent include water, an organic solvent, and a mixture of water and an organic solvent. In addition, examples of the organic solvent include methanol, ethanol, IPA, tetrahydrofuran, hexane, chloroform, toluene, ethyl acetate, DMSO, DMF, acetone, and a fluorine-based solvent. In particular, from the viewpoint of ease of drying, ease of use, and environmental effects, water or alcohols such as methanol, ethanol, and IPA, or a mixture of water and alcohol is preferable. In addition, it is also possible to mix a solvent compatible with these solvents. Examples thereof include ether-based solvents such as tetrahydrofuran, aliphatic hydrocarbon-based solvents such as hexane, halogenated hydrocarbon-based solvents such as chloroform, aromatic hydrocarbon-based solvents such as toluene, ester-based solvents such as ethyl acetate, ketone-based solvents such as acetone, and fluorine-based solvents such as hexafluoroxylene.

Here, in the surface coating material, the mass composition ratio between a hydrophilic oil repellent and a solvent is preferably within a range of 0.2 to 50:99.8 to 50, more preferably within a range of 1 to 20:99 to 80, and still more preferably within a range of 2 to 10:98 to 90. If the mass composition ratio of the hydrophilic oil repellent in the surface coating material is 0.2 or greater, when treated, since it is possible to sufficiently render hydrophilicity and oil repellency to the entirety of the substrate, this is preferable. On the other hand, if the mass composition ratio of the hydrophilic oil repellent in the surface coating material is 50 or less, since the solution dispersion stability of the surface coating material is excellent, this is preferable. In consideration of coatability and durability of products, the mass composition ratio between the hydrophilic oil repellent in the surface coating material and the solvent is preferably within a range of 2 to 10:98 to 90.

In addition, a binder is preferably added to the surface coating material. Thus, it is possible to enhance adhesion to a substrate. In addition, since, by enclosing the hydrophilic oil repellent, a binder has a function of reducing the area in contact with the environment of the hydrophilic oil repellent itself, it is possible to improve the sustainability durability of the characteristics.

Specific examples of the binder include a resin or an inorganic glass. Examples of the resin include a thermoplastic resin, a thermoplastic elastomer, a thermosetting resin, a UV curable resin, and specific examples thereof include thermoplastic resins such as polyvinyl chloride, polyethylene, polypropylene, polycarbonate, polyester, polystyrene, a silicone resin, polyvinyl acetal, polyvinyl alcohol, an acrylic polyol-based resin, a polyester polyol-based resin, a urethane resin, a fluororesin, and a thermoplastic acrylic resin, and thermosetting resins such as an epoxy resin, a phenol resin, and a thermosetting acrylic resin.

Furthermore, to exhibit the characteristics of hydrophilicity and oil repellency at the maximum, hydrophilic polymers are preferably used as a binder. In addition, among the hydrophilic polymers, a hydrophilic polymer containing a hydroxyl group which bring about adhesion to the substrate or interaction such as a hydrogen bond with a hydrophilic oil repellent composite is preferable.

Specific examples of the hydrophilic polymer include polysaccharides such as polyvinyl alcohol, polyvinyl butyral, and cellulose, and derivatives thereof. These may be used alone or in combination of two or more types thereof. The hydrophilic polymer may be crosslinked with a crosslinking agent. By such crosslinking, the durability of paint is improved.

The crosslinking agent is not particularly limited, and can be suitably selected depending on the purpose. Specific examples thereof include an epoxy compound, an isocyanate compound, an aldehyde compound, an ultraviolet crosslinking type compound, a leaving group-containing compound, a carboxylic acid compound, and a urea compound.

Specific examples of the inorganic glass include silane compounds such as a trialkoxysilane represented by the chemical formula $[R^{14}Si(OR^{15})_3]$ and a tetraalkoxysilane represented by the chemical formula $[Si(OR^{16})_4]$ ($R^{14}$ to $R^{16}$ are each independently an alkyl group having 1 to 6 carbon atoms), and water glass. Among these, since water glass has a high durability improving effect, this is preferable.

In the surface coating material, the mass composition ratio between a hydrophilic oil repellent and a binder is preferably within a range of 0.2 to 99.9:99.8 to 0.1, more preferably within a range of 2 to 98:98 to 2, and still more preferably within a range of 10 to 90:90 to 10. If the mass composition ratio of the hydrophilic oil repellent is 0.2 or greater, since the hydrophilicity and oil repellency is sufficiently obtained, this is preferable.

The mixing method for forming the surface coating material is not particularly limited as long as it is a method in which the hydrophilic oil repellent can be dispersed or dissolved in a solvent, such as a ball mill, a roll mill, a sand mill, a paint shaker, a homogenizer, an impeller type stirrer, an ultrasonic disperser, or a magnetic stirrer.

In addition to the hydrophilic oil repellent, the solvent, and the binder, to impart functions other than the hydrophilicity and oil repellency of a pigment, a conductivity imparting agent, or a leveling agent, the surface coating material may further include an additive as an optional component.

<Coating Film>

By using the surface coating material described above, at least a part of the surface of the substrate can be coated with the coating film. There is a case where the coating film is formed of only a hydrophilic oil repellent, and there is a case where the coating film includes a binder. In a case where a binder is included in the coating film, the mass composition ratio between the hydrophilic oil repellent and the binder is preferably within a range of 0.2 to 99.9:99.8 to 0.1. Here, if the mass composition ratio of the hydrophilic oil repellent is 0.2 or greater, since sufficient hydrophilicity and oil repellency is obtained, this is preferable. In consideration of the adhesion to the substrate and the durability of the coating film, the mass composition ratio is more preferably within a range of 2 to 98:98 to 2, and particularly preferably within a range of 10 to 90:90 to 10.

As a forming method of the coating film, specifically, for example, by the above-described surface coating material is applied to at least a part of the surface of the substrate and by performing a drying treatment for removing the solvent, it is possible to form a coating film on at least a part of the surface of the substrate.

The substrate is not particularly limited, and glass, plastic, metal, ceramics, stainless steel, aluminum, wood, stone, cement, concrete, fiber, cloth, paper, leather, a combination thereof, a structure thereof, or a laminate thereof can be used.

In the application step, the method of applying to the surface of a substrate is not particularly limited. Specific example thereof includes a dipping method of dipping a substrate in a surface coating material and a method using application means such as a spray, a brush, or a roller, or using a printing method.

In the forming step, although the conditions of the drying treatment of the coating film vary depending on the type and content of the solvent included in the surface coating material, for example, drying at room temperature for 1 to 24 hours, or drying by heating to an extent that the substrate is not influenced is an exemplary example.

<Resin Composition>

The hydrophilic oil repellent of the present embodiment described above can be used as an additive for imparting a function of hydrophilicity and oil repellency to various resins.

Examples of the resin include a thermoplastic resin, a thermoplastic elastomer, a thermosetting resin, a UV curable resin. The resin is not particularly limited as long as it is a resin in which the hydrophilic oil repellent can be dispersed and dissolved. Specific examples of such a resin include thermoplastic resins such as polyvinyl chloride, polyethylene, polypropylene, polycarbonate, polyester, polystyrene, a silicone resin, polyvinyl acetal, polyvinyl alcohol, an acrylic polyol-based resin, a polyester polyol-based resin, a urethane resin, a fluororesin, and a thermoplastic acrylic resin, and thermosetting resins such as an epoxy resin, a phenol resin, and a thermosetting acrylic resin.

Furthermore, to exhibit the characteristics of hydrophilicity and oil repellency at the maximum, hydrophilic polymers are preferably used as a resin. As the hydrophilic polymer, a hydrophilic polymer containing a hydroxyl group is preferable. Specific examples thereof include polysaccharides such as polyvinyl alcohol, polyvinyl butyral, and cellulose, and derivatives thereof. These may be used alone or in combination of two or more types thereof. In addition, the hydrophilic polymer may be crosslinked with a crosslinking agent. By such crosslinking, the durability of a resin composition is improved.

The crosslinking agent is not particularly limited, and can be suitably selected depending on the purpose. Specific examples thereof include an epoxy compound, an isocyanate compound, an aldehyde compound an ultraviolet crosslinking type compound, a leaving group-containing compound, a carboxylic acid compound, and a urea compound.

In addition to the hydrophilic oil repellent and the resin, the resin composition may further include an additive to impart functions other than the hydrophilicity and oil repellency, such as a fluidity improver, a surfactant, a flame retardant, a conductivity imparting agent, and a fungicide.

The forming method of the resin composition is not particularly limited as long as it is a method in which the hydrophilic oil repellent suitably selected according to the type of resin can be dispersed or dissolved. Specifically, for example, as the method of mixing the hydrophilic oil repellent with a thermoplastic resin, there is a method of mixing by kneading by an extrusion method or a roll method.

The resin composition can be further processed into a resin molded product. Specific examples thereof include injection molded products such as a film, a sheet, a thread, and a casing.

In the resin composition, the mass composition ratio between a hydrophilic oil repellent and a resin is preferably within a range of 0.2 to 99.9:99.8 to 0.1, more preferably within a range of 2 to 98:98 to 2, and still more preferably within a range of 10 to 90:90 to 10. If the mass composition ratio of the hydrophilic oil repellent is 0.2 or greater, since a hydrophilicity and oil repellency function can be sufficiently exhibited, this is preferable. If the mass composition ratio of the hydrophilic oil repellent is 90 or less, since moldability is easily maintained without deteriorating the physical properties of the resin, this is preferable.

Examples of the applications of the coating film and the resin composition described above include applications to a member to which quick drying properties are expected, such as water, a member to which antifouling effects are expected, and a member to which anti-fogging effects and oil removability are expected.

Examples of more specific applications to which quick drying properties are expected, such as water include building materials, building exterior such as an outer wall and a roof, building interior, a window frame, window glass, exterior and painting of vehicles such as an automobile, a railway vehicle, an aircraft, a ship, a bicycle, and a motorcycle, exterior of the machinery and the articles, a dust cover and painting, a signboard, a traffic sign, various display devices, an advertising tower, a soundproof wall for road, a soundproof wall for railway, a bridge, exterior and painting of guardrail, tunnel interior and painting, an insulator, a solar cell cover, a solar heat water heater heat collection cover, a heat radiation fin for heat exchanger, a vinyl house, a cover for vehicular lamp, housing facilities, a toilet bowl, a bathtub, a wash stand, lighting equipment, a lighting cover, kitchen utensils, dishes, a dish washer, a dish dryer, a sink, a cooking range, a kitchen hood, a ventilating fan, and a film to be adhered to the surfaces of the above-described articles.

Examples of more specific applications to which antifouling effects are expected include building exterior such as an outer wall and a roof, building interior, a window frame, window glass, in building materials, a signboard, a traffic sign, a soundproof wall, exterior and painting of vehicles such as an automobile, a railway vehicle, an aircraft, a ship, a bicycle, and a motorcycle, exterior of the machinery and the articles, a dust cover and painting, various display devices, an advertising tower, a soundproof wall for road, a soundproof wall for railway, a bridge, exterior and painting of guardrail, tunnel interior and painting, an insulator, a solar cell cover, a solar heat water heater heat collection cover, a vinyl house, a cover for vehicular lamp, housing facilities, a toilet bowl, a bathtub, a wash stand, lighting equipment, a lighting cover, kitchen utensils, dishes, a dish washer, a dish dryer, a sink, a cooking range, a kitchen hood, and a ventilating fan. In addition, examples of the optical member include a cover glass or a cover sheet of a touch panel, an icon sheet or a screen protection film, and an optical disk. In particular, the optical members have excellent characteristics regarding removability against oil contamination of a dining room or kitchen utensils. Examples of the optical member further include a film to be adhered to the surface of these articles. It can also be applied to roofing materials for snowy countries, antennas, and power transmission lines, and at this time, excellent snow accretion preventing properties are also obtained.

Examples of more specific applications to which anti-fogging effects are expected include glass for automobiles and building materials, mirrors such as a back mirror for vehicles, a bathroom mirror, a toilet mirror, and a road mirror, eyeglass lenses, an optical lens, a camera lens, and a film to be adhered to the surface of these articles.

<Oil-Water Separation Filter Material>

In a case where a mixture of water and oil is allowed to flow to a filter paper, nonwoven fabric, a cartridge filter, or a porous body or a porous film of an inorganic substance or an organic substance, which has been treated with the above-described surface coating material, water passes through the filter or the like, but oil cannot pass through, and thus, it can be used as a hydrophilic oil-repellent separation film or filter (these are collectively referred to as "separation filter material") which can separate oil and water only by gravity. This separating film and filter can be used as an oil-water separation film or an oil-water separation filter (that is, "oil-water separation filter material") which separates water and oil, for example, at the time of oil drilling or recovery of spillage oil.

In addition, since hydrophilicity and oil repellency has been imparted to the oil-water separation filter material described above, organic molecules and soil mud contaminated with oil are less likely to adhere, and thus, excellent fouling resistance is obtained. In addition, since adhered stains are easily removed by a physical treatment such as back pressure washing, the oil-water separation filter material also has excellent cleaning properties.

<Porous Body>

If the hydrophilic oil repellent of the present embodiment is used in a form of a porous body, excellent oil-water separation performance can be obtained, this is preferable.

As a method for obtaining a porous body, a method generally known in the related art can be applied. Specific examples thereof include a method of drying a solution or dispersion of a hydrophilic oil repellent by a spray drying method. The particles obtained in the above manner can be formed into a porous body and controlled in the particle diameter thereof, and can be applied as a filter material without further operation, and thus, the particles are particularly preferable.

In addition, when producing porous particles, by bonding the porous particles by adding a binder such as a resin or a vitreous material to a solution or dispersion of a hydrophilic oil repellent, it is possible to increase or reduce the physical strength of a porous body by controlling the solubility thereof in water.

As the resin, the above-described thermoplastic resin or thermosetting resin can be used, and as the vitreous material, the above-described silane compound or water glass can be used, and the amount of binder used with respect to the hydrophilic oil repellent is not particularly limited as long as the binder is suitably added within a range where the particles can be bonded. Typically, the mass composition ratio between a hydrophilic oil repellent and a binder is preferably used within a range of 0.2 to 99.9:99.8 to 0.1, more preferably used within a range of 2 to 98:98 to 2, and still more preferably used within a range of 10 to 90:90 to 10.

In addition, the hydrophilic oil repellent of the present invention can also be supported on other porous bodies. As the supporting porous body, clay minerals such as silica, alumina, zeolite, calcium carbonate, talc, and montmorillonite can be used. As the method of supporting, a method in which a supporting porous body is added to a solution or dispersion of a hydrophilic oil repellent and the solvent is removed by drying can be applied. As the ratio of supporting, it is preferable that the mass composition ratio between the hydrophilic oil repellent and the supporting porous body is selected from a range of 1:99 to 50:50 from the viewpoint of hydrophilic oil repellent characteristics.

By fixing the obtained porous particles onto the surface of a substrate such as a filter paper, nonwoven fabric, or a cartridge filter, excellent oil-water separation performance can be obtained, and thus, this is more preferable. In addition, for fixing to a substrate, it is possible to use the above-described resin or vitreous material.

As described above, the hydrophilic oil repellent of the present embodiment is a compound including an oil repellency imparting group formed of a nitrogen-containing perfluoroalkyl group and any one of an anion type hydrophilicity imparting group, a cation type hydrophilicity imparting group, and an amphoteric type hydrophilicity imparting group in the molecule, and is a material having excellent hydrophilicity and oil repellency, and thus, the hydrophilic oil repellent has applicability to a wide variety of applications.

In addition, in the production method of the hydrophilic oil repellent of the present embodiment, a carboxylic acid halide or a sulfonic acid halide having a nitrogen-containing perfluoroalkyl group is used as a raw material, and thus, it is possible to easily synthesize various derivatives.

In addition, the hydrophilic oil repellent of the present embodiment, the surface coating material, the coating film, the resin composition, the oil-water separation filter material, and the porous body including the same, do not contain a perfluoroalkyl group having 8 or more carbon atoms which are continuously bonded, have a chemical structure without concern of generating PFOS or PFOA which becomes a problem in terms of bioaccumulation and environmental adaptability, and can impart excellent hydrophilicity and oil repellency.

The technical scope of the present invention is not limited to the above embodiments, and various modifications are possible without departing from the scope of the present invention.

EXAMPLES

Examples of the invention will be described below together with Comparative Examples. The present invention is not limited to these examples.

Synthesis Example 1

Synthesis of perfluoro(3-dibutylaminopropionic acid) calcium 352 g of a 12.5% (mass percent concentration, and hereinafter, the same is applied) sodium hydroxide aqueous solution was put into a 2 L glass flask, and by adding 837 g of perfluoro(3-dibutylaminopropionic acid) fluoride obtained by electrolytic fluorination of methyl 3-dibutylaminopropionate dropwise thereto, a reaction was performed. After adding dropwise, 500 mL of ethyl acetate was added thereto, and by extraction, perfluoro(3-dibutylaminopropionic acid) sodium was obtained. After the ethyl acetate layer and the water were separated, the ethyl acetate was distilled off using a rotary evaporator, whereby 488 g of perfluoro(3-dibutylaminopropionic acid) sodium was obtained as a pale yellow solid.

Next, 488 g of perfluoro(3-dibutylaminopropionic acid) sodium and 280 g of 95% sulfuric acid were put into a 1 L glass flask, followed by mixing, and distillation was performed under reduced pressure, whereby 436 g of perfluoro (3-dibutylaminopropionic acid) which was a solid at room temperature was obtained (the yield from the sodium salt was 93%).

23.5 g of perfluoro(3-dibutylaminopropionic acid) was neutralized with 1.5 g of calcium hydroxide in a methanol/water mixed solution. The precipitated crystals were separated by filtration, and dried at 100° C., whereby 23.5 g of perfluoro(3-dibutylaminopropionic acid) calcium represented by the following formula (376) was obtained (yield of 97%). The solubility of the present compound in water at room temperature (25° C.) was 2 [g/100 g-H$_2$O].

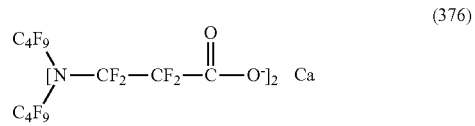

Synthesis Example 2

Synthesis of perfluoro(3-dibutylaminopropionic acid) potassium 10.0 g of perfluoro(3-dibutylaminopropionic acid) obtained in the same manner as in Synthesis Example 1 was neutralized with 2.0 g of a 48% potassium hydroxide aqueous solution in water, and water was distilled off, whereby 10.3 g of perfluoro(3-dibutylaminopropionic acid) potassium represented by the following formula (377) was obtained (yield of 97%).

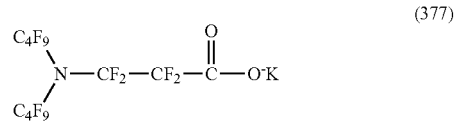

Synthesis Example 3

Synthesis of perfluoro(3-dibutylaminopropionic acid) ammonium 10.0 g of perfluoro(3-dibutylaminopropionic acid) obtained in the same manner as in Synthesis Example 1 was neutralized with 1.0 g of 28% ammonia water in water, and water was distilled off, whereby 10.2 g of perfluoro(3-dibutylaminopropionic acid) ammonium represented by the following formula (378) was obtained (yield of 99%).

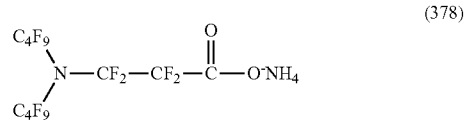

Synthesis Example 4

Synthesis of perfluoro(3-dibutylaminopropionic acid) magnesium 15.0 g of perfluoro(3-dibutylaminopropionic acid) obtained in the same manner as in Synthesis Example 1 was neutralized with 1.2 g of magnesium hydroxide in a methanol/water mixed solution. Next, the precipitated crystals were separated by filtration, and by extracting with methanol, a magnesium salt was obtained. The methanol was distilled off, whereby 14.4 g of perfluoro(3-dibutylaminopropionic acid) magnesium represented by the following formula (379) was obtained (yield of 94%). The solubility of the present compound in water at room temperature was 0.009 [g/100 g-H₂O].

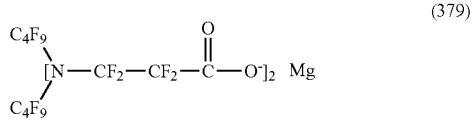

(379)

Synthesis Example 5

Synthesis of perfluoro(3-dibutylaminopropionic acid) barium 15.0 g of perfluoro(3-dibutylaminopropionic acid) obtained in the same manner as in Synthesis Example 1 was neutralized with 4.0 g of barium hydroxide octahydrate in a methanol/water mixed solution. Thereafter, the methanol and the water was distilled off, whereby 15.9 g of perfluoro (3-dibutylaminopropionic acid) barium represented by the following formula (380) was obtained (yield of 94%). The solubility of the present compound in water at room temperature was 0.04 [g/100 g-H₂O].

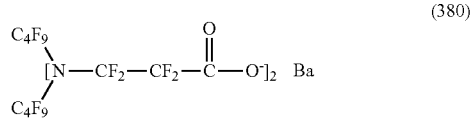

(380)

Synthesis Example 6

Synthesis of perfluoro(3-dipropylaminopropionic acid) potassium

Perfluoro(3-dipropylaminopropionic acid) was obtained in the same manner as in Synthesis Example 1 from perfluoro(3-dipropylaminopropionic acid) fluoride obtained by electrolytic fluorination of methyl 3-dipropylaminopropionate.

Next, 10.0 g of perfluoro(3-dipropylaminopropionic acid) was neutralized with 2.3 g of 48% potassium hydroxide, and water was distilled off, whereby 10.2 g (yield of 95%) of perfluoro(3-dipropylaminopropionic acid) potassium represented by the following formula (381) was obtained.

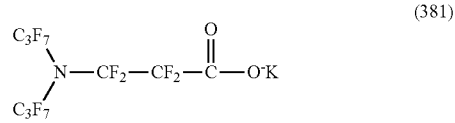

(381)

Synthesis Example 7

Synthesis of perfluoro(3-dipropylaminopropionic acid) ammonium

Perfluoro(3-dipropylaminopropionic acid) was obtained in the same manner as in Synthesis Example 1 from perfluoro(3-dipropylaminopropionic acid) fluoride obtained by electrolytic fluorination of methyl 3-dipropylaminopropionate.

Next, 10.0 g of perfluoro(3-dipropylaminopropionic acid) was neutralized with 1.2 g of a 28% ammonium aqueous solution, and water was distilled off, whereby 9.8 g (yield of 95%) of perfluoro(3-dipropylaminopropionic acid) ammonium represented by the following formula (382) was obtained.

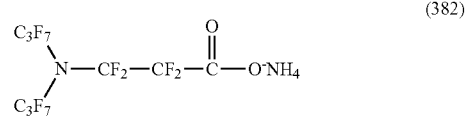

(382)

Synthesis Example 8

Synthesis of perfluoro(2-methyl-3-dimethylaminopropionic acid) calcium

Perfluoro(2-methyl-3-dimethylaminopropionic acid) was obtained in the same manner as in Synthesis Example 1 from perfluoro(2-methyl-3-dimethylaminopropionic acid) fluoride obtained by electrolytic fluorination of methyl 2-methyl-3-dimethylaminopropionate.

Next, 3.0 g of perfluoro(2-methyl-3-dimethylaminopropionic acid) was neutralized with 0.3 g of calcium hydroxide in a methanol/water mixed solution, and the methanol and the water was distilled off, whereby 3.2 g of perfluoro(2-methyl-3-dimethylaminopropionic acid) calcium represented by the following formula (383) was obtained (yield of 99%).

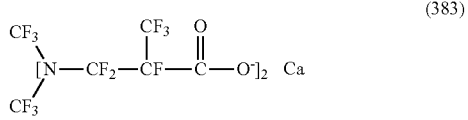

(383)

Synthesis Example 9

Synthesis of 3-[[perfluoro(3-dibutylaminopropanoyl)]amino]propyl-trimethyl-ammonium iodide 10 g of perfluoro(3-dibutylaminopropionic acid) fluoride obtained in the same manner as in Synthesis Example 1 was added dropwise to a solution obtained by dissolving 4 g of dimethylaminopropylamine in 50 ml of an IPE solvent, in an ice bath. After the resulting product was stirred at room temperature for 2 hours, filtration was performed, then, IPE layer of the filtrate was subjected to a washing treatment with an NaHCO₃ aqueous solution and an NaCl aqueous solution, and after liquid-liquid separation was performed, washing with water was performed. Thereafter, the IPE was distilled off, whereby 7 g of $(C_4F_9)_2NC_2F_4CONHC_3H_6N(CH_3)_2$ was obtained as a crude product (yield of 62%).

Next, methyl iodide was added to the obtained crude product in methyl ethyl ketone, and the resulting product was stirred at room temperature overnight. After the reaction ended, collection by filtration was performed, whereby 6 g of a quaternary ammonium iodide represented by the following formula (384) was obtained (yield of 71%).

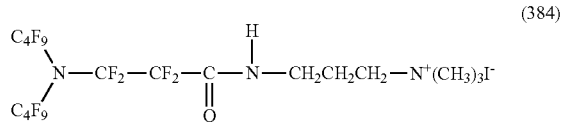

(384)

Synthesis Example 10

Synthesis of 3-[[perfluoro(3-dipropylaminopropanoyl)]amino]propyl-trimethyl-ammonium iodide 14 g of $(C_3F_7)_2NC_2F_4CONHC_3H_6N(CH_3)_2$ was obtained as a crude product in the same manner as in Synthesis Example 9 except that 10 g of perfluoro(3-dibutylaminopropionic acid) fluoride obtained in the same manner as in Synthesis Example 1 was changed to 20 g of perfluoro(3-dipropylaminopropionic acid) fluoride obtained in the same manner as in Synthesis Example 4 (yield of 60%). Next, methyl iodide was added to the obtained crude product in methyl ethyl ketone, and the resulting product was stirred at room temperature overnight. After the reaction ended, collection by filtration was performed, whereby a 13 g of a quaternary ammonium iodide represented by the following formula (385) was obtained (yield of 75%).

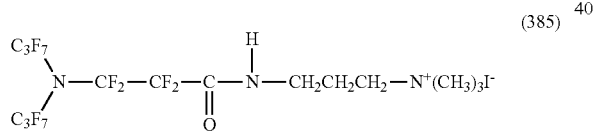

(385)

Synthesis Example 11

Synthesis of 2-[3-[[perfluoro(3-dibutylaminopropanoyl)]amino]propyl-dimethyl-ammonium] acetate 3 g of $(C_4F_9)_2NC_2F_4CONHC_3H_6N(CH_3)_2$ synthesized in the same manner as in Synthesis Example 10 was refluxed overnight with sodium monochloroacetate under stirring in ethanol, whereby 3 g of dimethyl betaine substance represented by the following formula (386) was obtained (yield of 92%).

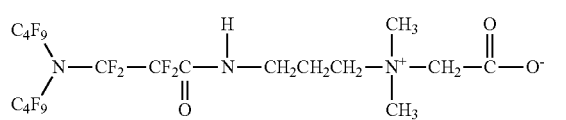

(386)

Synthesis Example 12

Synthesis of 2-[3-[[perfluoro(diethylaminoacetyl)]amino]propyl-trimethyl-ammonium] acetate 10 g of perfluoro(dimethylaminoacetylfluoride) obtained by an electrolytic fluorination of N-(2-hydroxyethyl)dimethylamine was added dropwise to a solution obtained by dissolving 6 g of dimethylaminopropylamine in 50 ml of an IPE solvent, in an ice bath. After the resulting product was stirred at room temperature for 2 hours, filtration was performed, then, the IPE layer of the filtrate was subjected to a washing treatment with an $NaHCO_3$ aqueous solution and an NaCl aqueous solution, and after liquid-liquid separation was performed, washing with water was performed. Thereafter, the IPE was distilled off, and distillation was further performed, whereby 5.6 g of $(C_2F_5)_2NCF_2CONHC_3H_6N(CH_3)_2$ was obtained as a crude product (yield of 45%).

Next, 4 g of $(C_2F_5)_2NCF_2CONHC_3H_6N(CH_3)_2$ obtained above was refluxed overnight with sodium monochloroacetate under stirring in ethanol, and the resulting product was filtered and concentrated, whereby 4.5 g of dimethyl betaine substance represented by the following formula (387) was obtained (yield of 99%).

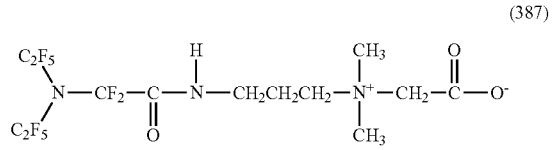

(387)

Synthesis Example 13

Synthesis of 2-[3-[perfluoro(3-dibutylaminopropanoyl)]oxypropyl-dimethyl-ammonium] acetate 20 g of perfluoro(3-dibutylaminopropionic acid) fluoride obtained by electrolytic fluorination of methyl 3-dibutylaminopropionate was added dropwise to a solution obtained by dissolving 4 g of N,N-dimethylpropanolamine in 50 ml of an IPE solvent, in an ice bath. After the resulting product was stirred at room temperature for 2 hours, filtration was performed, then, the IPE layer of the filtrate was subjected to a washing treatment with an $NaHCO_3$ aqueous solution and an NaCl aqueous solution, and after liquid-liquid separation was performed, washing with water was performed. Thereafter, the IPE was distilled off, whereby 11.4 g of $(C_4F_9)_2NC_2F_4COOC_3H_6N(CH_3)_2$ was obtained as a crude product (yield of 50%).

Next, 3 g of $(C_4F_9)_2NC_2F_4COOC_3H_6N(CH_3)_2$ obtained above was refluxed overnight with sodium monochloroacetate under stirring in ethanol, whereby 3 g of dimethyl betaine substance represented by the following formula (388) was obtained (yield of 93%).

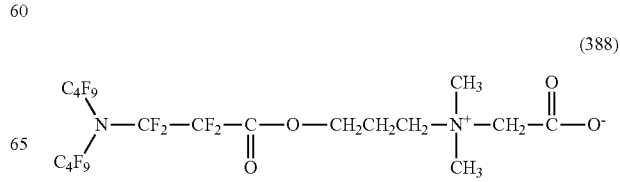

(388)

Synthesis Example 14

Synthesis of 2-[3-[[perfluoro(2-dimethylaminoethyl-sulfonyl)]amino]propyl-dimethyl-ammonium] acetate 40 g of perfluoro[2-(dimethylamino)ethanesulfonic acid fluoride obtained by the method described in Japanese Patent No. 4406700 was added dropwise to a solution obtained by dissolving 25.0 g of dimethylaminopropylamine in 250 ml of an IPE solvent, in an ice bath. After the resulting product was stirred at room temperature for 2 hours, filtration was performed, then, the IPE layer of the filtrate was subjected to a washing treatment with an $NaHCO_3$ aqueous solution and an NaCl aqueous solution, and after liquid-liquid separation was performed, washing with water was performed. Thereafter, the IPE was distilled off, and distillation was further performed, whereby 19.9 g of $(CF_3)_2NCF_2CF_2SO_2NHC_3H_6N(CH_3)_2$ was obtained as a crude product (yield of 45%).

Next, 8 g of $(CF_3)_2NCF_2CF_2SO_2NHC_3H_6N(CH_3)_2$ obtained above was refluxed overnight with sodium monochloroacetate under stirring in ethanol, and the resulting product was filtered and concentrated, whereby 9 g of dimethyl betaine substance represented by the following formula (389) was obtained (yield of 99%).

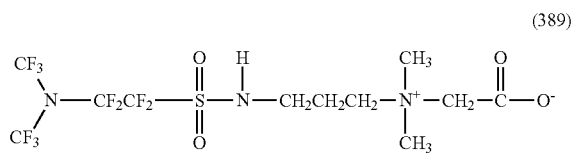
(389)

Synthesis Example 15

Synthesis of 3-[[perfluoro(2-methyl-3-dibutylamino-propanoyl)]amino]-N,N-dimethyl-propaneamine oxide 120 g of perfluoro(2-methyl-3-dibutylaminopropionic acid) fluoride obtained by electrolytic fluorination of methyl 2-methyl-3-dibutylaminopropionate was added dropwise to a solution obtained by dissolving 39 g of dimethylaminopropylamine in 500 ml of an IPE solvent, in an ice bath. After the resulting product was stirred at room temperature for 2 hours, filtration was performed, then, the IPE layer of the filtrate was subjected to a washing treatment with an $NaHCO_3$ aqueous solution and an NaCl aqueous solution, and after liquid-liquid separation was performed, washing with water was performed. Thereafter, the IPE was distilled off, and distillation was further performed, whereby 64 g of $(C_4F_9)_2NCF_2CF(CF_3)CONHC_3H_6N(CH_3)_2$ was obtained as a crude product (yield of 47%).

Next, 30 g of $(C_4F_9)_2NCF_2CF(CF_3)CONHC_3H_6N(CH_3)_2$ obtained above was reacted with hydrogen peroxide water at 70° C. for 1 hour under stirring in ethanol, then, activated carbon was added thereto, and the resulting product was stirred at 50° C. overnight, filtered, and concentrated, whereby 30 g of amine oxide substance represented by the following formula (390) was obtained (yield of 99%).

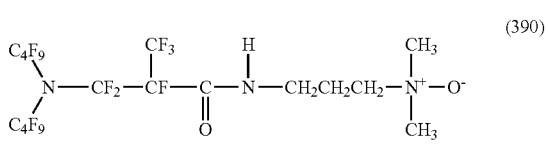
(390)

Synthesis Example 16

Synthesis of 3-[3-[[perfluoro(2-methyl-3-dibutylaminopropanoyl)]amino]propyl-dimethyl-ammonium] propanesulfonate 120 g of perfluoro(2-methyl-3-dibutylaminopropionic acid) fluoride obtained by electrolytic fluorination of methyl 2-methyl-3-dibutylaminopropionate was added dropwise to a solution obtained by dissolving 39 g of dimethylaminopropylamine in 500 ml of an IPE solvent, in an ice bath. After the resulting product was stirred at room temperature for 2 hours, filtration was performed, then, the IPE layer of the filtrate was subjected to a washing treatment with an $NaHCO_3$ aqueous solution and an NaCl aqueous solution, and after liquid-liquid separation was performed, washing with water was performed. Thereafter, the IPE was distilled off, and distillation was further performed, whereby 64 g of $(C_4F_9)_2NCF_2CF(CF_3)CONHC_3H_6N(CH_3)_2$ was obtained as a crude product (yield of 47%).

Next, 1.5 g of $(C_4F_9)_2NCF_2CF(CF_3)CONHC_3H_6N(CH_3)_2$ obtained above was refluxed for 23 hours with 1,3-propanesultone under stirring in acetonitrile, and reprecipitation was performed in a mixed solvent of a fluorine-based solvent (manufactured by Asahi Glass Co., Ltd., AK 225) and IPE, whereby 1.3 g of sulfobetaine substance represented by the following formula (391) was obtained (yield of 75%).

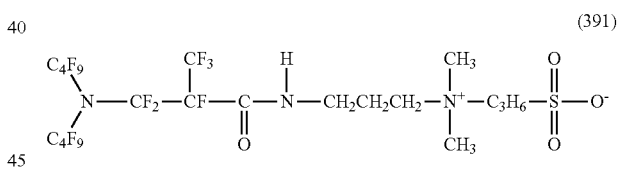
(391)

Synthesis Example 17

Synthesis of 2-[3-[[perfluoro(2-methyl-3-dibutylaminopropanoyl)]amino]propyl-dimethyl-ammonium] acetate 120 g of perfluoro(2-methyl-3-dibutylaminopropionic acid) fluoride obtained by electrolytic fluorination of methyl 2-methyl-3-dibutylaminopropionate was added dropwise to a solution obtained by dissolving 39 g of dimethylaminopropylamine in 500 ml of an IPE solvent, in an ice bath. After the resulting product was stirred at room temperature for 2 hours, filtration was performed, then, the IPE layer of the filtrate was subjected to a washing treatment with an $NaHCO_3$ aqueous solution and an NaCl aqueous solution, and after liquid-liquid separation was performed, washing with water was performed. Thereafter, the IPE was distilled off, and distillation was further performed, whereby 64 g of $(C_4F_9)_2NCF_2CF(CF_3)CONHC_3H_6N(CH_3)_2$ was obtained as a crude product (yield of 47%).

Next, 8 g of $(C_4F_9)_2NCF_2CF(CF_3)CONHC_3H_6N(CH_3)_2$ obtained above was refluxed overnight with sodium monochloroacetate under stirring in ethanol, and the resulting product was filtered and concentrated, whereby 8.5 g of dimethyl betaine substance represented by the following formula (392) was obtained (yield of 99%).

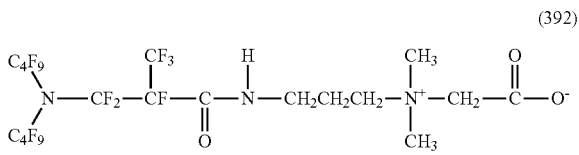

(392)

Synthesis Example 18

Synthesis of 3-[[perfluoro(2-methyl-3-dimethylaminopropanoyl)]amino]propyl-trimethyl-ammonium iodide 40 g of perfluoro(2-methyl-3-dimethylaminopropionic acid) fluoride obtained by an electrolytic fluorination of methyl 3-dimethylamino-2-methylpropionate was added dropwise to a solution obtained by dissolving 24.0 g of dimethylaminopropylamine in 250 ml of an IPE solvent, in an ice bath. After the resulting product was stirred at room temperature for 2 hours, filtration was performed, then, the IPE layer of the filtrate was subjected to a washing treatment with an $NaHCO_3$ aqueous solution and an NaCl aqueous solution, and after liquid-liquid separation was performed, washing with water was performed. Thereafter, the IPE was distilled off, and distillation was further performed, whereby 22.2 g of $(CF_3)_2NCF_2CF(CF_3)CONHC_3H_6N(CH_3)_2$ was obtained as a crude product (yield of 45%).

Next, methyl iodide was added to 10 g of the obtained crude product in methyl ethyl ketone, and the resulting product was stirred at room temperature overnight. After the reaction ended, collection by filtration was performed, whereby 8 g of a quaternary ammonium iodide represented by the following formula (393) was obtained (yield of 60%).

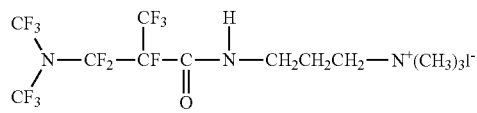

(393)

Synthesis Example 19

Synthesis of 3-[[perfluoro(3-dibutylaminopropanoyl)]amino]propyl-trimethyl-ammonium methyl-sulfate 20 g of perfluoro(3-dibutylaminopropionic acid) fluoride obtained by electrolytic fluorination of methyl 3-dibutylaminopropionate was added dropwise to a solution obtained by dissolving 4 g of dimethylaminopropylamine in 50 ml of an IPE solvent, in an ice bath. After the resulting product was stirred at room temperature for 2 hours, filtration was performed, then, the IPE layer of the filtrate was subjected to a washing treatment with an $NaHCO_3$ aqueous solution and an NaCl aqueous solution, and after liquid-liquid separation was performed, washing with water was performed. Thereafter, the IPE was distilled off, whereby 14 g of $(C_4F_9)_2NC_2F_4CONHC_3H_6N(CH_3)_2$ was obtained as a crude product (yield of 60%).

Next, 10 g of the above-obtained crude product $(C_4F_9)_2NC_2F_4CONHC_3H_6N(CH_3)_2$ was refluxed overnight with 2.6 g of dimethyl sulfate under stirring in MEK (methyl ethyl ketone), whereby 11.7 g of $CH_3SO_4$ substance represented by the following formula (394) was obtained (yield of 99%).

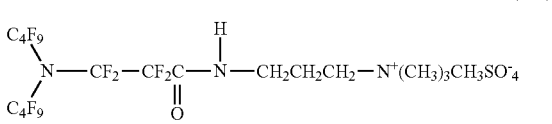

(394)

Synthesis Example 20

Synthesis of 2-[3-[[perfluoro(2-diethylaminoethylsulfonyl)]amino]propyl-dimethyl-ammonium] acetate Perfluoro(3-diethylamino)propionyl fluoride obtained by electrolytic fluorination of methyl 3-diethylaminopropionate was derived to perfluoro[2-(diethylamino)ethanesulfonic acid fluoride by the method described in Japanese Patent No. 4406700, and 50 g thereof was added dropwise to a solution obtained by dissolving 24.1 g of dimethylaminopropylamine in 250 ml of an IPE solvent, in an ice bath. After the resulting product was stirred at room temperature for 2 hours, filtration was performed, then, the IPE layer of the filtrate was subjected to a washing treatment with an $NaHCO_3$ aqueous solution and an NaCl aqueous solution, and after liquid-liquid separation was performed, washing with water was performed. Thereafter, the IPE was distilled off, and distillation was further performed, whereby 29.4 g of $(C_2F_5)_2NCF_2CF_2SO_2NHC_3H_6N(CH_3)_2$ was obtained as a crude product (yield of 50%).

Next, 10 g of $(C_2F_5)_2NCF_2CF_2SO_2NHC_3H_6N(CH_3)_2$ obtained above was refluxed overnight with sodium monochloroacetate under stirring in ethanol, and the resulting product was filtered and concentrated, whereby 1 g of dimethyl betaine substance represented by the following formula (395) was obtained (yield of 99%).

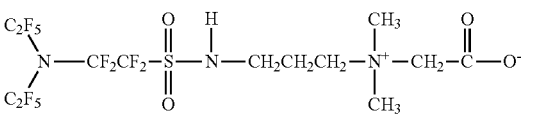

(395)

Synthesis Example 21

Synthesis of 2-[3-[[perfluoro(2-methyl-3-dihexylaminopropanoyl)]amino]propyl-dimethyl-ammonium] acetate 20 g of perfluoro(2-methyl-3-dihexylaminopropionic acid) fluoride obtained by electrolytic fluorination of methyl 2-methyl-3-dihexylaminopropionate was added dropwise to a solution obtained by dissolving 5 g of dimethylaminopropylamine in 50 ml of an IPE solvent, in an ice bath. After the resulting product was stirred at room temperature for 2 hours, filtration was performed, then, the IPE layer of the filtrate was subjected to a washing treatment with an NaHCO$_3$ aqueous solution and an NaCl aqueous solution, and after liquid-liquid separation was performed, washing with water was performed. Thereafter, the IPE was distilled off, and distillation was further performed, whereby 7.7 g of (C$_6$F$_{13}$)$_2$NCF$_2$CF(CF$_3$)CONHC$_3$H$_6$N(CH$_3$)$_2$ was obtained as a crude product (yield of 35%).

Next, 5 g of (C$_6$F$_{13}$)$_2$NCF$_2$CF(CF$_3$)CONHC$_3$H$_6$N(CH$_3$)$_2$ obtained above was refluxed overnight with sodium monochloroacetate under stirring in ethanol, and the resulting product was filtered and concentrated, whereby 5.2 g of dimethyl betaine substance represented by the following formula (396) was obtained (yield of 97%).

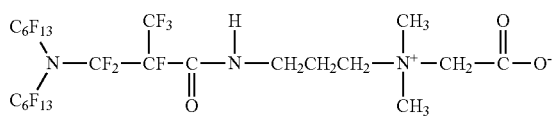

(396)

Synthesis Example 22

Synthesis of 4-[3-[[perfluoro(2-methyl-3-dibutylaminopropanoyl)]amino]propyl-dimethyl-ammonium butanesulfonate 120 g of perfluoro(2-methyl-3-dibutylaminopropionic acid) fluoride obtained by electrolytic fluorination of methyl 2-methyl-3-dibutylaminopropionate was added dropwise to a solution obtained by dissolving 39 g of dimethylaminopropylamine in 500 ml of an IPE solvent, in an ice bath. After the resulting product was stirred at room temperature for 2 hours, filtration was performed, then, the IPE layer of the filtrate was subjected to a washing treatment with an NaHCO$_3$ aqueous solution and an NaCl aqueous solution, and after liquid-liquid separation was performed, washing with water was performed. Thereafter, the IPE was distilled off, and distillation was further performed, whereby 64 g of (C$_4$F$_9$)$_2$NCF$_2$CF(CF$_3$)CONHC$_3$H$_6$N(CH$_3$)$_2$ was obtained as a crude product (yield of 47%).

Next, 15 g of (C$_4$F$_9$)$_2$NCF$_2$CF(CF$_3$)CONHC$_3$H$_6$N(CH$_3$)$_2$ obtained above was refluxed for 18 hours with 4.2 g of 1,4-butanesultone under stirring in acetonitrile, and reprecipitation was performed in a mixed solvent of a fluorine-based solvent (manufactured by Asahi Glass Co., Ltd., AK 225) and IPE, whereby 13.3 g of sulfobetaine substance represented by the following formula (397) was obtained (yield of 75%).

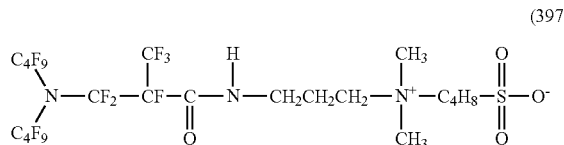

(397)

Synthesis Example 23

Synthesis of 3-[3-[[perfluoro(2-methyl-3-dibutylaminopropanoyl)]amino]propyl-dimethyl-ammonium] 2-hydroxypropane-1-sulfonate 120 g of perfluoro(2-methyl-3-dibutylaminopropionic acid) fluoride obtained by electrolytic fluorination of methyl 2-methyl-3-dibutylaminopropionate was added dropwise to a solution obtained by dissolving 39 g of dimethylaminopropylamine in 500 ml of an IPE solvent, in an ice bath. After the resulting product was stirred at room temperature for 2 hours, filtration was performed, then, the IPE layer of the filtrate was subjected to a washing treatment with an NaHCO$_3$ aqueous solution and an NaCl aqueous solution, and after liquid-liquid separation was performed, washing with water was performed. Thereafter, the IPE was distilled off, and distillation was further performed, whereby 64 g of (C$_4$F$_9$)$_2$NCF$_2$CF(CF$_3$)CONHC$_3$H$_6$N(CH$_3$)$_2$ was obtained as a crude product (yield of 47%).

Next, 5.0 g of (C$_4$F$_9$)$_2$NCF$_2$CF(CF$_3$)CONHC$_3$H$_6$N(CH$_3$)$_2$ obtained above was mixed with 2.0 g of sodium 3-chloro-2-hydroxypropanesulfonate, 10 ml of ethanol, and 2.1 g of water, and the resulting product was refluxed for 20 hours. Thereafter, 0.7 g of sodium carbonate was added thereto, and the resulting product was further refluxed for 4 hours. After the reaction ended, the reaction solution was poured into water, and reprecipitation was performed on the obtained solid in a mixed solvent of a fluorine-based solvent (manufactured by Asahi Glass Co., Ltd.: AK 225) and IPE, whereby 3.5 g of sulfobetaine represented by the following formula (398) was obtained (yield of 59%).

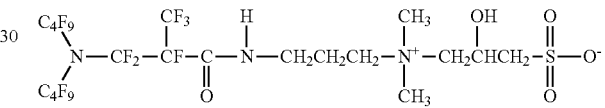

(398)

Synthesis Example 24

Synthesis of perfluoro(2-methyl-3-piperidinopropionic acid) calcium 564 g of a 12.5% sodium hydroxide aqueous solution was put into a 2 L glass flask, and by adding 421 g of perfluoro (2-methyl-3-piperidinopropionic acid) fluoride obtained by electrolytic fluorination of methyl 2-methyl-3-piperidinopropionate dropwise thereto, a reaction was performed. After adding dropwise, 400 mL of ethyl acetate was added thereto, and by extraction, perfluoro(2-methyl-3-piperidinopropionic acid) sodium was obtained. After the ethyl acetate layer and the water were separated, the ethyl acetate was distilled off using a rotary evaporator, whereby 310 g of perfluoro(2-methyl-3-piperidinopropionic acid) sodium was obtained as a white solid.

Next, 310 g of perfluoro(2-methyl-3-piperidinopropionic acid) sodium and 423 g of 95% sulfuric acid were put into a 1 L glass flask, followed by mixing, and distillation was performed under reduced pressure, whereby 273 g of perfluoro(2-methyl-3-piperidinopropionic acid) which was a solid at room temperature was obtained (the yield from the sodium salt was 92%).

Next, 3.0 g of perfluoro(2-methyl-3-piperidinopropionic acid) was neutralized with 0.2 g of calcium hydroxide in a methanol/water mixed solution, followed by drying, and 2.9 g of a calcium salt of a carboxylic acid represented by the following formula (399) was obtained (calcium salt yield of 93%).

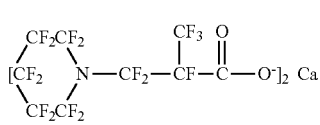
(399)

Synthesis Example 25

Synthesis of perfluoro(2-methyl-3-piperidinopropionic acid) sodium

Next, 10.0 g of the perfluoro(2-methyl-3-piperidinopropionic acid) obtained in Synthesis Example 1 was neutralized with 0.9 g of sodium hydroxide in water, followed by drying, and 10.1 g of a sodium salt of a carboxylic acid represented by the following formula (400) was obtained (yield of 96%).

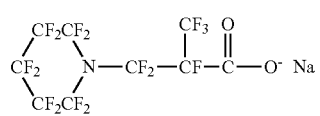
(400)

Synthesis Example 26

Synthesis of perfluoro(2-methyl-3-piperidinopropionic acid) potassium

Next, 10.0 g of the perfluoro(2-methyl-3-piperidinopropionic acid) obtained in Synthesis Example 1 was neutralized with 2.6 g of 48% potassium hydroxide in water, followed by drying, and 10.1 g of a potassium salt of a carboxylic acid represented by the following formula (401) was obtained (yield of 93%).

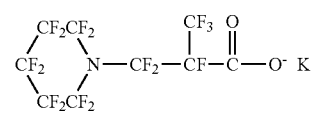
(401)

Synthesis Example 27

Synthesis of perfluoro(3-piperidinopropionic acid) sodium

Perfluoro(3-piperidinopropionic acid) was obtained in the same manner as in Synthesis Example 1 from perfluoro(3-piperidinopropionic acid) fluoride obtained by electrolytic fluorination of methyl 3-piperidinopropionate.

Next, 10.0 g of perfluoro(3-piperidinopropionic acid) was neutralized with 1.0 g of sodium hydroxide, followed by drying, and 10.2 g of a sodium salt of a carboxylic acid represented by the following formula (402) was obtained (yield of 97%).

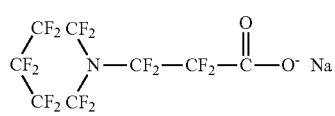
(402)

Synthesis Example 28

Synthesis of perfluoro(3-piperidinopropionic acid) potassium

Perfluoro(3-piperidinopropionic acid) was obtained in the same manner as in Synthesis Example 1 from perfluoro(3-piperidinopropionic acid) fluoride obtained by electrolytic fluorination of methyl 3-piperidinopropionate.

Next, 10.0 g of perfluoro(3-piperidinopropionic acid) was neutralized with 2.9 g of 48% potassium hydroxide, followed by drying, and 10.5 g of a potassium salt of a carboxylic acid represented by the following formula (403) was obtained (yield of 97%).

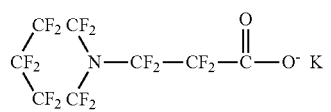
(403)

Synthesis Example 29

Synthesis of perfluoro(3-piperidinopropionic acid) ammonium

Perfluoro(3-piperidinopropionic acid) was obtained in the same manner as in Synthesis Example 1 from perfluoro(3-piperidinopropionic acid) fluoride obtained by electrolytic fluorination of methyl 3-piperidinopropionate.

Next, 10.0 g of perfluoro(3-piperidinopropionic acid) was neutralized with 1.5 g of a 28% ammonium aqueous solution, followed by drying, and 10.0 g of an ammonium salt of a carboxylic acid represented by the following formula (404) was obtained (yield of 96%).

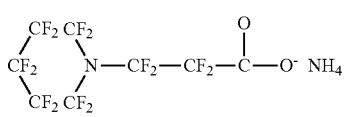
(404)

Synthesis Example 30

Synthesis of perfluoro(2-methyl-3-morpholinopropionic acid) potassium

Perfluoro(2-methyl-3-morpholinopropionic acid) was obtained in the same manner as in Synthesis Example 1 from perfluoro(2-methyl-3-morpholinopropionic acid) fluoride obtained by electrolytic fluorination of methyl 2-methyl-3-morpholinopropionate.

Next, 10.0 g of perfluoro(2-methyl-3-morpholinopropionic acid) was neutralized with 2.7 g of 48% potassium hydroxide, followed by drying, and 10.3 g of a potassium salt of a carboxylic acid represented by the following formula (405) was obtained (yield of 95%).

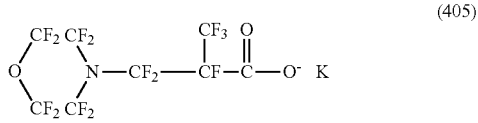
(405)

Synthesis Example 31

Synthesis of perfluoro(2-methyl-3-morpholinopropionic acid) ammonium

Perfluoro(2-methyl-3-morpholinopropionic acid) was obtained in the same manner as in Synthesis Example 1 from perfluoro(2-methyl-3-morpholinopropionic acid) fluoride obtained by electrolytic fluorination of methyl 2-methyl-3-morpholinopropionate.

Next, 10.0 g of perfluoro(2-methyl-3-morpholinopropionic acid) was neutralized with 1.4 g of a 28% ammonium aqueous solution, followed by drying, and 9.9 g of an ammonium salt of a carboxylic acid represented by the following formula (406) was obtained (yield of 95%).

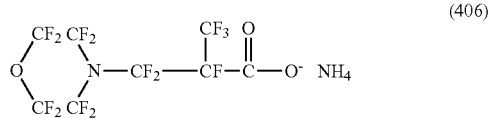
(406)

Synthesis Example 32

Synthesis of perfluoro(3-methyl-3-morpholinopropionic acid) sodium

Perfluoro(3-methyl-3-morpholinopropionic acid) was obtained in the same manner as in Synthesis Example 1 from perfluoro(3-methyl-3-morpholinopropionic acid) fluoride obtained by electrolytic fluorination of methyl 3-methyl-3-morpholinopropionate.

Next, 10.0 g of perfluoro(3-methyl-3-morpholinopropionic acid) was neutralized with 0.9 g of sodium hydroxide, followed by drying, and 10.0 g of a sodium salt of a carboxylic acid represented by the following formula (407) was obtained (yield of 95%).

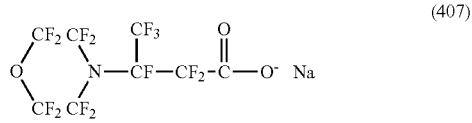
(407)

Synthesis Example 33

Synthesis of perfluoro(3-methyl-3-morpholinopropionic acid) potassium

Perfluoro(3-methyl-3-morpholinopropionic acid) was obtained in the same manner as in Synthesis Example 1 from perfluoro(3-methyl-3-morpholinopropionic acid) fluoride obtained by electrolytic fluorination of methyl 3-methyl-3-morpholinopropionate.

Next, 5.0 g of perfluoro(3-methyl-3-morpholinopropionic acid) was neutralized with 1.4 g of 48% potassium hydroxide, followed by drying, and 5.1 g of a potassium salt of a carboxylic acid represented by the following formula (408) was obtained (yield of 94%).

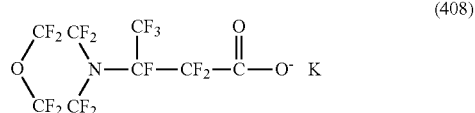
(408)

Synthesis Example 34

Synthesis of perfluoro(3-methyl-3-morpholinopropionic acid) ammonium

Perfluoro(3-methyl-3-morpholinopropionic acid) was obtained in the same manner as in Synthesis Example 1 from perfluoro(3-methyl-3-morpholinopropionic acid) fluoride obtained by electrolytic fluorination of methyl 3-methyl-3-morpholinopropionate.

Next, 5.0 g of perfluoro(3-methyl-3-morpholinopropionic acid) was neutralized with 0.7 g of a 28% ammonium aqueous solution, followed by drying, and 5.0 g of an ammonium salt of a carboxylic acid represented by the following formula (409) was obtained (yield of 96%).

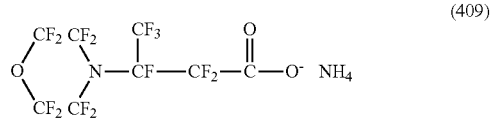
(409)

Synthesis Example 35

Synthesis of perfluoro[2-methyl-3-(3,5-dimethyl-morpholino)propionic acid] calcium Perfluoro[2-methyl-3-(3,5-dimethylmorpholino) propionic acid] was obtained in the same manner as in Synthesis Example 1 from perfluoro[2-methyl-3-(3,5-dimethylmorpholino)propionic acid] fluoride obtained by electrolytic fluorination of methyl 2-methyl-3-(3,5-dimethylmorpholino) propionate.

Next, 3.0 g of perfluoro[2-methyl-3-(3,5-dimethylmorpholino) propionic acid was neutralized with 0.2 g of calcium hydroxide, followed by drying, and 2.8 g of a calcium salt of a carboxylic acid represented by the following formula (410) was obtained (yield of 90%).

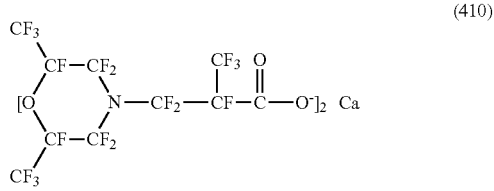
(410)

Synthesis Example 36

Synthesis of 6-[[perfluoro(2-methyl-3-piperidino-propanoyl)]amino] hexanoic acid calcium 9.2 g of perfluoro(2-methyl-3-piperidinopropionic acid) fluoride obtained by electrolytic fluorination of methyl 2-methyl-3-piperidinopropionate was reacted with 3.5 g of propyl 6-aminohexanoate at room temperature in the presence of triethylamine, whereby 7.7 g of an amide substance was synthesized (yield of 63%).

Next, 3.1 g of the amide substance was added to 1.1 g of formic acid under hydrochloric acid acidity conditions, followed by heating to 95° C., whereby 1.8 g of 6-[3-[perfluoro(2-methyl-3-piperidinopropanoyl)]amino] hexanoic acid (hereinafter, abbreviated as "PFPAH") was obtained (yield of 57%).

Next, 1.0 g of PFPAH was neutralized with 0.1 g of calcium hydroxide, followed by drying, whereby 0.9 g of a calcium salt of PFPAH represented by the following formula (411) was obtained (calcium salt yield of 87%).

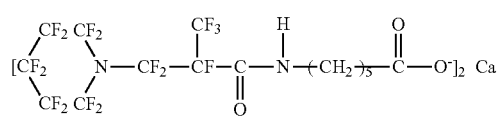

(411)

Synthesis Example 37

Synthesis of 6-[[perfluoro(2-methyl-3-piperidino-propanoyl)]amino] hexanoic acid sodium Next, 1.0 g of PFPAH obtained in the same manner as in Synthesis Example 13 was neutralized with 0.07 g of sodium hydroxide, followed by drying, whereby 1.0 g of a sodium salt of PFPAH represented by the following formula (412) was obtained (sodium salt yield of 96%).

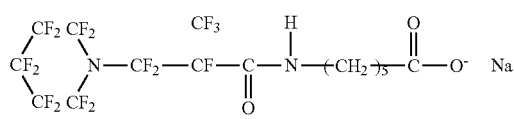

(412)

Synthesis Example 38

Synthesis of 4-[[perfluoro(2-methyl-3-piperidino-propanoyl)]amino] benzenesulfonic acid sodium 9.2 g of perfluoro(2-methyl-3-piperidinopropionic acid) fluoride obtained by electrolytic fluorination was reacted with 3.5 g of 4-aminobenzenesulfonic acid in 25 ml of acetonitrile to which 3.3 g of pyridine had been added at room temperature for 4 hours. Next, 25 ml IPE was added thereto, and the resulting product was crystallizes and filtered, whereby 9.6 g of a 4-[[perfluoro(2-methyl-3-piperidinopropanoyl)]amino] benzenesulfonic acid pyridine salt was obtained (yield of 69%).

Next, after the above pyridine salt was reacted with 48% caustic soda, then, the resulting product was neutralized with hydrochloric acid, and a by-product sodium chloride was removed by filtration, methanol was added thereto, and sodium chloride was precipitated again and removed, whereby a sodium sulfonate represented by the following formula (413) was obtained (sodium salt yield of 90%).

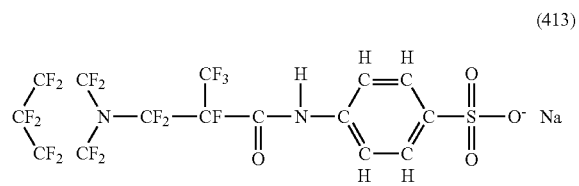

(413)

Synthesis Example 39

Synthesis of 4-[[perfluoro(2-methyl-3-piperidino-propanoyl)]amino] benzenesulfonic acid potassium After 9.6 g of 4-[[perfluoro(2-methyl-3-piperidinopropanoyl)]amino] benzenesulfonic acid pyridine salt obtained in the same manner as in Synthesis Example 15 was reacted with a saturated potassium chloride solution, then, the resulting product was neutralized with hydrochloric acid, and a by-product potassium chloride was removed by filtration, methanol was added thereto, and potassium chloride was precipitated again and removed, whereby a potassium sulfonate represented by the following formula (414) was obtained (potassium salt yield of 80%).

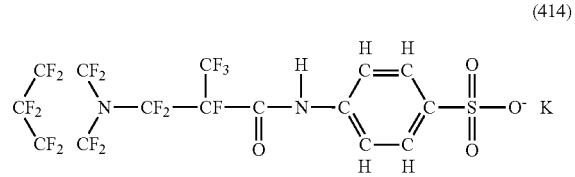

(414)

Synthesis Example 40

Synthesis of 3-[[perfluoro(2-methyl-3-piperidino-propanoyl)]amino]propyl-trimethyl-ammonium iodide 20 g of perfluoro(2-methyl-3-piperidinopropionic acid) fluoride obtained by electrolytic fluorination was added dropwise to a solution obtained by dissolving 9 g of dimethylaminopropylamine in 110 ml of an IPE solvent, in an ice bath. After the resulting product was stirred at room temperature for 2 hours, filtration was performed, the IPE layer of the filtrate was subjected to a washing treatment with an NaHCO$_3$ aqueous solution and an NaCl aqueous solution, and after liquid-liquid separation was performed, washing with water was performed, and IPE was distilled off, whereby 18 g of $CF_2(CF_2CF_2)_2NCF_2CF(CF_3)CONHC_3H_6N(CH_3)_2$ was obtained (crude product yield of 76%).

Next, methyl iodide was added to the obtained crude product in methyl ethyl ketone, and the resulting product was stirred at room temperature overnight. After the reaction ended, collection by filtration was performed, whereby a 20 g of quaternary ammonium iodide substance represented by the following formula (415) was obtained (quaternary ammonium salt yield of 88%).

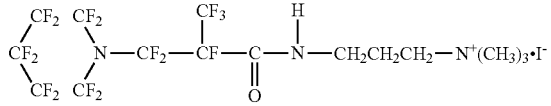
(415)

Synthesis Example 41

Synthesis of 3-[[perfluoro(2-methyl-3-morpholino-propanoyl)]amino]propyl-trimethyl-ammonium iodide 21 g of perfluoro(2-methyl-3-morpholinopropionic acid) fluoride obtained by electrolytic fluorination was added dropwise to a solution obtained by dissolving 10 g of dimethylaminopropylamine in 100 ml of an IPE solvent, in an ice bath. Thereafter, after the resulting product was stirred at room temperature for 2 hours, filtration was performed, the IPE layer of the filtrate was subjected to a washing treatment with an $NaHCO_3$ aqueous solution and an NaCl aqueous solution, and after liquid-liquid separation was performed, washing with water was performed, and IPE was distilled off, whereby 22 g of $O(CF_2CF_2)_2NCF_2CF(CF_3)CONHC_3H_6N(CH_3)_2$ was obtained as a crude product (crude product yield of 88%).

Next, the resulting product was reacted with methyl iodide in the same manner as in Synthesis Example 16, whereby a 27 g of quaternary ammonium iodide substance represented by the following formula (416) was obtained (quaternary ammonium salt yield of 96%).

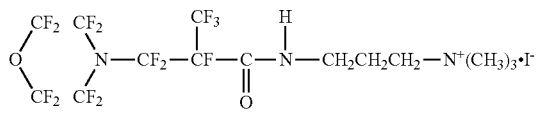
(416)

Synthesis Example 42

Synthesis of 2-[3-[[perfluoro(2-methyl-3-piperidino-panoyl)]amino]propyl-dimethyl-ammonium] acetate 10 g of the crude product $CF_2(CF_2CF_2)_2NCF_2CF(CF_3)CONHC_3H_6N(CH_3)_2$ obtained in the same manner as in Synthesis Example 17 was refluxed overnight with 3 g of sodium monochloroacetate under stirring in ethanol, whereby 11 g of dimethyl betaine substance represented by the following formula (417) was obtained (yield of 99%).

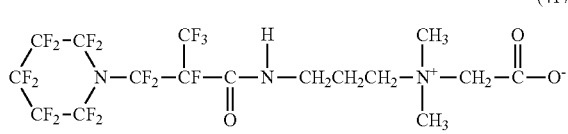
(417)

Synthesis Example 43

Synthesis of 2-[3-[perfluoro(2-methyl-3-morpholinopropanoyl)]oxypropyl-dimethyl-ammonium] acetate 10 g of perfluoro(2-methyl-3-morpholinopropionic acid) fluoride obtained by electrolytic fluorination of methyl 2-methyl-3-morpholinopropionate was added dropwise to a solution obtained by dissolving 5 g of N,N-dimethylpropanolamine in 100 mL of an IPE solvent, in an ice bath. Thereafter, after the resulting product was stirred at room temperature for 2 hours, filtration was performed, the IPE layer of the filtrate was subjected to a washing treatment with an $NaHCO_3$ aqueous solution and an NaCl aqueous solution, and after liquid-liquid separation was performed, washing with water was performed, and IPE was distilled off, whereby 6 g of $O((CF_2CF_2)_2NCF_2COOC_3H_6N(CH_3)_2$ was obtained as a crude product (crude product yield of 50%).

Next, 5 g of the above-obtained crude product $O(CF(CF_3)CF_2)_2NCF_2COOC_3H_6N(CH_3)_2$ was refluxed overnight with 1.2 g of sodium monochloroacetate under stirring in ethanol, whereby 5.1 g of dimethyl betaine substance represented by the following formula (418) was obtained (yield of 92%).

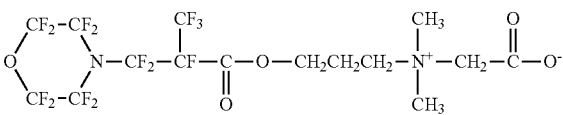
(418)

Synthesis Example 44

Synthesis of 2-[3-[[perfluoro(3-morpholinopropyl-sulfonyl)]amino]propyl-dimethyl-ammonium] acetate 4 g of perfluoro-(N-morpholinopropanesulfonyl) fluoride obtained by electrolytic fluorination of N-morpholino propanesulfonyl chloride was added dropwise to a solution obtained by dissolving 2 g of dimethylaminopropylamine in 20 ml of an IPE solvent, in an ice bath. After the resulting product was stirred at room temperature for 2 hours, filtration was performed, then, the IPE layer of the filtrate was subjected to a washing treatment with an $NaHCO_3$ aqueous solution and an NaCl aqueous solution, and after liquid-liquid separation was performed, washing with water was performed. Thereafter, the IPE was distilled off, and distillation was further performed, whereby 2.1 g of $O(C_2F_4)_2NC_3F_6SO_2NHC_3H_6N(CH_3)_2$ was obtained as a crude product (yield of 45%).

Next, 1 g of $O(C_2F_4)_2NC_3F_6SO_2NHC_3H_6N(CH_3)_2$ obtained above was refluxed overnight with sodium monochloroacetate under stirring in ethanol, and the resulting product was filtered and concentrated, whereby 1.1 g of dimethyl betaine substance represented by the following formula (419) was obtained (yield of 99%).

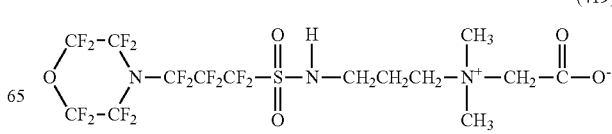
(419)

Synthesis Example 45

Synthesis of 2-[3-[[perfluoro(pyrrolidinoacetyl)]amino]propyl-dimethyl-ammonium] acetate 15 g of perfluoro(pyrrolidinoacetylfluoride) obtained by electrolytic fluorination of N-(2-hydroxyethyl) pyrrolidine was added dropwise to a solution obtained by dissolving 10 g of dimethylaminopropylamine in 100 ml of an IPE solvent, in an ice bath. Thereafter, after the resulting product was stirred at room temperature for 2 hours, filtration was performed, the IPE layer of the filtrate was subjected to a washing treatment with an NaHCO$_3$ aqueous solution and an NaCl aqueous solution, and after liquid-liquid separation was performed, washing with water was performed, and IPE was distilled off, whereby 14.2 g of (CF$_2$CF$_2$)$_2$NCF$_2$CONHC$_3$H$_6$N(CH$_3$)$_2$ was obtained as a crude product (crude product yield of 75%).

Next, 10 g of the above-obtained crude product (CF$_2$CF$_2$)$_2$ NCF$_2$CONHC$_3$H$_6$N(CH$_3$) was refluxed overnight with 4 g of sodium monochloroacetate under stirring in ethanol, whereby 11.4 g of dimethyl betaine substance represented by the following formula (420) was obtained (yield of 99%).

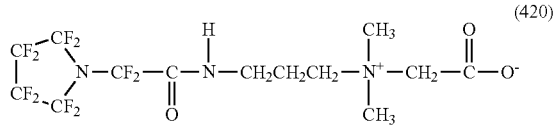

(420)

Synthesis Example 46

Synthesis of 3-[3-[[perfluoro(2-methyl-3-morpholinopropanoyl)]amino]propyl-dimethyl-ammonium] propanesulfonate 21 g of perfluoro(2-methyl-3-morpholinopropionic acid) fluoride obtained by electrolytic fluorination of methyl 2-methyl-3-morpholinopropionate was added dropwise to a solution obtained by dissolving 10 g of dimethylaminopropylamine in 100 ml of an IPE solvent, in an ice bath. Thereafter, after the resulting product was stirred at room temperature for 2 hours, filtration was performed, the IPE layer of the filtrate was subjected to a washing treatment with an NaHCO$_3$ aqueous solution and an NaCl aqueous solution, and after liquid-liquid separation was performed, washing with water was performed, and IPE was distilled off, whereby 22 g of O(CF$_2$CF$_2$)$_2$NCF$_2$CF(CF$_3$)CONHC$_3$H$_6$N(CH$_3$)$_2$ was obtained as a crude product (crude product yield of 88%).

Next, 2 g of O(CF$_2$CF$_2$)$_2$NCF$_2$CF(CF$_3$)CONHC$_3$H$_6$N(CH$_3$)$_2$ obtained above was refluxed overnight with 1,3-propanesultone under stirring in methylene chloride, and reprecipitation was performed in a mixed solvent of a fluorine-based solvent (manufactured by Asahi Glass Co., Ltd., AK 225) and IPE, whereby 2.2 g of sulfobetaine substance represented by the following formula (421) was obtained (yield of 98%).

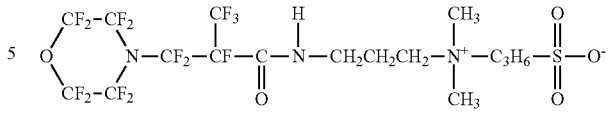

(421)

Synthesis Example 47

Synthesis of 3-[[perfluoro(2-methyl-3-morpholinopropanoyl)]amino]-N,N-dimethyl-propaneamine oxide 21 g of perfluoro(2-methyl-3-morpholinopropionic acid) fluoride obtained by electrolytic fluorination of methyl 2-methyl-3-morpholinopropionate was added dropwise to a solution obtained by dissolving 10 g of dimethylaminopropylamine in 100 ml of an IPE solvent, in an ice bath. Thereafter, after the resulting product was stirred at room temperature for 2 hours, filtration was performed, the IPE layer of the filtrate was subjected to a washing treatment with an NaHCO$_3$ aqueous solution and an NaCl aqueous solution, and after liquid-liquid separation was performed, washing with water was performed, and IPE was distilled off, whereby 22 g of O(CF$_2$CF$_2$)$_2$NCF$_2$CF(CF$_3$)CONHC$_3$H$_6$N(CH$_3$)$_2$ was obtained as a crude product (crude product yield of 88%).

Next, 5 g of O(CF$_2$CF$_2$)$_2$NCF$_2$CF(CF$_3$)CONHC$_3$H$_6$N(CH$_3$)$_2$ obtained above was reacted with hydrogen peroxide water at 70° C. for 2 hour under stirring in ethanol, and the resulting product was extracted and concentrated, whereby 2 g of amine oxide substance represented by the following formula (422) was obtained (yield of 39%).

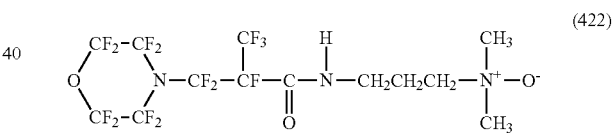

(422)

Synthesis Example 48

Synthesis of 3-[[perfluoro(2-methyl-3-piperidinopropanoyl)]amino]propyl-trimethyl-ammonium methylsulfate 20 g of perfluoro(2-methyl-3-piperidinopropionic acid) fluoride obtained by electrolytic fluorination of methyl 2-methyl-3-piperidinopropionate was added dropwise to a solution obtained by dissolving 9 g of dimethylaminopropylamine in 110 ml of an IPE solvent, in an ice bath. After the resulting product was stirred at room temperature for 2 hours, filtration was performed, the IPE layer of the filtrate was subjected to a washing treatment with an NaHCO$_3$ aqueous solution and an NaCl aqueous solution, and after liquid-liquid separation was performed, washing with water was performed, and IPE was distilled off, whereby 18 g of CF$_2$(CF$_2$CF$_2$)$_2$NCF$_2$CF(CF$_3$)CONHC$_3$H$_6$N(CH$_3$)$_2$ was obtained (crude product yield of 76%).

Next, 10.9 g of the above-obtained crude product CF$_2$(CF$_2$CF$_2$)$_2$NCF$_2$CF(CF$_3$)CONHC$_3$H$_6$N(CH$_3$)$_2$ was refluxed overnight with 2.6 g of dimethyl sulfate under stirring in MEK, whereby 13.6 g of CH₃SO₄ substance represented by the following formula (423) was obtained (yield of 99%).

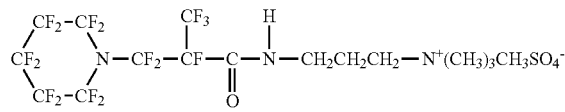
(423)

Synthesis Example 49

Synthesis of 2-[3-[[perfluoro(2-methyl-3-(4-methyl-1-piperazyl)propanoyl)]amino]propyl-dimethyl-ammonium] acetate 20 g of perfluoro(2-methyl-3-(4-methyl-1-piperazyl)propionic acid) fluoride obtained by electrolytic fluorination of methyl 2-methyl-3-(4-methyl-1-piperazyl) propionate was added dropwise to a solution obtained by dissolving 8.5 g of dimethylaminopropylamine in 100 ml of an IPE solvent, in an ice bath. Thereafter, after the resulting product was stirred at room temperature for 2 hours, filtration was performed, the IPE layer of the filtrate was subjected to a washing treatment with an NaHCO₃ aqueous solution and an NaCl aqueous solution, and after liquid-liquid separation was performed, washing with water was performed, and IPE was distilled off, whereby 19.8 g of $CF_3N(CF_2CF_2)_2NCF_2CF(CF_3)CONHC_3H_6N(CH_3)_2$ was obtained (crude product yield of 85%).

Next, 10 g of the above-obtained crude product $CF_3N(CF_2CF_2)_2NCF_2CF(CF_3)CONHC_3H_6N(CH_3)_2$ was refluxed overnight with 3 g of sodium monochloroacetate under stirring in ethanol, whereby 10.9 g of dimethyl betaine substance represented by the following formula (424) was obtained (yield of 99%).

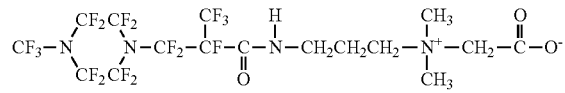
(424)

<Manufacture of Surface Coating Material>

Examples 1 to 11

By dissolving respective nitrogen-containing fluorine-based compounds synthesized in Synthesis Examples 1 to 11 in methanol, respective 2.0% by mass methanol solutions were prepared. These were used as surface coating materials of Examples 1 to 11.

Example 12

By dissolving the nitrogen-containing fluorine-based compound synthesized in Synthesis Example 1 in methanol, a 0.2% by mass methanol solution was prepared. This was used as a surface coating material of Example 12.

Example 13

By dissolving the nitrogen-containing fluorine-based compound synthesized in Synthesis Example 11 in methanol, a 0.2% by mass methanol solution was prepared. Furthermore, by adding a polyvinyl butyral resin (S-LEC BL-1 manufactured by Sekisui Chemical Co., Ltd.) as a binder thereto such that the mass composition ratio (nitrogen-containing fluorine-based compound:binder) of the nitrogen-containing fluorine-based compound to the binder became 10:90, a surface coating material of Example 13 was obtained.

Example 14

By dissolving the nitrogen-containing fluorine-based compound synthesized in Synthesis Example 11 in methanol, a 1.3% by mass methanol solution was prepared. Furthermore, by adding a polyvinyl butyral resin (S-LEC KX-5 manufactured by Sekisui Chemical Co., Ltd.) as a binder thereto such that the mass composition ratio (nitrogen-containing fluorine-based compound:binder) of the nitrogen-containing fluorine-based compound to the binder became 65:35, a surface coating material of Example 14 was obtained.

Example 15

By dissolving the nitrogen-containing fluorine-based compound synthesized in Synthesis Example 1 in methanol, a 0.5% by mass methanol solution was prepared. Furthermore, by adding water glass (No. 3 manufactured by Fuji Kagaku CORP.) as a binder thereto such that the mass composition ratio (nitrogen-containing fluorine-based compound:binder) of the nitrogen-containing fluorine-based compound to the binder became 10:90, a surface coating material of Example 15 was obtained.

Example 16

By dissolving the nitrogen-containing fluorine-based compound synthesized in Synthesis Example 1 in methanol, a 5.0% by mass methanol solution was prepared. Furthermore, by adding polyethylene glycol diacrylate (NK-A-200 manufactured by Shin-Nakamura Chemical Co.) as a binder thereto such that the mass composition ratio (nitrogen-containing fluorine-based compound:binder) of the nitrogen-containing fluorine-based compound to the binder became 10:90, a surface coating material of Example 16 was obtained.

Example 17

By dissolving the nitrogen-containing fluorine-based compound synthesized in Synthesis Example 11 in methanol, a 10.0% by mass methanol solution was prepared. Furthermore, by adding a polyvinyl butyral resin (S-LEC BL-1 manufactured by Sekisui Chemical Co., Ltd.) as a binder thereto such that the mass composition ratio (nitrogen-containing fluorine-based compound:binder) of the nitrogen-containing fluorine-based compound to the binder became 91:9, a surface coating material of Example 17 was obtained.

Example 18

By dissolving the nitrogen-containing fluorine-based compound synthesized in Synthesis Example 11 in methanol, a 10.0% by mass methanol solution was prepared. Furthermore, by adding a polyvinyl butyral resin (S-LEC BL-1 manufactured by Sekisui Chemical Co., Ltd.) as a binder thereto such that the mass composition ratio (nitrogen-containing fluorine-based compound:binder) of the nitrogen-containing fluorine-based compound to the binder became 50:50, a surface coating material of Example 18 was obtained.

Example 19

By dissolving the nitrogen-containing fluorine-based compound synthesized in Synthesis Example 11 in methanol, a 10.0% by mass methanol solution was prepared. Furthermore, by adding a polyvinyl butyral resin (S-LEC BL-1 manufactured by Sekisui Chemical Co., Ltd.) as a binder thereto such that the mass composition ratio (nitrogen-containing fluorine-based compound:binder) of the nitrogen-containing fluorine-based compound to the binder became 25:75, a surface coating material of Example 19 was obtained.

Example 20

By dissolving the nitrogen-containing fluorine-based compound synthesized in Synthesis Example 12 in methanol, a 10.0% by mass methanol solution was prepared. Furthermore, by adding a polyvinyl butyral resin (S-LEC BL-1 manufactured by Sekisui Chemical Co., Ltd.) as a binder thereto such that the mass composition ratio (nitrogen-containing fluorine-based compound:binder) of the nitrogen-containing fluorine-based compound to the binder became 50:50, a surface coating material of Example 20 was obtained.

Example 21

By dissolving the nitrogen-containing fluorine-based compound synthesized in Synthesis Example 13 in methanol, a 10.0% by mass methanol solution was prepared. Furthermore, by adding a polyvinyl butyral resin (S-LEC BL-1 manufactured by Sekisui Chemical Co., Ltd.) as a binder thereto such that the mass composition ratio (nitrogen-containing fluorine-based compound:binder) of the nitrogen-containing fluorine-based compound to the binder became 50:50, a surface coating material of Example 21 was obtained.

Example 22

By dissolving the nitrogen-containing fluorine-based compound synthesized in Synthesis Example 14 in methanol, a 10.0% by mass methanol solution was prepared. Furthermore, by adding a polyvinyl butyral resin (S-LEC BL-1 manufactured by Sekisui Chemical Co., Ltd.) as a binder thereto such that the mass composition ratio (nitrogen-containing fluorine-based compound:binder) of the nitrogen-containing fluorine-based compound to the binder became 50:50, a surface coating material of Example 22 was obtained.

Example 23

By dissolving the nitrogen-containing fluorine-based compound synthesized in Synthesis Example 15 in a mixed solution of 90.0% by mass of methanol and 10.0% by mass of water, a 50.0% by mass solution was prepared. Furthermore, by adding a polyvinyl butyral resin (S-LEC BL-1 manufactured by Sekisui Chemical Co., Ltd.) as a binder thereto such that the mass composition ratio (nitrogen-containing fluorine-based compound:binder) of the nitrogen-containing fluorine-based compound to the binder became 90:10, a surface coating material of Example 23 was obtained.

Example 24

By dispersing the 3-[3-[[perfluoro(2-methyl-3-dibutylaminopropanoyl)]amino]propyl-dimethyl-ammonium] propanesulfonate obtained in Synthesis Example 16 in water as a nitrogen-containing fluorine-based compound, a 5.0% by mass aqueous dispersion was obtained. Furthermore, by adding polyvinyl alcohol (reagent manufactured by Wako Pure Chemical Industries, Ltd.) as a binder thereto such that the mass composition ratio (nitrogen-containing fluorine-based compound:binder) of the nitrogen-containing fluorine-based compound to the binder became 50:50, a surface coating material of Example 24 was obtained.

Example 25

By mixing the "2-[3-[[perfluoro(2-methyl-3-dibutylaminopropanoyl)]amino]propyl-dimethyl-ammonium] acetate obtained in Synthesis Example 17 as a nitrogen-containing fluorine-based compound with a polyester-based aqueous urethane resin (manufactured by Dai-ichi Kogyo Seiyaku Co., Ltd., "Superflex 210", solid content of 35%, water of 65%) having an anionic hydrophilic group as a hydrophilic group in a ratio of 6.0% by mass, and by adding a nitrogen-containing fluorine-based compound and a binder thereto such that the mass composition ratio (nitrogen-containing fluorine-based compound:binder) of the nitrogen-containing fluorine-based compound to the binder became 15:85, a surface coating material of Example 25 was obtained.

Example 26

By dissolving the nitrogen-containing fluorine-based compound synthesized in Synthesis Example 18 in methanol, a 10.0% by mass methanol solution was prepared. Furthermore, by adding a polyvinyl butyral resin (S-LEC BL-1 manufactured by Sekisui Chemical Co., Ltd.) as a binder thereto such that the mass composition ratio (nitrogen-containing fluorine-based compound:binder) of the nitrogen-containing fluorine-based compound to the binder became 99.9:0.1, a surface coating material of Example 26 was obtained.

Example 27

By dissolving the nitrogen-containing fluorine-based compound synthesized in Synthesis Example 1 and the nitrogen-containing fluorine-based compound synthesized in Synthesis Example 9 by equal weight in methanol, a 10.0% by mass methanol mixed solution was prepared. Furthermore, by adding a polyvinyl butyral resin (S-LEC BL-1 manufactured by Sekisui Chemical Co., Ltd.) as a binder thereto such that the mass composition ratio (nitrogen-containing fluorine-based compound:binder) of the nitrogen-containing fluorine-based compound to the binder became 20:80, a surface coating material of Example 27 was obtained.

Example 28

By dissolving the nitrogen-containing fluorine-based compound synthesized in Synthesis Example 19 in methanol, a 2.0% by mass methanol solution was prepared. Furthermore, by adding a polyvinyl butyral resin (S-LEC BL-1 manufactured by Sekisui Chemical Co., Ltd.) as a binder thereto such that the mass composition ratio (nitrogen-containing fluorine-based compound:binder) of the nitrogen-containing fluorine-based compound to the binder became 50:50, a surface coating material of Example 28 was obtained.

Example 29

By dissolving the nitrogen-containing fluorine-based compound synthesized in Synthesis Example 20 in methanol, a 2.0% by mass methanol solution was prepared. Furthermore, by adding a polyvinyl butyral resin (S-LEC BL-1 manufactured by Sekisui Chemical Co., Ltd.) as a binder thereto such that the mass composition ratio (nitrogen-containing fluorine-based compound:binder) of the nitrogen-containing fluorine-based compound to the binder became 50:50, a surface coating material of Example 29 was obtained.

Example 30

By dissolving the nitrogen-containing fluorine-based compound synthesized in Synthesis Example 21 in methanol, a 1.0% by mass methanol solution was prepared. Furthermore, tetraethoxysilane (reagent manufactured by Wako Pure Chemical Industries, Ltd.) was added such that the mass composition ratio (nitrogen-containing fluorine-based compound:binder) with the nitrogen-containing fluorine-based compound became 10:90. In addition, by adding a polyvinyl butyral resin (S-LEC BL-1 manufactured by Sekisui Chemical Co., Ltd.) as a binder thereto such that the mass composition ratio (nitrogen-containing fluorine-based compound:binder) of the nitrogen-containing fluorine-based compound to the binder became 50:50, a surface coating material of Example 30 was obtained.

Example 31

By dissolving 16.0 parts by mass of perfluoro(3-dibutylaminopropionic acid) calcium obtained in Synthesis Example 1 as a nitrogen-containing fluorine-based compound and 4.0 parts by mass of polyvinyl butyral (manufactured by Sekisui Chemical Co., Ltd., "S-LEC B BL-1") having a hydroxyl group as a hydrophilic group in 180.0 parts by mass of methanol, a surface coating material of Example 31 was obtained.

Example 32

By mixing 2.0 parts by mass of the nitrogen-containing fluorine-based compound synthesized in Synthesis Example 16 as a hydrophilic oil repellent and 98.0 parts by mass of ethanol as a solvent in this ratio and dissolving the resulting product, a surface coating material of Example 32 was obtained.

Example 33

By mixing 2.0 parts by mass of the nitrogen-containing fluorine-based compound synthesized in Synthesis Example 22 as a hydrophilic oil repellent and 98.0 parts by mass of ethanol as a solvent in this ratio and dissolving the resulting product, a surface coating material of Example 33 was obtained.

Example 34

By mixing 2.0 parts by mass of the nitrogen-containing fluorine-based compound synthesized in Synthesis Example 23 as a hydrophilic oil repellent and 98.0 parts by mass of ethanol as a solvent in this ratio and dissolving the resulting product, a surface coating material of Example 34 was obtained.

Examples 35 to 53

By dissolving respective nitrogen-containing fluorine-based compounds synthesized in Synthesis Examples 24 to 42 in methanol, respective 2.0% by mass methanol solutions were prepared. These were used as surface coating materials of Examples 35 to 53.

Example 54

By dissolving the nitrogen-containing fluorine-based compound synthesized in Synthesis Example 35 in methanol, a 0.2% by mass methanol solution was prepared. This was used as a surface coating material of Example 54.

Example 55

By dissolving the nitrogen-containing fluorine-based compound synthesized in Synthesis Example 42 in methanol, a 0.2% by mass methanol solution was prepared. Furthermore, by adding a polyvinyl butyral resin (S-LEC BL-1 manufactured by Sekisui Chemical Co., Ltd.) as a binder thereto such that the mass composition ratio (nitrogen-containing fluorine-based compound:binder) of the nitrogen-containing fluorine-based compound to the binder became 10:90, a surface coating material of Example 55 was obtained.

Example 56

By dissolving the nitrogen-containing fluorine-based compound synthesized in Synthesis Example 42 in methanol, a 1.3% by mass methanol solution was prepared. Furthermore, by adding a polyvinyl butyral resin (S-LEC KX-5 manufactured by Sekisui Chemical Co., Ltd.) as a binder thereto such that the mass composition ratio (nitrogen-containing fluorine-based compound:binder) of the nitrogen-containing fluorine-based compound to the binder became 65:35, a surface coating material of Example 56 was obtained.

Example 57

By dissolving the nitrogen-containing fluorine-based compound synthesized in Synthesis Example 24 in methanol, a 5.0% by mass methanol solution was prepared. Furthermore, by adding polyethylene glycol diacrylate (NK-A-200 manufactured by Shin-Nakamura Chemical Co.) as a binder thereto such that the mass composition ratio (nitrogen-containing fluorine-based compound:binder) of the nitrogen-containing fluorine-based compound to the binder became 10:90, a surface coating material of Example 57 was obtained.

Example 58

By dissolving the nitrogen-containing fluorine-based compound synthesized in Synthesis Example 42 in methanol, a 10.0% by mass methanol solution was prepared. Furthermore, by adding a polyvinyl butyral resin (S-LEC BL-1 manufactured by Sekisui Chemical Co., Ltd.) as a binder thereto such that the mass composition ratio (nitrogen-containing fluorine-based compound:binder) of the nitrogen-containing fluorine-based compound to the binder became 91:9, a surface coating material of Example 58 was obtained.

Example 59

By dissolving the nitrogen-containing fluorine-based compound synthesized in Synthesis Example 42 in methanol, a 10.0% by mass methanol solution was prepared. Furthermore, by adding a polyvinyl butyral resin (S-LEC BL-1 manufactured by Sekisui Chemical Co., Ltd.) as a binder was added thereto such that the mass composition ratio (nitrogen-containing fluorine-based compound:binder) of the nitrogen-containing fluorine-based compound to the binder became 50:50, a surface coating material of Example 59 was obtained.

Example 60

By dissolving the nitrogen-containing fluorine-based compound synthesized in Synthesis Example 42 in methanol, a 10.0% by mass methanol solution was prepared. Furthermore, by adding a polyvinyl butyral resin (S-LEC BL-1 manufactured by Sekisui Chemical Co., Ltd.) as a binder thereto such that the mass composition ratio (nitrogen-containing fluorine-based compound:binder) of the nitrogen-containing fluorine-based compound to the binder became 25:75, a surface coating material of Example 60 was obtained.

Example 61

By dissolving the nitrogen-containing fluorine-based compound synthesized in Synthesis Example 35 in methanol, a 0.5% by mass methanol solution was prepared. Furthermore, by adding water glass (No. 3 manufactured by Fuji Kagaku CORP.) as a binder thereto such that the mass composition ratio (nitrogen-containing fluorine-based compound:binder) of the nitrogen-containing fluorine-based compound to the binder became 10:90, a surface coating material of Example 61 was obtained.

Example 62

By dissolving the nitrogen-containing fluorine-based compound synthesized in Synthesis Example 43 in methanol, a 10.0% by mass methanol solution was prepared. Furthermore, by adding a polyvinyl butyral resin (S-LEC BL-1 manufactured by Sekisui Chemical Co., Ltd.) as a binder thereto such that the mass composition ratio (nitrogen-containing fluorine-based compound:binder) of the nitrogen-containing fluorine-based compound to the binder became 50:50, a surface coating material of Example 62 was obtained.

Example 63

By dissolving the nitrogen-containing fluorine-based compound synthesized in Synthesis Example 44 in a mixed solution of 90.0% by mass of methanol and 10.0% by mass of water, a 50.0% by mass solution was prepared. Furthermore, by adding a polyvinyl butyral resin (S-LEC BL-1 manufactured by Sekisui Chemical Co., Ltd.) as a binder thereto such that the mass composition ratio (nitrogen-containing fluorine-based compound:binder) of the nitrogen-containing fluorine-based compound to the binder became 90:10, a surface coating material of Example 63 was obtained.

Example 64

By dispersing the "2-[3-[[perfluoro(pyrrolidinoacetyl)] amino]propyl-dimethyl-ammonium] acetate obtained in Synthesis Example 45 in water as a nitrogen-containing fluorine-based compound, a 5.0% by mass aqueous dispersion was obtained. Furthermore, by adding polyvinyl alcohol (reagent manufactured by Wako Pure Chemical Industries, Ltd.) as a binder thereto such that the mass composition ratio (nitrogen-containing fluorine-based compound:binder) of the nitrogen-containing fluorine-based compound to the binder became 50:50, a surface coating material of Example 64 was obtained.

Example 65

By mixing the 3-[3-[[perfluoro(2-methyl-3-morpholinopropanoyl)]amino]propyl-dimethyl-ammonium] propanesulfonate obtained in Synthesis Example 46 as a nitrogen-containing fluorine-based compound with a polyester-based aqueous urethane resin (manufactured by Dai-ichi Kogyo Seiyaku Co., Ltd., "Superflex 210", solid content of 35%, water of 65%) having an anionic hydrophilic group as a hydrophilic group in a ratio of 6.0% by mass, and by adding a nitrogen-containing fluorine-based compound and a binder thereto such that the mass composition ratio (nitrogen-containing fluorine-based compound:binder) of the nitrogen-containing fluorine-based compound to the binder became 15:85, a surface coating material of Example 65 was obtained.

Example 66

By dissolving the nitrogen-containing fluorine-based compound synthesized in Synthesis Example 47 in methanol, a 10.0% by mass methanol solution was prepared. Furthermore, by adding a polyvinyl butyral resin (S-LEC BL-1 manufactured by Sekisui Chemical Co., Ltd.) as a binder thereto such that the mass composition ratio (nitrogen-containing fluorine-based compound:binder) of the nitrogen-containing fluorine-based compound to the binder became 99.9:0.1, a surface coating material of Example 66 was obtained.

Example 67

By dissolving the nitrogen-containing fluorine-based compound synthesized in Synthesis Example 24 and an equal weight of the nitrogen-containing fluorine-based compound synthesized in Synthesis Example 40 in methanol, a 10.0% by mass methanol mixed solution was prepared. Furthermore, by adding a polyvinyl butyral resin (S-LEC BL-1 manufactured by Sekisui Chemical Co., Ltd.) as a binder thereto such that the mass composition ratio (nitrogen-containing fluorine-based compound:binder) of the nitrogen-containing fluorine-based compound to the binder became 20:80, a surface coating material of Example 67 was obtained.

Example 68

By dissolving the nitrogen-containing fluorine-based compound synthesized in Synthesis Example 48 in methanol, a 2.0% by mass methanol solution was prepared. Furthermore, by adding a polyvinyl butyral resin (S-LEC BL-1 manufactured by Sekisui Chemical Co., Ltd.) as a binder thereto such that the mass composition ratio (nitrogen-containing fluorine-based compound:binder) of the nitrogen-containing fluorine-based compound to the binder became 50:50, a surface coating material of Example 68 was obtained.

Example 69

By dissolving the nitrogen-containing fluorine-based compound synthesized in Synthesis Example 49 in methanol, a 1.0% by mass methanol solution was prepared. Furthermore, tetraethoxysilane (reagent manufactured by Wako Pure Chemical Industries, Ltd.) was added such that the mixing ratio with the nitrogen-containing fluorine-based compound became 10 to 90. In addition, by adding a polyvinyl butyral resin (S-LEC BL-1 manufactured by Sekisui Chemical Co., Ltd.) as a binder thereto such that the mass composition ratio (nitrogen-containing fluorine-based compound:binder) of the nitrogen-containing fluorine-based compound to the binder became 50:50, a surface coating material of Example 69 was obtained.

Example 70

By dissolving 16.0 parts by mass of perfluoro(2-methyl-3-piperidinopropionic acid) calcium obtained in Synthesis Example 24 as a nitrogen-containing fluorine-based compound and 4.0 parts by mass of polyvinyl butyral (manufactured by Sekisui Chemical Co., Ltd., "S-LEC B BL-1") having a hydroxyl group as a hydrophilic group in 180.0 parts by mass of methanol, a surface coating material of Example 70 was obtained.

Comparative Example 1

As shown in the following formula (425), by dissolving a silane coupling agent having a nitrogen-containing perfluoroalkyl group in methanol, a 2.0% by mass methanol solution was prepared. This was used as a surface coating material of Comparative Example 1.

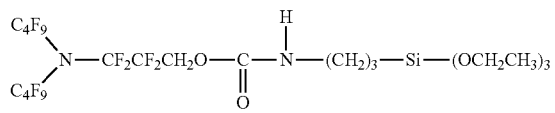

(425)

Comparative Example 2

As shown in the following formula (426), by dissolving a silane coupling agent having a nitrogen-containing perfluoroalkyl group in methanol, a 2.0% by mass methanol solution was prepared. This was used as a surface coating material of Comparative Example 2.

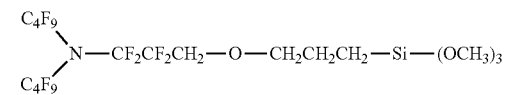

(426)

Comparative Example 3

As shown in the following formula (427), by dissolving a compound having a nitrogen-containing perfluoroalkyl group and a polyoxyalkylene group in the molecule in methanol, a 2.0% by mass methanol solution was prepared. This was used as a surface coating material of Comparative Example 3.

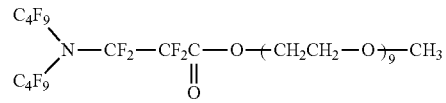

(427)

Comparative Example 4

By dissolving the nitrogen-containing fluorine-based compound synthesized in Synthesis Example 1 in methanol, a 0.1% by mass methanol solution was prepared. This was used as a surface coating material of Comparative Example 4.

Comparative Example 5

By dissolving a perfluorohexanoic acid calcium salt shown in the following formula (428) in methanol, a 2.0% by mass methanol solution was prepared. This was used as a surface coating material of Comparative Example 5.

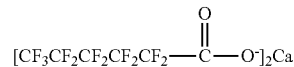

(428)

Comparative Example 6

As shown in the following formula (429), by dissolving a silane coupling agent having a nitrogen-containing perfluoroalkyl group in methanol, a 2.0% by mass methanol solution was prepared. This was used as a surface coating material of Comparative Example 6.

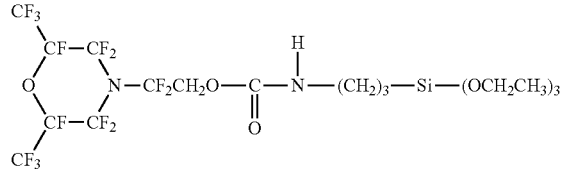

(429)

Comparative Example 7

As shown in the following formula (430), by dissolving a compound having a nitrogen-containing perfluoroalkyl group and a polyoxyalkylene group in the molecule in methanol, a 2.0% by mass methanol solution was prepared. This was used as a surface coating material of Comparative Example 7.

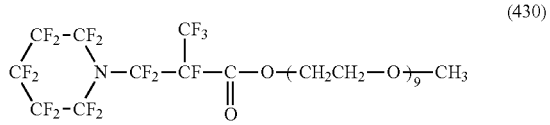
(430)

Comparative Example 8

By dissolving the nitrogen-containing fluorine-based compound synthesized in Synthesis Example 35 in methanol, a 0.1% by mass methanol solution was prepared. This was used as a surface coating material of Comparative Example 8.

<Evaluation of Hydrophilicity and Oil Repellency>

The contact angle measurement (drop method) was performed on the coating films obtained from the surface coating materials of the examples and the comparative examples, and evaluation of hydrophilicity and oil repellency thereof was performed thereon.

Specifically, first, each of glass plates was dipped in each of the surface coating materials of Examples 1, 2, 8, 12, 15, 16, 35 to 37, 41, 46, 55 to 57, and 61, and Comparative Examples 1, 2, and 6, then, taken out, and the solvent was removed by drying. As a result, a coating film was formed on the glass plate. In addition, in Examples 16 and 57, after natural drying, a curing treatment of the coating film by ultraviolet rays was performed.

Each of water and n-hexadecane (hereinafter, referred to as oil) were dropped on the obtained coating film, the angle (unit: degree) formed at the contact portion between the glass plate and the droplet was measured using an automatic contact angle meter (manufactured by Kyowa Interface Science Co., Ltd., "Drop Master 701").

In the dropping method of water and n-hexadecane, the following conditions were used.

Dropping volume: 2 µL/drop (water)
Dropping volume: 2 µL/drop (n-hexadecane)
Measurement temperature: room temperature (22±1° C.)

Here, as the contact angle value of water was lower, the hydrophilicity was excellent, the contact angle value of oil was increased, oil was likely to be repelled, that is, it could be said that oil repellency was excellent.

Therefore, in the evaluation of hydrophilicity and oil repellency, as a result of contact angle measurement, in a case where the contact angle of water to the coating film was 20° or less and the contact angle of n-hexadecane was 40° or greater, it was assumed that the nitrogen-containing fluorine-based compound has hydrophilicity and oil repellency (that is, the nitrogen-containing fluorine-based compound is a hydrophilic oil repellent).

The results of the linear nitrogen-containing fluorine-base compound are shown in the following Table 1, and the results of the cyclic nitrogen-containing fluorine-based compound are shown in the following Table 2, respectively.

TABLE 1

| | Surface coating material | | | | | | |
| | Nitrogen-containing fluorine-based compound | | Binder | Solvent | Glass: contact angle measurement | | |
| | | (parts by mass) | (parts by mass) | (parts by mass) | Water | n-Hexadecane | Determination |
|---|---|---|---|---|---|---|---|
| Example 1 | Synthesis Example 1 | 2.0 | — | 0 Methanol 98 | 6 | 54 | Hydrophilic oil repellent |
| Example 2 | Synthesis Example 2 | 2.0 | — | 0 Methanol 98 | 8 | 51 | Hydrophilic oil repellent |
| Example 8 | Synthesis Example 8 | 2.0 | — | 0 Methanol 98 | 11 | 65 | Hydrophilic oil repellent |
| Example 12 | Synthesis Example 1 | 0.2 | — | 0 Methanol 99.8 | 17 | 70 | Hydrophilic oil repellent |
| Example 15 | Synthesis Example 1 | 0.5 | Water glass 4.5 | Methanol 99.5 | 12 | 70 | Hydrophilic oil repellent |
| Example 16 | Synthesis Example 1 | 5.0 | PEGDA NK-A-200 45.0 | Methanol 95 | 14 | 74 | Hydrophilic oil repellent |
| Comp. Example 1 | Formula (425) | 2.0 | — | 0 Methanol 98 | 109 | 62 | Hydrophobic oil repellent |
| Comp. Example 2 | Formula (426) | 2.0 | — | 0 Methanol 98 | 105 | 65 | Hydrophobic oil repellent |

TABLE 2

| | Surface coating material | | | | | | |
| | Nitrogen-containing fluorine-based compound | | Binder | Solvent | Glass: contact angle measurement | | |
| | | (parts by mass) | (parts by mass) | (parts by mass) | Water | n-Hexadecane | Determination |
|---|---|---|---|---|---|---|---|
| Example 35 | Synthesis Example 24 | 2.0 | — | 0 Methanol 98 | 8 | 62 | Hydrophilic oil repellent |

TABLE 2-continued

| | | Surface coating material | | | | | Glass: contact angle | | |
|---|---|---|---|---|---|---|---|---|---|
| | | Nitrogen-containing fluorine-based compound | | Binder | | Solvent | | measurement | |
| | | (parts by mass) | | (parts by mass) | | (parts by mass) | Water | n-Hexadecane | Determination |
| Example 36 | Synthesis Example 25 | 2.0 | | — | | 0 | Methanol 98 | 11 | 66 | Hydrophilic oil repellent |
| Example 37 | Synthesis Example 26 | 2.0 | | — | | 0 | Methanol 98 | 9 | 70 | Hydrophilic oil repellent |
| Example 41 | Synthesis Example 30 | 2.0 | | — | | 0 | Methanol 98 | 12 | 71 | Hydrophilic oil repellent |
| Example 46 | Synthesis Example 35 | 2.0 | | — | | 0 | Methanol 98 | 8 | 44 | Hydrophilic oil repellent |
| Example 55 | Synthesis Example 42 | 0.2 | | Butyral BL-1 | | 1.8 | Methanol 99.8 | 15 | 67 | Hydrophilic oil repellent |
| Example 56 | Synthesis Example 42 | 1.3 | | Butyral KX-5 | | 0.7 | Methanol 98.7 | 14 | 69 | Hydrophilic oil repellent |
| Example 57 | Synthesis Example 24 | 5.0 | | PEGDA NK-A-200 | | 45.0 | Methanol 95 | 16 | 72 | Hydrophilic oil repellent |
| Example 61 | Synthesis Example 35 | 0.5 | | Water glass | | 4.5 | Methanol 99.5 | 18 | 66 | Hydrophilic oil repellent |
| Comp. Example 6 | Formula (429) | 2.0 | | — | | 0 | Methanol 98 | 66 | 106 | Hydrophobic oil repellent |

As shown in Tables 1 and 2, as a result of the contact angle measurement in Examples 1, 2, 8, 12, 15, and 16, and Examples 35 to 37, 41, 46, 55 to 57, and 61, for all the coating films, the contact angle of water was 20° or less, and the contact angle of n-hexadecane was 40° or greater. Therefore, it was confirmed that the coating films obtained from the surface coating materials of Examples 1, 2, 8, 12, 15, and 16, and Examples 35 to 37, 41, 46, 55 to 57, and 61 have hydrophilicity and oil repellency.

It was estimated that this is because a nitrogen-containing perfluoroalkyl group or a nitrogen-containing perfluoroalkylene group which is an oil repellency imparting group was aligned on the surface in air, and due to this, an oil repellent effect was exhibited, and a hydrophilicity imparting group such as a carbonyl group or a sulfonyl group was aligned on the surface when water came into contact, and due to this, a hydrophilicity effect is exhibited.

On the other hand, as a result of the contact angle measurement in Comparative Examples 1 and 2 and Comparative Example 6, it was confirmed that even a compound having a similar fluorine skeleton, depending on the functional group to be bonded, water repellency and oil repellency were imparted on the surface of the glass plate.

<Evaluation 1 by Filter Penetration Test>

A filter penetration test was performed on the coating films obtained from the surface coating materials of the examples and the comparative examples.

Specifically, first, a commercially available PTFE membrane filter (ADVANTEC T 100 A 047 A: pore size of 1 μm, porosity of 79%, thickness of 75 μm) was dipped in each of the surface coating materials of Examples 1 to 7, 9 to 14, 17 to 19, 20 to 30, 35 and 36, 38 to 55, 58 to 60, and 62 to 69, and Comparative Examples 3 to 5 and 7 to 9, and after the solution was sufficiently impregnated into the filter, the resulting product was taken out, and the solvent was removed by drying.

Next, water and n-hexadecane were respectively dropped to the manufactured PTFE membrane filter for a test, then, the penetrability thereof was visually determined based on the following definition, and the hydrophilicity and the oil repellency were evaluated. The results of the linear nitrogen-containing fluorine-base compound are shown in the following Table 3, and the results of the cyclic nitrogen-containing fluorine-based compound are shown in the following Table 4, respectively.

In the dropping method of water and n-hexadecane, the following conditions were used.

Dropping volume: (40 to 45) μL/drop (water)
Dropping volume: (20 to 25) μL/drop (n-hexadecane)
Dropping height: 5 cm from the surface of a filter
Dropping jig: polyspuit
Measurement temperature: room temperature (22±1° C.)

In addition, in the filter penetration tests of the following Tables 3 and 4, the definitions of the evaluation results were as follows.

A (immediate penetration): after droplets were dropped to a PTFE membrane filter and a polyester nonwoven fabric sheet, penetration occurred within 30 seconds B (slow penetration): after droplets were dropped, penetration occurred within a range of longer than 30 seconds and 5 minutes or less C (no penetration): after droplets were dropped, penetration did not occur for 30 minutes

TABLE 3

| | Surface coating material | | | | | PTFE filter penetration test | | |
|---|---|---|---|---|---|---|---|---|
| | Nitrogen-containing fluorine-based compound | (parts by mass) | Binder | (parts by mass) | Solvent (parts by mass) | Water | n-Hexadecane | Determination |
| Example 1 | Synthesis Example 1 | 2.0 | — | 0 | Methanol 98 | A | C | Hydrophilic oil repellent |
| Example 2 | Synthesis Example 2 | 2.0 | — | 0 | Methanol 98 | A | C | Hydrophilic oil repellent |
| Example 3 | Synthesis Example 3 | 2.0 | — | 0 | Methanol 98 | A | C | Hydrophilic oil repellent |
| Example 4 | Synthesis Example 4 | 2.0 | — | 0 | Methanol 98 | A | C | Hydrophilic oil repellent |
| Example 5 | Synthesis Example 5 | 2.0 | — | 0 | Methanol 98 | A | C | Hydrophilic oil repellent |
| Example 6 | Synthesis Example 6 | 2.0 | — | 0 | Methanol 98 | A | C | Hydrophilic oil repellent |
| Example 7 | Synthesis Example 7 | 2.0 | — | 0 | Methanol 98 | A | C | Hydrophilic oil repellent |
| Example 9 | Synthesis Example 9 | 2.0 | — | 0 | Methanol 98 | A | C | Hydrophilic oil repellent |
| Example 10 | Synthesis Example 10 | 2.0 | — | 0 | Methanol 98 | A | C | Hydrophilic oil repellent |
| Example 11 | Synthesis Example 11 | 2.0 | — | 0 | Methanol 98 | A | C | Hydrophilic oil repellent |
| Example 12 | Synthesis Example 1 | 0.2 | — | 0 | Methanol 99.8 | B | C | Hydrophilic oil repellent |
| Example 13 | Synthesis Example 11 | 0.2 | Butyral BL-1 | 1.8 | Methanol 99.8 | A | C | Hydrophilic oil repellent |
| Example 14 | Synthesis Example 11 | 1.3 | Butyral KX-5 | 0.7 | Methanol 98.7 | A | C | Hydrophilic oil repellent |
| Example 17 | Synthesis Example 11 | 10.0 | Butyral BL-1 | 1.0 | Methanol 90 | A | C | Hydrophilic oil repellent |
| Example 18 | Synthesis Example 11 | 10.0 | Butyral BL-1 | 10.0 | Methanol 90 | A | C | Hydrophilic oil repellent |
| Example 19 | Synthesis Example 11 | 10.0 | Butyral BL-1 | 30.0 | Methanol 90 | A | C | Hydrophilic oil repellent |
| Example 20 | Synthesis Example 12 | 10.0 | Butyral BL-1 | 10.0 | Methanol 90 | A | C | Hydrophilic oil repellent |
| Example 21 | Synthesis Example 13 | 10.0 | Butyral BL-1 | 10.0 | Methanol 90 | A | C | Hydrophilic oil repellent |
| Example 22 | Synthesis Example 14 | 10.0 | Butyral BL-1 | 10.0 | Methanol 90 | A | C | Hydrophilic oil repellent |
| Example 23 | Synthesis Example 15 | 50.0 | Butyral BL-1 | 5.6 | Ethanol 45/Water 5 | A | C | Hydrophilic oil repellent |
| Example 24 | Synthesis Example 16 | 5.0 | Polyvinyl alcohol | 5.0 | Water 95 | A | C | Hydrophilic oil repellent |
| Example 25 | Synthesis Example 17 | 6.0 | Polyurethane Superflex 210 | 33.0 | Water 61 | A | C | Hydrophilic oil repellent |
| Example 26 | Synthesis Example 18 | 10.0 | Butyral BL-1 | 0.01 | Methanol 90 | A | C | Hydrophilic oil repellent |
| Example 27 | Synthesis Example 1 Synthesis Example 9 | 5.0 5.0 | Butyral BL-1 | 40.0 | Ethanol 90 | A | C | Hydrophilic oil repellent |
| Example 28 | Synthesis Example 19 | 2.0 | Butyral BL-1 | 2.0 | Methanol 98 | A | C | Hydrophilic oil repellent |
| Example 29 | Synthesis Example 20 | 2.0 | Butyral BL-1 | 2.0 | Methanol 98 | A | C | Hydrophilic oil repellent |
| Example 30 | Synthesis Example 21 | 1.0 | Butyral BL-1 Tetraethoxysilane | 1.0 0.1 | Methanol 99 | A | C | Hydrophilic oil repellent |
| Comparative Example 3 | Formula (427) | 2.0 | — | 0 | Methanol 98 | A | A | Hydrophilic lipophilic |
| Comparative Example 4 | Synthesis Example 1 | 0.1 | — | 0 | Methanol 99.9 | C | A | Hydrophobic lipophilic |
| Comparative Example 5 | Formula (428) | 2.0 | — | 0.0 | Methanol 98 | C | B | Hydrophobic lipophilic |

TABLE 4

| | Surface coating material | | | | | | PTFE filter penetration test | | |
|---|---|---|---|---|---|---|---|---|---|
| | Nitrogen-containing fluorine-based compound | (parts by mass) | Binder | (parts by mass) | Solvent | (parts by mass) | Water | n-Hexadecane | Determination |
| Example 35 | Synthesis Example 24 | 2.0 | — | 0 | Methanol | 98 | A | C | Hydrophilic oil repellent |
| Example 36 | Synthesis Example 25 | 2.0 | — | 0 | Methanol | 98 | B | C | Hydrophilic oil repellent |
| Example 38 | Synthesis Example 27 | 2.0 | — | 0 | Methanol | 98 | A | C | Hydrophilic oil repellent |
| Example 39 | Synthesis Example 28 | 2.0 | — | 0 | Methanol | 98 | A | C | Hydrophilic oil repellent |
| Example 40 | Synthesis Example 29 | 2.0 | — | 0 | Methanol | 98 | A | C | Hydrophilic oil repellent |
| Example 41 | Synthesis Example 30 | 2.0 | — | 0 | Methanol | 98 | B | C | Hydrophilic oil repellent |
| Example 42 | Synthesis Example 31 | 2.0 | — | 0 | Methanol | 98 | B | C | Hydrophilic oil repellent |
| Example 43 | Synthesis Example 32 | 2.0 | — | 0 | Methanol | 98 | A | C | Hydrophilic oil repellent |
| Example 44 | Synthesis Example 33 | 2.0 | — | 0 | Methanol | 98 | A | C | Hydrophilic oil repellent |
| Example 45 | Synthesis Example 34 | 2.0 | — | 0 | Methanol | 98 | A | C | Hydrophilic oil repellent |
| Example 46 | Synthesis Example 35 | 2.0 | — | 0 | Methanol | 98 | A | C | Hydrophilic oil repellent |
| Example 47 | Synthesis Example 36 | 2.0 | — | 0 | Methanol | 98 | A | C | Hydrophilic oil repellent |
| Example 48 | Synthesis Example 37 | 2.0 | — | 0 | Methanol | 98 | A | C | Hydrophilic oil repellent |
| Example 49 | Synthesis Example 38 | 2.0 | — | 0 | Methanol | 98 | B | C | Hydrophilic oil repellent |
| Example 50 | Synthesis Example 39 | 2.0 | — | 0 | Methanol | 98 | B | C | Hydrophilic oil repellent |
| Example 51 | Synthesis Example 40 | 2.0 | — | 0 | Methanol | 98 | A | C | Hydrophilic oil repellent |
| Example 52 | Synthesis Example 41 | 2.0 | — | 0 | Methanol | 98 | A | C | Hydrophilic oil repellent |
| Example 53 | Synthesis Example 42 | 2.0 | — | 0 | Methanol | 98 | A | C | Hydrophilic oil repellent |
| Example 54 | Synthesis Example 35 | 0.2 | — | 0 | Methanol | 99.8 | A | C | Hydrophilic oil repellent |
| Example 55 | Synthesis Example 42 | 0.2 | Butyral BL-1 | 1.8 | Methanol | 99.8 | A | C | Hydrophilic oil repellent |
| Example 58 | Synthesis Example 42 | 10.0 | Butyral BL-1 | 1.0 | Methanol | 90 | A | C | Hydrophilic oil repellent |
| Example 59 | Synthesis Example 42 | 10.0 | Butyral BL-1 | 10.0 | Methanol | 90 | A | C | Hydrophilic oil repellent |
| Example 60 | Synthesis Example 42 | 10.0 | Butyral BL-1 | 30.0 | Methanol | 90 | A | C | Hydrophilic oil repellent |
| Example 62 | Synthesis Example 43 | 10.0 | Butyral BL-1 | 10.0 | Methanol | 90 | A | C | Hydrophilic oil repellent |
| Example 63 | Synthesis Example 44 | 50.0 | Butyral BL-1 | 5.6 | Ethanol 45/Water | 5 | A | C | Hydrophilic oil repellent |
| Example 64 | Synthesis Example 45 | 5.0 | Polyvinyl alcohol | 5.0 | Water | 95 | A | C | Hydrophilic oil repellent |
| Example 65 | Synthesis Example 46 | 6.0 | Polyurethane Superflex 210 | 33.0 | Water | 61 | A | C | Hydrophilic oil repellent |
| Example 66 | Synthesis Example 47 | 10.0 | Butyral BL-1 | 0.01 | Methanol | 90 | A | C | Hydrophilic oil repellent |
| Example 67 | Synthesis Example 24 Synthesis Example 40 | 5.0 5.0 | Butyral BL-1 | 40.0 | Ethanol | 90 | A | C | Hydrophilic oil repellent |
| Example 68 | Synthesis Example 48 | 2.0 | Butyral BL-1 | 2.0 | Methanol | 98 | A | C | Hydrophilic oil repellent |
| Example 69 | Synthesis Example 49 | 1.0 | Butyral BL-1 Tetraethoxysilane | 1.0 0.1 | Methanol | 99 | A | C | Hydrophilic oil repellent |
| Comparative Example 7 | Formula (430) | 2.0 | — | 0 | Methanol | 98 | A | A | Hydrophilic lipophilic |
| Comparative Example 8 | Synthesis Example 35 | 0.1 | — | 0 | Methanol | 99.9 | C | A | Hydrophobia lipophilic |

TABLE 4-continued

| | | Surface coating material | | | | PTFE filter penetration test | | |
|---|---|---|---|---|---|---|---|---|
| | | Nitrogen-containing fluorine-based compound (parts by mass) | Binder (parts by mass) | Solvent (parts by mass) | | Water | n-Hexadecane | Determination |
| Comparative Example 5 | Formula (428) | 2.0 | — | 0 | Methanol 98 | C | B | Hydrophobic lipophilic |

As shown in Tables 3 and 4, as a result of the filter penetration tests in Examples 1 to 7, 9 to 14, 17 to 19, and 20 to 30, and Examples 35 and 36, 38 to 55, 58 to 60, and 62 to 69, it was confirmed that all the filters (surface coating agent) for a test had hydrophilicity and oil repellency, the penetration result of water was A (immediate penetration) or B (slow penetration), and the penetration result of n-hexadecane was C (no penetration).

In contrast, as a result of the filter penetration tests of Comparative Examples 3 and 7, it was confirmed that the PTFE membrane filters treated with each of surface coating materials of Comparative Examples 3 and 7 were hydrophilic and lipophilic, from the fact that both the penetration results of water and n-hexadecane were A (immediate penetration).

In addition, as a result of the filter penetration tests of Comparative Examples 4 and 8, it was confirmed that since the concentrations of the nitrogen-containing fluorine-based compound in the surface coating materials of Comparative Examples 4 and 8 were low, water did not penetrate and was hydrophobic and lipophilic.

In addition, as a result of the filter penetration test of Comparative Example 5, it was confirmed that in the structure having a relatively small amount of fluorine as shown in Comparative Example 5, water did not penetrate and was hydrophobic and lipophilic.

As shown in FIG. 1, if water and n-hexadecane were respectively dropped to the PTFE membrane filter surface-treated with the hydrophilic oil repellent of the present invention containing a linear or cyclic nitrogen-containing fluorine-based compound, water wet spread on the PTFE membrane filter and penetrated into the PTFE membrane filter. In contrast, n-hexadecane was maintained in a shape of oil droplets.

Figure 2:
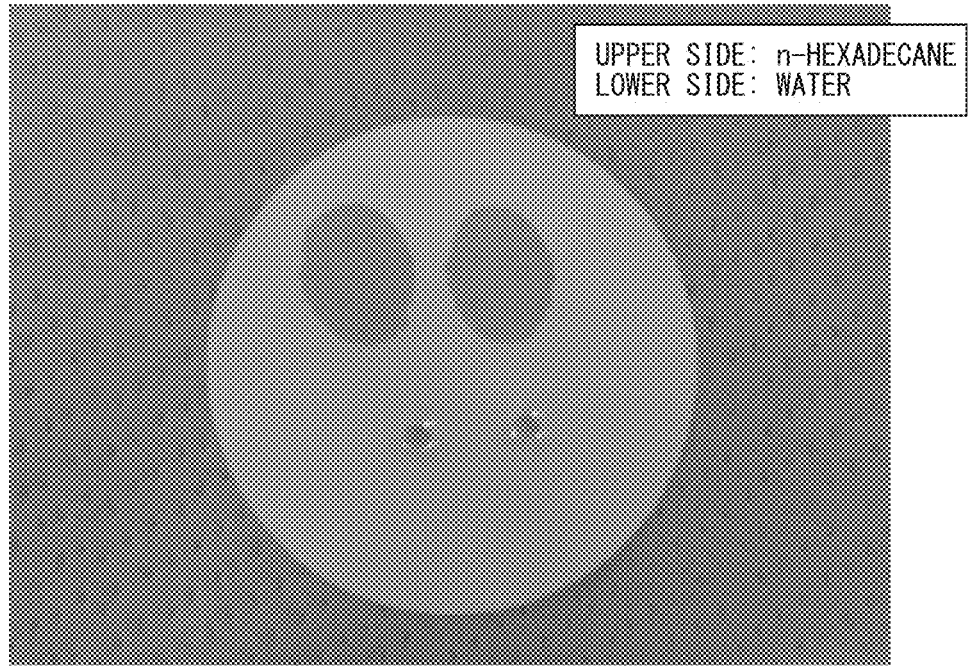
FIG. 2 is a photograph showing the results of a PTFE filter penetration test according to a comparative example.

In contrast, as shown in FIG. 2, if water and n-hexadecane were respectively dropped to an untreated PTFE membrane filter, water was maintained in a shape of water droplets, and n-hexadecane wet spread on the PTFE membrane filter and penetrated into the PTFE membrane filter.

<Evaluation 2 by Filter Penetration Test>

After the substrate, in the filter penetration test described above, was changed from a PTFE membrane filter to a polyester nonwoven fabric, a filter penetration test was performed.

Specifically, first, a polyester nonwoven fabric (basis weight of 80 g/m$^2$, thickness of 0.40 mm) was dipped in each of the surface coating materials of Examples 32 to 34, and after the solution was sufficiently impregnated into the filter, the resulting product was taken out, and the solvent was removed by drying.

Next, water and n-hexadecane were respectively dropped to the manufactured polyester nonwoven fabric sheet for a test, then, the penetrability thereof was visually determined based on the following definition, and the hydrophilicity and the oil repellency were evaluated. The results are shown in the following Table 5.

The dropping method of water and n-hexadecane and the definition of the evaluation results were the same as the evaluation described above.

TABLE 5

| | | Surface coating material | | | Filter penetration test (nonwoven fabric) | | |
|---|---|---|---|---|---|---|---|
| | | Nitrogen-containing fluorine-based compound (parts by mass) | Binder (parts by mass) | Solvent (parts by mass) | Water | n-Hexadecane | Determination |
| Example 32 | Synthesis Example 16 | 2.0 | — | 0 | Ethanol 98 | A | C | Hydrophilic oil repellent |
| Example 33 | Synthesis Example 22 | 2.0 | — | 0 | Ethanol 98 | A | C | Hydrophilic oil repellent |
| Example 34 | Synthesis Example 23 | 2.0 | — | 0 | Ethanol 98 | A | C | Hydrophilic oil repellent |

<Evaluation by Particle Packed Layer Penetration Test>

The surface coating materials of Examples 31 and 70 were spray-dried using a spray dryer (ADL 311 S-A, manufactured by YAMATO SCIENTIFIC CO., LTD.), and particles having a most frequent diameter of 4 μm were obtained. When the obtained particles were spread on No. 5C filter paper (manufactured by Kiriyama glass Co., diameter of 21 mm) and water and n-hexadecane were dropped, water penetrated instantaneously, but n-hexadecane did not penetrate. The results are shown in the following Table 6.

TABLE 6

| | Surface coating material | | | | | Particle packed layer penetration test | | |
| --- | --- | --- | --- | --- | --- | --- | --- | --- |
| | Nitrogen-containing fluorine-based compound (parts by mass) | | Binder (parts by mass) | | Solvent (parts by mass) | Water | n-Hexadecane | Determination |
| Example 31 | Synthesis Example 1 | 16.0 | Butyral BL-1 | 4.0 | Methanol 180 | A | C | Hydrophilic oil repellent |
| Example 70 | Synthesis Example 24 | 16.0 | Butyral BL-1 | 4.0 | Methanol 180 | A | C | Hydrophilic oil repellent |

<Evaluation 1 by Oil Water Separation Test>

Nonwoven fabric formed of polypropylene (basis weight: 72 g/m², thickness: 0.26 mm) was cut into a circular filter shape having a diameter of 47 mm, then, the fabric was subjected to an immersion treatment with a solution (surface coating material) obtained by dissolving 9 g of perfluoro(3-dibutylaminopropionic acid) calcium obtained in Synthesis Example 1 and 1 g of polyvinyl butyral (S-LEC BL-1 manufactured by Sekisui Chemical Co., Ltd.) in 90 g of methanol, and after natural drying (increased amount after drying: 0.0464 g), oil water separation test was performed using a normal pressure filtration apparatus. As a test solution, a mixed solution of 40 mL of water and 40 mL of n-hexadecane was used.

As a result of shaking the test solution using normal pressure filtration apparatus and supplying the test solution, water passed vigorously through the nonwoven fabric, but n-hexadecane could not pass through the nonwoven fabric, and oil and water were completely separated in about 72 seconds.

<Evaluation 2 by Oil Water Separation Test>

Nonwoven fabric formed of polypropylene (basis weight: 72 g/m², thickness: 0.26 mm) was cut into a circular filter shape having a diameter of 47 mm, then, the fabric was subjected to an immersion treatment with a solution (surface treatment material) obtained by dissolving 9 g of perfluoro [2-methyl-3-(3,5-dimethylmorpholino)propionic acid] calcium obtained in Synthesis Example 35 and 1 g of polyvinyl butyral (S-LEC BL-1 manufactured by Sekisui Chemical Co., Ltd.) in 90 g of methanol, and after natural drying (increased amount after drying: 0.0444 g), oil water separation test was performed using a normal pressure filtration apparatus. As a test solution, a mixed solution of 40 mL of water and 40 mL of n-hexadecane was used.

As a result of shaking the test solution using normal pressure filtration apparatus and supplying the test solution, water passed vigorously through the nonwoven fabric, but n-hexadecane could not pass through the nonwoven fabric, and oil and water were completely separated in about 85 seconds.

INDUSTRIAL APPLICABILITY

Since a hydrophilic oil repellent of the present invention, a dispersion thereof and a solution thereof can impart hydrophilicity and oil repellency, it is possible to easily form a coating film having an antifouling function and an oil-water separation filter material, and thus, the hydrophilic oil repellent, the dispersion, and the solution are industrially applicable.

The invention claimed is:
1. A hydrophilic oil repellent, comprising:
one or more nitrogen-containing fluorine-based compounds represented by the following formulas (1) to (4):

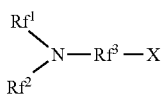 (1)

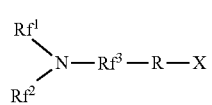 (2)

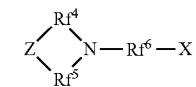 (3)

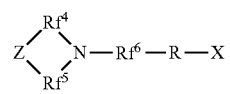 (4)

wherein in the above formulas (1) and (2), $Rf^1$ and $Rf^2$ each represent a linear or branched perfluoroalkyl group having 1 to 6 carbon atoms, which are the same as or different from each other, and $Rf^3$ represents a linear or branched perfluoroalkylene group having 1 to 6 carbon atoms;

in the above formulas (3) and (4), $Rf^4$, $Rf^5$, and $Rf^6$ each represent a linear or branched perfluoroalkylene group having 1 to 6 carbon atoms, which are the same as or different from each other, and Z includes any one of an oxygen atom, a nitrogen atom, a $CF_2$ group, and a CF group;

in the above formulas (2) and (4), R represents a linking group which is a divalent organic group; and in the above formulas (1) to (4), X is:
an anion type hydrophilic imparting group having "—$CO_2M^1$", "—$SO_3M^1$", "—$OSO_3M^1$", "—$OP(OH)O_2M^1$", "—$OPO_3M^1{}_2$", "=$O_2PO_2M^1$", or "—$PO(OH)_y(OM^1)_{2-y}$," wherein $M^1$ represents an alkali metal, an alkali earth metal, Mg, Al, or $R^1R^2R^3R^4N^+$, and wherein $R^1$ to $R^4$ are each independently a hydrogen atom or a linear or branched alkyl group having 1 to 20 carbon atoms, and y represents an integer of 0 to 2, at a terminal, or a cation type hydrophilicity imparting group having "—$N^+R^5R^6R^7.Cl^-$", "—$N^+R^5R^6R^7.Br^-$", "—$N^+R^5R^6R^7.I^-$", "—$N^+R^5R^6R^7.CH_3SO_3^-$", "—$N^+R^5R^6R^7.R^7SO_4^-$", "-$N^+R^5R^6R^7.NO_3^-$", "(-$N^+R^5R^6R^7)_2CO_3^{2-}$", or "(-$N^+R^5R^6R^7)_2SO_4^{2-}$", wherein $R^5$ to $R^7$ are hydrogen atoms or each independently a linear or branched alkyl group having 1 to 20 carbon atoms, at a terminal, or an amphoteric hydrophilicity imparting group having any one terminal of a carboxybetaine type, a sulfobetaine type, an amine oxide type, and a phosphobetaine type.

2. A production method of the hydrophilic oil repellent according to claim 1,
wherein a carboxylic acid halide or a sulfonic acid halide having a nitrogen-containing perfluoroalkyl group represented by the following formula (5) or (6) is used as a raw material:

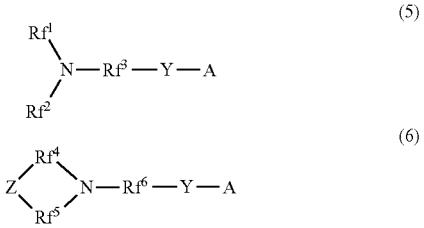

wherein in the above formula (5), $Rf^1$ and $Rf^2$ each represent a linear or branched perfluoroalkyl group having 1 to 6 carbon atoms, which are the same as or different from each other, and $Rf^3$ represents a linear or branched perfluoroalkylene group having 1 to 6 carbon atoms;
in the above formula (6), $Rf^4$, $Rf^5$, and $Rf^6$ each represent a linear or branched perfluoroalkylene group having 1 to 6 carbon atoms, which are the same as or different from each other, and Z includes any one of an oxygen atom, a nitrogen atom, a $CF_2$ group, and a CF group;
in the above formulas (5) and (6), Y represents CO or $SO_2$; and
in the above formulas (5) and (6), A represents any one halogen atom selected from the group consisting of fluorine, chlorine, bromine, and iodine.

3. A surface coating material, comprising:
the hydrophilic oil repellent according to claim 1; and
a solvent,
wherein the mass composition ratio between the hydrophilic oil repellent and the solvent is within a range of 0.2 to 50:99.8 to 50.

4. The surface coating material according to claim 3,
wherein the solvent is water, an alcohol, or a mixture of water and an alcohol.

5. The surface coating material according to claim 3, further comprising:
a binder,
wherein the mass composition ratio between the hydrophilic oil repellent and the binder is within a range of 0.2 to 99.9:99.8 to 0.1.

6. The surface coating material according to claim 3,
wherein the binder includes any one of a resin, and water glass.

7. The surface coating material according to claim 6,
wherein the resin is a water soluble resin.

8. A coating film, comprising:
the hydrophilic oil repellent according to claim 1.

9. The coating film according to claim 8, further comprising:
a binder,
wherein the mass composition ratio between the hydrophilic oil repellent and the binder is within a range of 0.2 to 99.9:99.8 to 0.1.

10. An oil-water separation filter material, comprising:
any one or more of the coating film according to claim 8.

11. A resin composition, comprising:
the hydrophilic oil repellent according to claim 1; and
a resin,
wherein the mass composition ratio between the hydrophilic oil repellent and the resin is within a range of 0.2 to 99.9:99.8 to 0.1.

12. A porous body, comprising:
the hydrophilic oil repellent according to claim 1.

13. A porous body,
wherein the hydrophilic oil repellent according to claim 1 is bonded with a resin or a vitreous material.

* * * * *